(12) United States Patent
Sabatini et al.

(10) Patent No.: US 8,258,271 B2
(45) Date of Patent: Sep. 4, 2012

(54) MTOR KINASE-ASSOCIATED PROTEINS

(75) Inventors: David M. Sabatini, Cambridge, MA (US); Do-Hyung Kim, Minneapolis, MN (US); Dos D. Sarbassov, Shrewsbury, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 254 days.

(21) Appl. No.: 11/436,394

(22) Filed: May 17, 2006

(65) Prior Publication Data
US 2007/0009936 A1    Jan. 11, 2007

Related U.S. Application Data

(62) Division of application No. 10/782,244, filed on Feb. 18, 2004, now Pat. No. 7,052,870.

(60) Provisional application No. 60/448,035, filed on Feb. 18, 2003.

(51) Int. Cl.
*C07K 14/00* (2006.01)
(52) U.S. Cl. ..................................... 530/827
(58) Field of Classification Search .................... None
See application file for complete search history.

(56) References Cited

U.S. PATENT DOCUMENTS
2005/0227301 A1* 10/2005 Glover et al. ................ 435/7.23

FOREIGN PATENT DOCUMENTS
WO    WO 2004/074448    9/2004

OTHER PUBLICATIONS

Ohara et al. NCBI, KIAA1999 protein, 2002. pp. 1 and 2.*
Glover et al, from US 20050227301 priority date Jan. 10, 2003 SEQ ID No. 282. Alignment with SEQ ID No. 3.*
Nishiuma et al, Characterization of the phosphoproteins and protein kinase activity in mTOR immunoprecipitates. Biochem Biophys Res Commun. Nov. 18, 1998;252(2):440-4.*
Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
Brunn et al, The mammalian target of rapamycin phosphorylates sites having a (Ser/Thr)-Pro motif and is activated by antibodies to a region near its COOH terminus. J Biol Chem. Dec. 19, 1997;272(51):32547-50.*
Guo et al, Protein tolerance to random amino acid change. Proc Natl Acad Sci U S A. Jun. 22, 2004;101(25):9205-9210. Epub Jun. 14, 2004.*
Wishart et al, A single mutation converts a novel phosphotyrosine binding domain into a dual-specificity phosphatase. J Biol Chem. Nov. 10, 1995;270(45):26782-26785.*
Avruch et al, Amino acid regulation of TOR complex 1. Am J Physiol Endocrinol Metab 296: E592-E602, 2009.*
NCBI Swiss-Prot database Acc. No. P42345; Nov. 3, 2009.*
USPTO in house BLAST search with NCBI Swiss-Prot database Acc. No. P42345. Performed Nov. 27, 2009.*
GenBank Acc. No. Q6QI06 from Gerhard et al, Genome Res. 14 (10B), 2121-27 (2004). Alignment with SEQ ID No. 3.*
GenBank Acc. No. NP_071799 from Avruch et al, Am J Physiol Endocrinol Metab 296: E592-E602, 2009. Alignment with SEQ ID No. 3.*
Sabatini et al, RAFT1: a mammalian protein that binds to FKBP12 in a rapamycin-dependent fashion and is homologous to yeast TORs. Cell. Jul. 15, 1994;78(1):35-43.*
Rost, Enzyme function less conserved than anticipated. J Mol Biol. Apr. 26, 2002;318(2):595-608.*
Fitter et al, Transmembrane 4 superfamily protein CD151 (PETA-3) associates with beta 1 and alpha IIb beta 3 integrins in haemopoietic cell lines and modulates cell-cell adhesion. Biochem J. Feb. 15, 1999;338 ( Pt 1):61-70.*
Michel et al, Reciprocal Regulation of Endothelial Nitric-oxide Synthase by Ca2+-Calmodulin and Caveolin. J Biol Chem. Jun. 20, 1997;272(25):15583-6.*
Kim et al, Evidence that the "NF" motif in transmembrane domain 4 of presenilin 1 is critical for binding with PEN-2. J Biol Chem. Dec. 23, 2005;280(51):41953-66. Epub Oct. 18, 2005.*
USPTO in house search—"1% chaps" coimmunoprecipitation—GoogleScholar. Performed Jul. 8, 2010.*
Kaftan et al, Effects of rapamycin on ryanodine receptor/Ca(2+)-release channels from cardiac muscle. Circ Res. Jun. 1996;78(6):990-7.*
Phelan, Basic Techniques in Mammalian Cell Tissue Culture. In: Current Protocols in Cell Biology 1.1.1-1.1.18, Sep. 2007. p. 1.1.1-1.1.18.*
USPTO in house BLAST performed Mar. 29, 2012. Alignment SEQ ID No. 3 vs gi:984525.*
Alessi et al., *Curr. Biol.*, 7:261 (1997).
Alessi et al., "Mechanism of activation of protein kinase B by insulin and IGF-1" *Embo J.*, 15:6541 (1996).
Balendran et al., *Curr Biol*, 9:393 (1999).
Biondi et al., *Embo J.*, 20:4380 (2001).
Brown et al., *Nature* 369:756-758 (1994).
Brunet et al., *Cell*, 96:857-868 (1999).
Burnett et al., *PNAS*, 95:1432-1437 (1998).
Chen et al., *Genes Dev.*, 15:2203 (2001).
Chinni and Sarkar, *Clin. Cancer Res.*, 8:1228-1236 (2002).
Cho et al., *J. Biol. Chem.*, 276:38349 (2001).
Cho et al., *Science*, 292:1728 (2001).
del Pesso et al.,"Regulation of the forkhead transcription factor FKHR, but not the PAX3-FKHR fusion protein, by the serine/threibube kinase Akt," *Oncogene*, 18:7328-7333 (1999).
Edinger et al., "Akt Maintains Cell Size and Survival by Increasing mTOR-Dependent Nutrient Uptake," *Molecular Biology of the Cell*, 13(7):2276-2288 (2002).
Edinger et al., "Differential Effects of Rapamycin on Mammalian Target of Rapamycin Signaling Functions in Mammalian Cells," *Cancer Research*, 63(23):8451-8460 (2003).
Elks and Manganiello, *Endocrinology*, 116:2119-2121 (1985).

(Continued)

*Primary Examiner* — Sheridan Swope
(74) *Attorney, Agent, or Firm* — Ropes & Gray LLP

(57) ABSTRACT

The invention describes isolated mTOR-associated proteins ("mTOR-APs") as well as isolated variants and fragments thereof and the isolated nucleic acids encoding them. The invention also describes vectors and host cells containing nucleic acid encoding an mTOR-AP polypeptide and methods for producing an mTOR-AP polypeptide. Also described are methods for screening for compounds which modulate mTOR-AP activity and methods for treating or preventing a disorder that is responsive to mTOR-AP modulation.

17 Claims, 25 Drawing Sheets

OTHER PUBLICATIONS

Feng et al., *J. Biol. Chem.*, 279:41189 (2004).
Frost and Lane, *J. Biol. Chem.*, 260:2646-2652 (1985).
Guba et al., *Nat. Med.*, 8:128-135 (2002).
Guertin et al., "An Expanding Role for mTOR in Cancer," Trends in Molecular Medicine, *Elsevier Current Trends*, 11(8):353-361 (2005).
Harrington et al., *J. Cell Biol.*, 166:213-223 (2004).
Hill et al., "Insulin-stimulated Protein Kinase B Phosphorylation on Ser-473 is independent of its activity and occurs through a staurosporine-insensitive kinase," *J. Biol. Chem.*, 276:25643 (2001).
Hresko et al., "mTOR Center Dot RICTOR is the Ser(473) Kinase for Akt/Protein Kinase B in 3T3-L1 Adipocytes," *Journal of Biological Chemistry*, 280(49):40406-40416 (2005).
Jacinto et al., "Mammalian TOR Complex 2 Controls the Actin Cytoskeleton and is Rapamycin Insensitive," *Nature Cell Biology*, 6:1122-1128 (2004).
Kane and Weiss, *Immunol. Rev.*, 192:7-20 (2003).
Kim et al., *Cell*, 110:163-175 (2002).
Kops et al. *Nature*, 398:630-634 (1999).
Lawlor et al., *Embo J.*, 21:3728-3738 (2002).
Lee et al., *Cancer Res.*, 64:6906-6914 (2004).
Loewith et al., *Mol. Cell.*, 10:457 (2002).
Lynch et al., *Oncogene*, 18:8024 (1999).
Morrisett et al., *Transplant Proc.*, 35:143S-150S (2003).
Persad et al., *J. Biol. Chem*, 276:27462 (2001).
Radimerski et al., *Genes Dev.*, 16:2627 (2002).
Rena et al., *Embo J.*, 21:2263-2271 (2002).
Sabers et al., *J. Biol. Chem.*, 270:815-822 (1995).
Sarbassov et al., "Growing Roles for the mTOR Pathway," *Current Opinion in Cell Biology, Current Science*, 17(6):596-603 (2005).
Sarbassov et al., "Phosphorylation and Regulation of Akt/PKB by the Rictor-mTor Complex," *Science*, 307(5712): 1098-1101 (2005).
Sarbassov et al., "Prolonged Rapamycin Treatment Inhibits mTORC2 Assembly and Akt/PKB," *Mol. Cell.*, 22(2):159-168 (2006).
Scheid and Woodgett, *FEBS Lett.*, 546:108-112 (2003).
Scheid et al., *Mol Cell Biol.*, 22:6247-6260 (2002).
Shi et al., "MTOR Inhibitors Activate the AKT Kinase in Multiple Myeloma Cells by Upregulating the IGF-1/IRS-1/PI-3 Kinase Cascade," *Blood*, 104(11):915A (2004).
Stephens et al., *Science*, 279:710 (1998).
Taccioli et al., *Immunity*, 9:355 (1998).
Takaishi et al., *Proc. Natl. Acad. Sci. USA*, 96:11836-11841 (1999).
Tang et al., *J. Biol. Chem.*, 274:16741-16746 (1999).
Toker and Newton, *J. Biol. Chem.*, 275:8271 (2000).
Tremblay and Marette, *J. Biol. Chem.*, 276:38052-38060 (2001).
Um et al., *Nature*, 431:200-205 (2004).
Wijkander et al., *Endocrinology*, 139:219-227 (1998).
Williiams et al., *Curr Biol.*, 10:439 (2000).
Xu et al., *Cell Growth Differ*, 13:285-296 (2002).
Yang et al., *Mol. Cell.*, 9:1227-1240 (2002).
Zhou et al., *Arterioscler Thromb. Vasc. Biol.*, 23:2015-2020 (2003).
Sarbassov, Dos D., et al., "Rictor, a Novel Binding Partner of mTOR, Defines a Rapamycin-Insensitive and Raptor-Independent Pathway that Regulates the Cytoskeleton", Current Biology, 14: 1296-1302 (2004).
Neshat, M.S., et al., "Enhanced sensitivity of PTEN-deficient tumors to inhibition of FRAP/mTOR," PNAS, 98(18):10314-10319 (2001).
Mammalian Gene Collection (MGC) Program Team: "Generation and Initial Analysis of More Than 15,000 Full-Length Human and Mouse cDNA Sequences", Proceedings of the National Academy of Sciences of USA, National Academy of Science, 99(26): 16899-16903 (2002).

Kim, D-H., et al., "GβL, a Positive Regulator of the Rapamycin-Sensitive Pathway Required for the Nutrient-Sensitive Interaction between Raptor and mTOR," Molecular Cell, 11:895-904 (2003).
Vogt, P.K., "PI 3-kinase, mTOR, protein synthesis and cancer," Trends in Molecular Medicine, 7(11):482-484 (2001).
Kwiatkowski, D.J., et al., "A mouse model of TSC1 reveals sex-dependent lethality from liver hemangiomas, and up-regulation of p70S6 kinase activity in Tsc1 null cells," Human Molecular Genetics, 11(5):525-534 (2002).
Sabatini, D.M., et al., "RAFT1: A mammalian protein that binds to FKBP12 in a rapamycin-dependent fashion and is homologous to yeast TORs," Cell, 78(1):35-43 (1994) abstract.
Rodgers, B.D., et al., "Insulin regulation of a novel WD-40 repeat protein in adipocytes," Journal of Endocrinology, 168:325-332 (2001).
Roberg, K.J., et al., "Control of Amino Acid Permease Sorting in the Late Secretory Pathway of *Saccharomyces cerevisiae* by SEC13, LST4, LST7 and LST8," Genetics, 147:1569-1584 (1997).
Kim, D-H., et al., "mTOR Interacts with Raptor to Form a Nutrient-Sensitive Complex that Signals to the Cell Growth Machinery," Cell, 110(2):163-175 (2002).
Ochotorena, I.L., et al., "Conserved Wat1/Pop3 WD-repeat protein of fission yeast secures genome stability through microtubule integrity and may be involved in mRNA maturation," Journal of Cell Science, 114:2911-2920 (2001).
Gao, X., et al., "Tsc tumour suppressor proteins antagonize amino-acid-TOR signalling," Nature Cell Biology, 4:699-704 (2002).
Hentges, K.E., et al., "FRAP/mTOR is required for proliferation and patterning during embryonic development in the mouse," PNAS, 98(24):13796-13801 (2001).
Hara, K., et al., "Raptor, a Binding Partner of Target of Rapamycin (TOR), Mediates TOR Action," Cell, 110:177-189 (2002).
Podsypanina, K., et al., "An inhibitor of mTOR reduces neoplasia and normalizes p70/S6 kinase activity in Pten+/− mice," PNAS, 98(18):10320-10325 (2001).
Riken Genome Exploration Research Group Phase II Team and Fantom Consortium: "Functional Annotation of a Full-Length Mouse CDNA Collection", Nature, MacMillan Journals Ltd., London, GB, 409(6821): 685-690 (2001).
Keith, C.T. and Schreiber, S.L., Science 270 (5233): 50-1 (abstract).
Dennis, P.B., et al., "Mammalian TOR: A Homeostatic ATP Sensor," Science, 294:1102-1105 (2001).
Schmeizie, T., et al., "TOR, a Central Controller of Cell Growth," Cell, 103:253-262 (2000).
Nojima, H., et al., "The Mammalian Target of Rapamycin (mTOR) Partner, Raptor, Binds the mTOR Substrates p70 S6 Kinase and 4E-BP1 through Their TOR Signaling (TOS) Motif," Journal of Biological Chemistry, 278(18):15461-15464 (2003).
Liu, Z., et al., "RTG-dependent mitochondria to nucleus signaling is negatively regulated by the seven WD-repeat protein Lst8p," The EMBO Journal, 20(24):7209-7219 (2001).
Chen, J., et al., "Identification of an 11-kDa FKBP12-rapamycin-binding domain within the 289-kDa FKBP12-rapamycin-associated protein and characterization of a critical serine residue," Proc. Natl. Acad. Sci. USA, 92:4947-4951 (1995).
Ohara et al., "Characterization of Size-Fractionated cDNA Libraries Generated by the in vitra Recombination-Assited Method," *DNA Research*, vol. 9, 47-57 (2002).
GenCore version 5.1.6 search for the SEQ ID No. 2 (p. 1, 17-19).
GenCore version 5.1.6 search for the SEQ ID No. 3 (p. 1, 5, and 6).

* cited by examiner

E

Figure 5a p200 mRNA sequence (i.e. includes UTRs and ORF)
AGCGGGTTGTGACTGAATCCCGTCAATATGGCGGCGGATCGGCCGGCCGCTCTCTGAAGAACCTCCGAGTACGAGGGCG
GAATGACAGCGGCGAGGAGAACGTCCCGCTGATCTGACCCGAGAACCTTCTGATAACTTAAGAGAGATTCTCAAAATG
TGCCAGATTGCAGGGAGTATCAAATATGAGAAAGCTAGGCCATCTGAATAACTTTACTAAGCTTCTTTGTGATATTGGC
CACAGTGAAGAAAAACTGGGCTTTCACTATGAGGATATCATAATTTGTTTGCGGTTAGCTTTATTAAATGAAGCAAAGA
AGTGCGAGCAGCAGGGCTACGAGCGCTTCGATATCTCATCCAAGACTCCAGTATTCTCCAGAAGGTGCTAAAATGAAAG
TGGACTATTTAATAGCTAGGTGCATTGACATACAACAGAGCAACGAGGTAGAGAGGACACAAGCACTTCGATTAGTCAGA
AAGATGATTACTGTGAATGCTTCCTTGTTTCCTAGTTCTGTGACCAACTCATTAATTGCAGTTGGAAATGATGACTTCA
AGAAAGACAGAAATGGTCCGAGCATGCATTGAAAAATGTGATTGCCATTATCTGTGAACTAGCACTTCAGAATCCAGGCCCTAATTACTACAATT
GAGGAGGACTAAACACCATATTGAATAAATGTCGGCAGTATGTGCGAGCTGATGTAGAATTAGAGSGAATTTTAGCACCCTATAC
TTGCACCTTCTTAATCATCCAAAGACTCGGCAGTACAGCTGAAGGAGACAGCTCAAAGGAAGACAGAGAAGCACGATTTCTAGCCAGTA
TGATTTTCACTACAGACATAGTCCAGATACAGCTGAAGGAGAAATCTGGAAATTCTGGATCCAGTCT
AAATGGAATCATAGCAACATTCCGATCATGGCAGGTCTACTTGAAGTGCTTTATGATATATTTCGTCTTCC
CTAATAGGAGTACTTTGCATACCAAATATGGAAATAAGGCGAGGTCTACTTGAAGATCCAGGAGGTTCCAAGACAGTTGGAGGCTTT
TCTACCTGTTGTGACTGAGGAGTTCATAGAAGCACTACTCAGTGTAGATCCAGGCCAGATCCAGAGACCTCATGGATAATTAT
CAGATGGCTTTGTGCAGCTGAGGCAAAAACTATTCTTCCTCATCGTGCCAGATCGCGAAGTGATAACAAACAGTGATGATCA
TTGGCACTCAGTCTCTCTGCAGCTACCATCCTTTTAGGAGAGCTTTTACATATGGACATCTTTGAATATCCCAAGGAAAAAGAGACTGCGAGCCAGTGCA
TATCTCAGTTAGAGCTACCATCCTTTTAGGAGAGCTTTGCATCCTTTGATATCCCAAGCCTTATAGTCTTCATTTAGACCACATTAT
ATTTACACTGCTTGCCAACCCTAGCTTCCATGAAATGAATATGGCTGCATCCTTTGATATCCCAAGCCTTATAGTCTTCATTTAGACCACATTAT
GCCTTGAACTGTTTAAAACGCTTCCATGAAATGAAGAAACGAGACCTAAGCCTTATAGTCTTCATTTAGACCACATTAT
TCAGAAAGCAATTGCAACACCAGAAACGGGATCAGTATCTCCGAGTTCAGAACATAAAGAGAATCTTGAATGGAATCTTATA
AGGAAGCTCTTTTAATTAACCTTAGAGATAGCCAAGTCCTTCAACATAAAGATGAACAGTTACACAGGTTGTACGAAGACTACT
GGGACCATTCTTAAGTGGCCAAATGTAAATTATATGCCAACCTGGATTTGCCAAGGCCAAACAGCTCACGGTTGTAG
TTATTTTACAAGCCCAGCAGAATTTCTTCTTGAATCTGAATGAGAGAAGTCTTAGAAGATCTAGTAAAGGATATTGTT
GTTGCCAGTTTACAGAATTTCTTCTTGAATCTGAATGAGAGAAGTCTTAGAAGATCTAGTAAAGGATATTGTT
CAGTGGCTCAATGCTTCATCTGAATGAAACTTTCTTGCCACCCTCATGAGTTAAAATAATGCTGGAAAAATGCAGTGTATTTCAGTGTC
CTACTTTTTATTTATTGGAACACTTTCTTGCCAAGATCACTTGCTAAAACTTACTGTTTCTAGCTTGGACTATAGCAGAGATGGA
TCCTTAATCTTTGCTCCTTGAAAAAGATCACTTGCTAAAACTTACTGTTTCTAGCTTGGACTATAGCAGAGATGGA
TTGGCTAGAGTCATCCTTTCCAAATTTTAACTGCAGCTCTATGCAGACTCTATGCAACAAAAACATTTAAGGGT

Figure 5b

```
ATTATTGAGAGCTAATGTTGAATTCTTTAATAATTGGGGAATTGAGTTGTTAGTGACCCAGCTACACATGATAAAAACAAAA
CGATTCCCTCTGAAGCTCTTGATATCCTCGATGAAGCATGTGAAGACAAGGCCAATCTTCATGCTCTCATTCAGATGAAA
CCAGCGTTATCCCACCTTGGAGACAAGGGTTTGCTTCTCCCTGCTGAGATTTCTCTCCATTCCAAAAGGATTTTCCTATCT
GAATGAAAGAGGTTATGTAGCACTTACTACTTACCGGAAGCACAAAACAATTGAAAAGTGGCACAGGGAATACAACTCCAAATATGTTGACTTGATTGAGG
AACAACTCAATGAAGCACTTACTACTTACCGGAAGCCCTTATGGACAACTAGTACACCATAAAACAGGCTGCCATTTGTTGGAAGT
CAGCGTCCTCACGTCTACCTGCCTATACAGAACTCTGTCGTAATGTTCGTACACCAGATTTCGATAAGTGGGAAGAAATTAAAAAACTGAAAG
ACAGAATATTATTACAGAACTCTGTCGTAATGTTCGTACACCAGATTTCGATAAGTGGGCTCTCAATTGCTACAGAGAAAACGTGATTCCAGAT
CATCTCTTTGGGCCTTGCAAAAACAGTGTGAAGTTCTTTCCATCAGAGGACCTGTGTATATGTACTTGGGCTCTATAGCTAAAAC
ATACTAAAACTTGCAAAAACAGTGTGATATTCTAAATGTCACAACTGGGATGCTGTGAGGCATAGTCGCAAACATCTGTGCCCAGTGGTTC
CAAACAAGGCTGTGATATTCTAAATGTCACAACTGGGATGCTGTGAGGCATAGTCGCAAACATCTGTGCCAGTCAACCAGCTCT
CAGATGATGTGGAACAACTCTGTAATGAACTTTCATCTATCCCAAGCACTCTAAGTTGAACTCGGAGATGACCGGTTTGGCAGCAGCTCTACTAG
AGACATAATAGTGAAAGTGAATCTGTGCCATCGAGTATGTTCATATTGGAGGATGACTCTGACCCATAAAGGATAAAAATTCAT
TACATTTTCCTTGATATCAATGAAGATACAGAGCCAACATTTTATGACCGATCTGACCTTACTTTGCCTAACAAAAACATCGTAGT
TCCCTTTCTTTGCTTCTAGTAAACTTGTGAAGAATCTGAAAGTATCATCTGAAAGTAAGACAAGCTATCTTAAATTCGCTTACTTTGCCTAACAAAACATCGTAGT
AGCAGTGATCCAAAAGGAGGAAATTATCATCCACCCATATCCACTGTACAGAGAAATGACTTAAAATTCACCAAGAATTTTGGTACA
TGTTGATTTTAATCATAGTGATGATTTTACACCCATATCCACTGTACAGAGAAATGACTTAAAATTCACCAAGAATTTTGGTACA
GGAATAAGCACATTGAAGACACTGGTAGTACACCAAGCATTGGAGTAGAGAAAGTTCAACGAGCTCACATATGAAGATACGTAGCCA
GAGAATCACAGAGAAATACAAGCCGAGAGAGTTAGTAGTACAAGTGGCATAAGTTCAATGAACTCAAGTCCTTCACGAGAGACAGTAGTGTAGATG
AAGTTCAATACAGACACTACAAGTGGCATAAGTGGGAAGCATGAGTACTGTGGTAAGTACTAAAACTATTAAGACAAGCCACTATTTGACG
CTACAACTCTAACCATCGTCTCTCCAAATCAAATTCGGTGTCCCTGGTCCTCCAGATTGTAACTTTTAGTTACACAAGTTCTA
CCACAGTCTAACCATCGTCTCTCCAAATCAAATTCGGTGTCCCTGGTCCTCCAGATTGTAACTTTTAGTTACACAAGTTCTA
AAGAGCACAGTCCCTAAAGCACCCCTTATTGCTACAAAGACTACAGCAACCATCACCATGAAGGCCAACAGTTTTGAGTCCAGATTAACATCCTGCAAC
GAGATGCTTTTGGCTATGCTACACTGGCTATTATCATCATTAGATCATTAGAAGAAGATTATTGAGTCCTATTAATCAAAATACCCTGCAAC
GCATCTCCAGCAAAAGATGCTTAAGTTATGCATCATTAGATCATTAGAAGAAGATTATTGAGTCCTATTAATCAAAATACCCTGCAAC
CAGGTTCATGAAAGCCTTAAGTTATGCATCATTAGATCATTAGAAGAAGATTATTGAGTCCTATTAATCAAAATACCCTGCAAC
GATCTTCCTCAGTGCGTCCATGGTCCTCCAGTGTCCAGTGTAAAGGATATTCCCTATTTCAGACAAAAACATACCACACATGATCGAGGTG
GATATAAATGATATATTCCAGGTCAGGAGGTCTTCCCATCTGGAACTGGAGGTCTTCTCTGTTTTTAGAAAGTACAGAAGACACTGGA
AAGAGCATTGCCCATGATGCAGGAGGTCTTCCCATCTGGAACTGGAGGTCTTCTCTGTTTTTAGAAAGTACAGAAGACACTGGA
AGCAGATGAGTCTTACGGAAATAACTGCCTTTATTGTCTGTATTGAAATTCGGGTTTCCAGCCCAGCAACCAACTGAG
CTACAGGAACATACAGATGATAACTTTCAAGATATTCCATATTCTGATTGGTGTGAGCAGACTATCCATAATCCTTTAGAAG
TGCAATATGTAGTCATTCAGACTTTCAAGATATTCCATATTCTGATTGGTGTGAGCAGACTATCCATAATCCTTTAGAAG
TGGTTCCCCTCTAAGTTTTCGGGATTTCTGATGCAGTGATGGGGTCTCAAGAAGGTCTCCAGCAGCTAGCAGCAGCCAAAAGC
```

Figure 5c

ACAGAATTGTTACTAGGTGTTAAAACAATTCCAGATGATACACCAATGTGCCGTATACTCCTTCGCAAAGAAGTTCTAAG
ATTAGTCATTAATTGAGTAGTTCAGTTTCAACTAAATGTCATGAGACTGGGCTTTTAACAATTAAGGAGAAGTATCCTC
AAACATTTGATGACATATGCCTTTACTCTGAGGTTTCCCATTTGCTGTCACACTGCACATTCAGACTTCCGTCGGAGG
TTCATACAAGAATTATTCAAGATGTACAGTTTCTACAAATGCATGAAGAAGCAGAGGCTGTGTTGGCAACACCACCAAA
GCAACCTATAGTTGATACATCTGCTGAATCCTGACCCTCATATTTATGATGATATAGATACATATATATATATTCATAT
TTGTGGATTTCCTAAAAGCCTCAGAAAAATACGACTAGGCAGCAAAGACAGGAGTATCTTCTGTACACTGTTCCGCA
GTTACTGGTACATGAACAGTTGGAACTGCTGACTTTCCTAACCAAAACAACTTCCTTCTCCTTGTTGAGCCTTTTGA
GGGGTTCATGATTCATTACCACAGTTTTAAGAGTTTCAGTTACCATTGTATGCAAGAGCCAAGCACTGAATACCTACATA
GGTTTCTATTTCTTCATTTTAAAAGCGTAAATGACAGTGGAACAATAATGGATATGCAGAAGCACCCTTCACAAGTT
ATTTCTGAATGATTTAGGGTAAATAATACAGATGCCTTGTATGTTAACTAACTTGTGAAAGCAGGAATCAGTGTCTCT
AAGGCTGCATCCTATTACCACAATGGGGTTGTGCTATAACTGGCTGGTATTAGAGAGGAAC

Figure 6a p200 ORF sequence (i.e., no UTRs)
ATGGCGGCGATCGGCCGCGGCCGCTCTCTGAAGAACCTCGAGTACGAGGGCGAATGACAGCGGCGAGGAGAACGTCCC
GCTGGATCTGACCCGAGAACCTTCTGATAACTTAAGAGAGATTCTCCAAATGTGGCCAGATTGCAGGGAGTATCAAATA
TGAGAAAGCTAGGCCATCTGAATAACTTTACTAAGCTTCTTGTGATTATTGGCCACAGTGAAGAAAAACTGGGCTTTCAC
TATGAGGATATCATAATTGTTTGCGGTTAGCTTTATTAAATGAAGCAAAAGAAGTGCGAGCAGCAGGGCTACGAGCGCT
TCGATATCTCATCCAAGACTCCAGTATTCTCCAGAAGGTGCTAAAAATTGAAAGATGATTACTGTGAATGCTTCCTTG
ACATACAACAGAGCAACGAGGTAGAGAGGACACAAGCACTTCGATTAGTCAGAAAGATGATTACTGTGAATGGTCCTTG
TTTCCTAGTTCTGTGACCAACTCATTAATTGCAGTTGGAAATGATGGACTTCAAGAAAGACAGAATGGTCCGAGCATG
CATTGCCATTATCTGTGAACTAGCACTTCAGAATCCAGAGGTGGTGCCCTTCGAGGAGGACTAAACACCATATTGAAAA
ATGTGATTGATTGCCAATTAAGTCGAATAAATGAGGCCCTAATTACTACAAATTTGCACCTTCTTAATCATCCAAAGACT
CGGCAGTATGTGCGAGCTGATGTAGAATTAGAGSGAATTTAGCACCCTATACTGATTTTCACTACAGACATAGTCCAGA
TACAGCTGAAGGACAGCTCAAAGAAGACAGAGAAGACACGATTTCTAGCCAGTAAAATGGAATCATAGCAACATTCGAT
CATGGGCAGGTATTATTAATTTATGTAAACCTGGAAATTCTGGAAATTCTCTAATAGAGTACTTTGCATACCAAAT
ATGGAAATAAGGCGAGTCTACTTGAAGTGCTTTATGATATATTCGTCTCTTCCTCGTTGTGACTGAGGAGTTCAT
AGAAGCACTACTCAGTGTAGATCCAGGGAGGTTCCAAGACGTTCCAGAGGCTTCAGATGGCTTTGTGCAGCTGAGGCAA
AAACTATTCTTCCTCATCGTGCCAGATCCAGCCAGACCTCAGGAATAATTATTGGCACTGATACTCTCTGCATTTATT
CGTAATGGACTTTTAGAGGGTCTAGTGCAAACACAATTCTTCCTCATTCACATAGCCATCATTTACACTGCTTGCCAACCCTAATGA
AGGAGAGCTTTTACATATGGCAAACACAATTCTTCCTCATTCACATAGCCATCATTTACACTGCTTGCCAACCCTAATGA
ATATGGCTGCATCCTTTGATATCCCAAGGAAAAAGAGACTGCGAGCCAGTGACCTTGAGCCTTGTTTAAAACGCTTCCAT
GAAATGAAGAAACGAGGAACCTAAGCCTTATAGTCTTCATTTAGACCACCATTATTCAGAAAGCAATTGCAACACACCAGAA

ACTGATACCATCACCATGAAGGCCAACAGTTTTGAGTCCAGATTAACACCAAGCAGTTCATGAAAGCCTTAAGTTATGC
ATCATTAGATAAAGAAGATTTATTGAGTCCTATTAATCAAAATACCCTGCAACGATCTTCCTCAGTGCCGGTCCATGGTGT
CCAGTGCCACATATGGGGGTTCAGATGATTACATTGGTCTTGCTCTCCCGGTGGATATAAATGATATATTCCAGGTAAAG
GATATTCCCTATTTTCAGACAAAAAACATACCACCACATGATGAGTGCAAGAGCATTGCCCATGATGCAGGAGG
TCTTCCATCTGGAACTGGAGGTCTTGTAAAAAATTCTTTTCACTTGCTACGACAGCAGATGAGTCTTACGGAAATAATGA
ATTCAATCATTCAGATGCCTCTCTGTTTTTAGAAAGTACAGAAGACACTGGACTACAGGAACATACAGATGATAACTGC
CTTTATTGTGTCTGTATTGAAATTCTGGGTTTCCAGCCCAGCAACCAACTGAGTGCAATATGTAGTCATTCAGACTTTCA
AGATATTCCATATTCTGATTGGTGTGAGCAGACTATCCATAATCCTTTAGAAGTGGTTCCCTCTAAGTTTTCGGGGATTT
CTGGATGCAGTGATGGGGTCTCAAGAAGGCTCAGCTAGCACCAGAAGCACAGAATTGTTACTAGGTGTTAAAACA
ATTCCAGATGATACACCAATGCCGTATACTCCCTTCGCAAAGAAGTTCTAAGATTAGTCATTAATTTGATGACATATGCCTTTACT
TTCAACTAAATGTCATGAGACTGGGCTTGTCACACTGCACATTCAGACTTCCGTGTCGGAGGTTCATACAAGAATTATTTCAAGATGTA
CTGAGGTTTCCCATTTGCTGTGACACTGCACATTCAGACTTCCGTGTCGGAGGTTCATACAAGAATTATTTCAAGATGTA
CAGTTTCTACAAATGCATGAAGAGCAGAGGCTGTGTTGGCAACACCAAAGCAACCTATAGTTGATACATCTGCTGA
ATCCTGA

Figure 7a p200 amino acid sequence
MAAIGRGRSLKNLRVRGRNDSGEENVPLDLTREPSDNLREILQNVARLQGVSNMRKLGHLNNFTKLLCDIGHSEEKLGFH
YEDIIICLRLALLNEAKEVRAAGLRALRYLIQDSSILQKVLKLKVDYLIARCIDIQQSNEVERTQALRLVRKMITVNASL
FPSSVTNSLIAVGNDGLQERDRMVRACIAIICELALQNPEVVALRGGLNTILKNVIDCQLSRINEALITTILHLLNHPKT
RQYVRADVELEXILAPYTDFHYRHSPDTAEGQLKEDREARFLASKMGIIATFRSWAGIINLCKPGNSGIQSLIGVLCIPN
MEIRRGLLEVLYDIFRLPLPVVTEEFIEALLSVDPGRFQDSWRLSDGFVAAEAKTILPHRARSRPDLMDNYLALILSAFI
RNGLLEGLVEVITNSDDHISVRATILLGELLHMANTILPHSHSHHLHCLPTLMNMAASFDIPKEKRLRASAALNCLKRFH
EMKKRGPKPYSLHLDHIIQKAIATHQKRDQYLRVQKDIFILKDTEEALLINLRDSQVLQHKENLEWNWNLIGTILKWPNV
NLRNYKDEQLHRFVRRLLYFYKPSSKLYANLDLDFAKAKQLTVVGCQFTEFLLESEEDGQGYLEDLVKDIVQWLNASSGM
KPERSLQNNGLLTTLSQHYFLFIGTLSCHPHGVKMLEKCSVFQCLLNLCSLKNQDHLLKLTVSSLDYSRDGLARVILSKI
LTAATDACRLYATKHLRVLLRANVEFFNNWGIELLVTQLHDKNKTISSEALDILDEACEDKANLHALIQMKPALSHLGDK
GLLLLRFLSIPKGFSYLNERGYVAKQLEKWHREYNSKYVDLIEEQLNEALTTYRKPVDGDNYVRRSNQRLQRPHVYLPI
HLYGQLVHHKTGCHLLEVQNIITELCRNVRTPDLDKWEEIKKLKASLMALGNIGSSNWGLNLLQEENVIPDILKLAKQCE
VLSIRGTCVYVLGLIAKTKQGCDILKCHNWDAVRHSRKHLWPVVPDDVEQLCNELSSIPSTLSNSESTSSRHNSESESV
PSSMFILEDDRFGSSSTSTFFLDINEDTEPTFYDRSGPIKDKNSFPFFASSKLVKNRILNSLTLPNKKHRSSSDPKGGKL
SSESKTSNRRIRTLTEPSVDFNHSDDFTPISTVQKTLQLETSFMGNKHIEDTGSTPSIGENDLKFTKNFGTENHRENTSR
ERLVVESSTSSHMKIRSQSFNTDTTTSGISSMSSSPSRETVGVDATTMDTDCGSMSTVVSTKTIKTSHYLTPQSNHLSLS

Figure 7b

KSNSVSLVPPGSSHTLPRRAQSLKAPSIATIKSLADCNFSYTSSRDAFGYATLKRLQQQRMHPSLSHSEALASPAKDVLF
TDTITMKANSFESRLTPSRFMKALSYASLDKEDLLSPINQNTLQRSSSVRSMVSSATYGGSDDYIGLALPVDINDIFQVK
DIPYFQTKNIPPHDDRGARAFAHDAGGLPSGTGGLVKNSFHLLRQQMSLTEIMNSIHSDASLFLESTEDTGLQEHTDDNC
LYCVCIEILGFQPSNQLSAICSHSDFQDIPYSDWCEQTIHNPLEVVPSKFSGISGCSDGVSQEGSASSTKSTELLLGVKT
IPDDTPMCRILLRKEVLRLVINLSSSVSTKCHETGLLTIKEKYPQTFDDICLYSEVSHLLSHCTFRLPCRRFIQELFQDV
QFLQMHEEAEAVLATPPKQPIVDTSAES.

Figure 8

GβL mRNA sequence (i.e. includes UTRs and ORF) (accession # BC017119)

GTGCCGGAGCCGCCCCCGTAAGATGCTTCTGACCTTTGACCCTGCCGTTCAGCTCTAGGGCCCGTCCAGGCCACCATGAACA
CCTCCCAGGCACGGTGGGCAGTGACCCGGTCATCCTGCCACTGCCAGGCTACGACCACACCGTGCGCTTCTTGGCAGGCC
CACAGCGGCATCTGCACCCGGACGGTGCAGCACCCAGAGGACTCCCAGGTGAATGCCTTGGAGGTCACACCGGACCGCAGCAT
GATTGCTGCTGCAGGTTACCAGCACACATCCGCATGTATGATCTCAACTCCAATAACCCTAACCCATCATCAGCTACGACG
GCGTCAACAAGAAACATCGCGTCTGTGGGCTTCCACGAAGACGGCCGCTGGATGTACACGGGCGGCGAGGACTGCACAGCC
AGGATCTGGGACCTCAGTTCCCGGAACCTGCCAGTGCCAGCGGATCTTCCAGGTGAACGCACCCATTAACTGCGTGTGCCT
GCACCCGAACCAGGCAGAGCTCATCGTGGGTGACCAGAGCGGGGCTTATCCACATCTGGGACTTGAAAACAGACCACAACG
AGCAGCTGATCCCTGAGCCCGAGGTCTCCATCACGTCCGCCCACATCGATCCCGACGCCAGCTACTCATCCCAAGACTAAT
AGCACCGGAAACTGCTATGTCTGGAATCTGACGGGGGCATTGGTGACGAGGTGACCTCCACCTGCTCGCTCGCTGATCAGA
CCCTGCCCACACGCGCTACGCCCTGTCGCTTCAGCCCTGATGTGTCGACTCCAACTTCTCTCCCTGGGGACTCCAGTATACATCGTCAGCTGCCCA
CGTGCAAGATCTGGAGGACGTCCAACTTCTCCCCTGGGGACTCCAGTATACATCGTCAGCTTCACTGTGAGCCCTGCCTGGCC
CGCGGCTGATGTGGGCCCCGGCTGCTGCCCCTGCAGCCAGCCAGTTCCCCTCGCTGCCCCCTCGCGTGGGCGCCTGCTTGCC
TCCCTGGCCCCCCGCCCCTGCGCTCTTAGCCCTGCACAATCTCCCCCCAGCTTCCTCCGACAACCTGGCCCCGGCTCTGTTGGTGTGGAGAC
TGCACCTGCCTCTTAGCCCTGCACAATCTCCCCCCAGCTTCCTCCGACAACCTGGCCCCGGCTCTGTTGGTGTGGGCTAGC
TGGAGAGATCAAGAGAGAGTATGGCGGCCACCAGAAGGCTGTTGTCTGCCTGGCCTTCAATGACAGTGTGCTGGGCTAGC
CTGTGACCCCTCGGGACTGGTGGTCCTGAGCTGCAGTGCAGGGACCCATGCAGCACCCAGGTCAGCAGCAGAGCAGACCCTC
CCCTGCCGGCCTGCCCAGCTGACCTGATGGCCCGCCCCCCGTCTGGGCCGCAGGCTGCCTGGGACTCTC
AGCCCCCAGTTGCTTATCCAGATGTGACAGAGCTGCACACTCCTGACCTGCACACTCTGGACTGGGCTAGCCTGCACT
GCCTGGGAAAGTCGGCCCGAGGGCCCAAAGCTGGCCCACCCAGCCAGGTGAAGGGTTTATTAGTCCC
CCCTCCCTGCCGCGTTTCAGGGCCTGCAGGTGCAGGTGGGACGGGCCAGGCCAGGCCCAGGTCGGG
TGCCAGCAGCTGTCTCCCTGGTGCAGGTGCCTGCAGGTGATTGGGACGGGCCAGGCTGGGCCAGGTCGGG
GGCTCAGTCTGGGAGGTAATAAAGCGACACGCAGATGTTGCTCGGGAAAAAAAAAAAAAAAAAAAACCA
AAAAAAAAAAAAAAAAAAAAAAAAAAAAAAAAAAAAAAAAAAAAAAAAAAAAA

Figure 9a

GβL ORF sequence (i.e., no UTRs) (derived from accession # BC017119)
ATGAACACCTCCCCAGGCACGGTGGGCACGGCAGTGACCCGGTCATCCTGGCCACTGCAGGCTACGACCACCACCGTGCGCTTCTG
GCAGGCCCACAGCGGCCATCTGCACCCGGACGGTGCAGCACCAGGACTCCCCAGGTGAATGCCTTGGAGGTCACACCGGACC
GCAGCATGATTGCTGCTGCAGGTTACCAGCACACATCCGCATGTATGATCTCAACTCCAATAACCCTAACCCTAACCCCTAATAACCCTAACCCTAATCAGC
GCAGCATGATTGCTGCTGCAGGTTACCAGCACACATCCGCATGTATGATCTCAACTCCAATAACCCTAACCCCATCATCAGC

Figure 9b

TACGACGGGCGTCAACAAGAACATCGCGTCTGTGGGCTTCCACGAAGACGGCCGCTGGATGTACACGGGGCGGCGAGGACTG
CACAGCCAGGATCTGGGACCTCAGGTCCCGGAACCTGCCAGTGCCAGCGGATCTTCCAGTGAACGCACCCATTAACTGCG
TGTGCCTGCACCCGAACCAGGCAGAGCTCATCGTGGGTGACCAGAGCGGGGCTATCCACATCTGGGACTTGAAAACAGAC
CACAACGAGCAGCAGTCCCTGAGCCCTGAGCGTCTCCATCACGTCCGCCACATCGATCCGACGCCAGTCAGCTACATGGCAGC
TGTCAATAGCACCGGAAACTGCTATGTCTGGAATCTGACGGGGGCATTGGTGACGAGTGACCCAGCTCATCCCCAAGA
CTAAGATCCCTGCCCACACGCTACGCCCTGCAGTGTCGCTTCAGCCCCGACTCCAGCCTCCTGCCCACCTGCTCGGCT
GATCAGACGTGCAAGATCTGGAGGACGTCCAACTTCTCCCTGATGACGGAGCTGAGCATCAAGAGCGGCAACCCGGGGA
GTCCTCCCGCGCTGGATGTGGGGCTGCGCCTTTCTCGGGGACTCCCAGTACATCGTCACTGCTTCCTCGGACAACCTGG
CCCGGCTCTGGTGTGTGGAGACTGGAGAGATCAAGAGAGTATGGCGGCCACCAGAAGGCTGTTGTCTGCCTGGCCTTC
AATGACAGTGTGCTGGGCTAG

Figure 10

GβL amino acid sequence (accession # AAH17119)
MNTSPGTVGSDPVILATAGYDHTVRFWQAHSGICTRTVQHQDSQVNALEVTPDRSMIAAAGYQHIRMYDLNSNNPNPIIS
YDGVNKNIASVGFHEDGRWMYTGGEDCTARIWDLRSRNLQCQRIFQVNAPINCVCLHPNQAELIVGDQSGAIHIWDLKTD
HNEQLIPEPEVSITSAHIDPDASYMAAVNSTGNCYVWNLTGGIGDEVTQLIPKTKIPAHTRYALQCRFSPDSTLLATCSA
DQTCKIWRTSNFSLMTELSIKSGNPGESSRGWMWGCAFSGDSQYIVTGEPRPGLPHPWPPALASRASPPRLQLPLCWGRL
LGLHLRS.

Figure 14
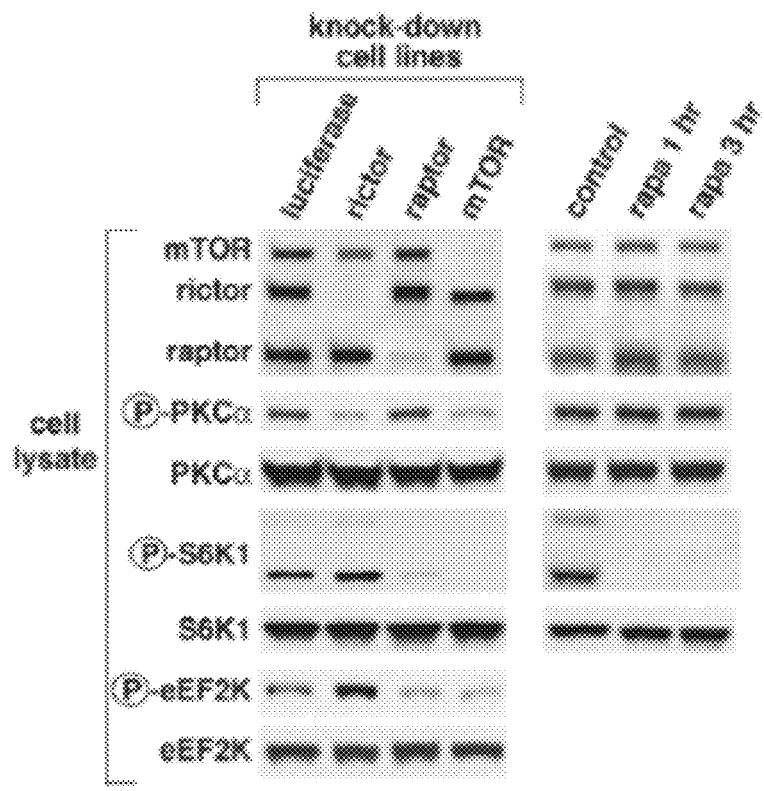
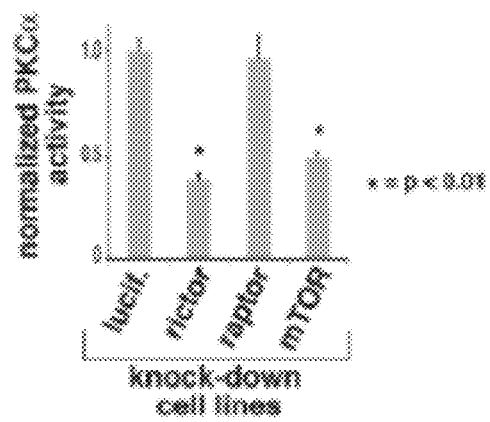
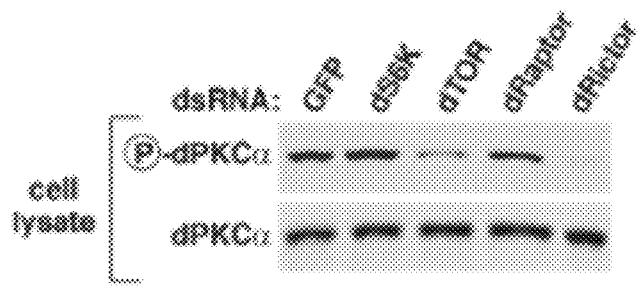

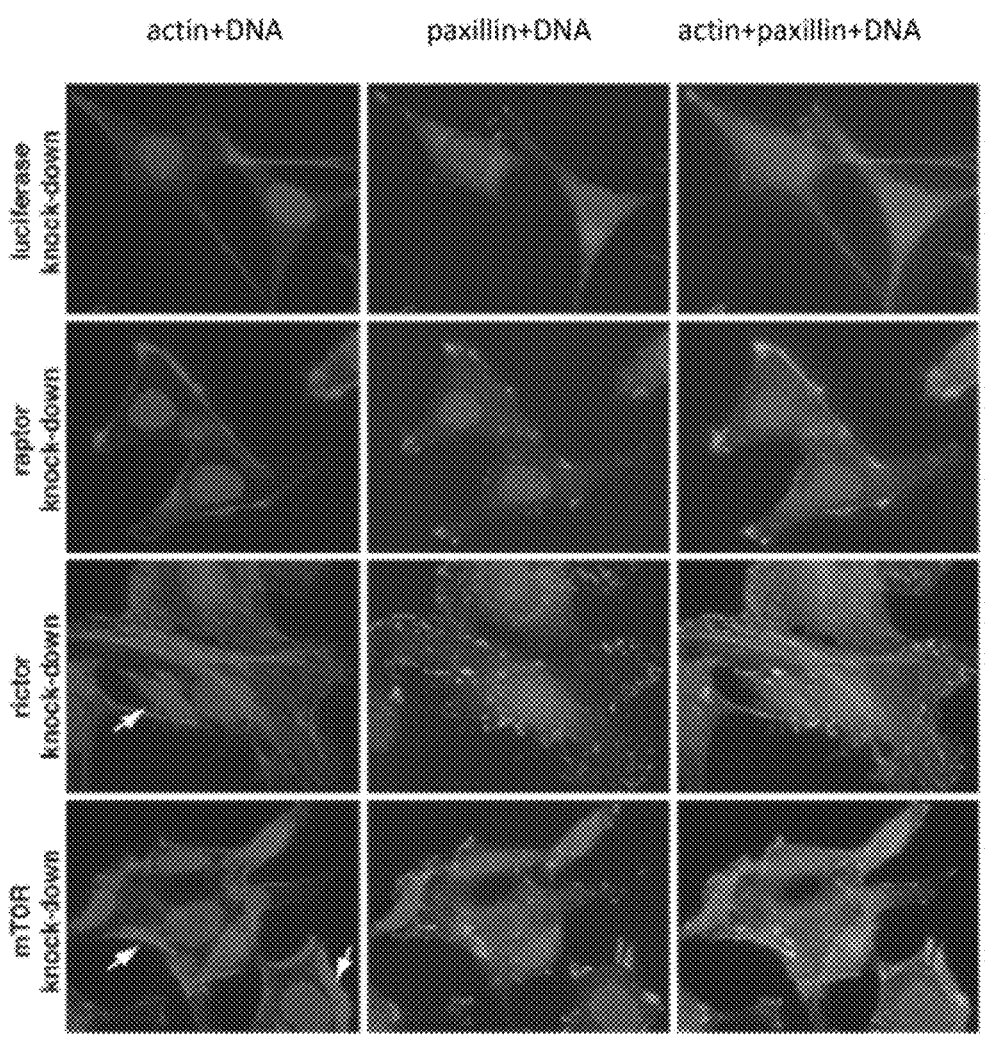

actin
+
DNA

Figure 17
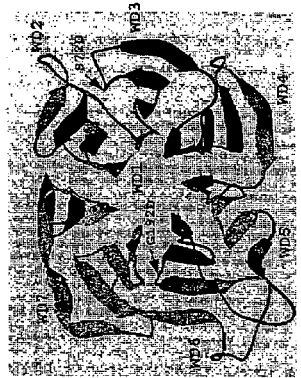
Figure 18
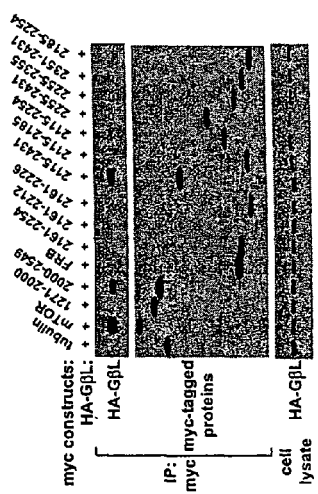
Figure 19

SEQUENCE LISTING

<160> NUMBER OF SEQ ID NOS: 52

<210> SEQ ID NO 1
<211> LENGTH: 5662
<212> TYPE: DNA
<213> ORGANISM: Homo sapiens

<400> SEQUENCE: 1
agcgggttgt gactgaaacc cgtcaatatg gcggcgatcg gccgcggccg ctctctgaag    60

```
aacctccgag tacgagggcg gaatgacagc ggcgaggaga acgtcccgct ggatctgacc    120
cgagaacctt ctgataactt aagagagatt ctccaaaatg tggccagatt gcagggagta    180
tcaaatatga gaaagctagg ccatctgaat aactttacta agcttctttg tgatattggc    240
cacagtgaag aaaaactggg cttcactat gaggatatca taatttgttt gcggttagct     300
ttattaaatg aagcaaaaga agtgcgagca gcagggctac gagcgcttcg atatctcatc    360
caagactcca gtattctcca gaaggtgcta aaattgaaag tggactattt aatagctagg    420
tgcattgaca tacaacagag caacgaggta gagaggacac aagcacttcg attagtcaga    480
aagatgatta ctgtgaatgc ttccttgttt cctagttctg tgaccaactc attaattgca    540
gttggaaatg atggacttca agaaagagac agaatggtcc gagcatgcat tgccattatc    600
tgtgaactag cacttcagaa tccagaggtg gtggcccttc gaggaggact aaacaccata    660
ttgaaaaatg tgattgattg ccaattaagt cgaataaatg aggccctaat tactacaatt    720
ttgcaccttc ttaatcatcc aaagactcgg cagtatgtgc gagctgatgt agaattagag    780
agaattttag caccctatac tgattttcac tacagacata gtccagatac agctgaagga    840
cagctcaaag aagacagaga agcacgattt ctagccagta aaatgggaat catagcaaca    900
ttccgatcat gggcaggtat tattaattta tgtaaacctg gaaattctgg gatccagtct    960
ctaataggag tactttgcat accaaatatg gaaataaggc gaggtctact tgaagtgctt    1020
tatgatatat ttcgtcttcc tctacctgtt gtgactgagg agttcataga agcactactc    1080
agtgtagatc cagggaggtt ccaagacagt tggaggcttt cagatggctt tgtggcagct    1140
gaggcaaaaa ctattcttcc tcatcgtgcc agatccaggc cagacctcat ggataattat    1200
ttggcactga tactctctgc atttattcgt aatggacttt tagagggtct agttgaagtg    1260
ataacaaaca gtgatgatca tatctcagtt agagctacca tccttttagg agagctttta    1320
catatggcaa acacaattct tcctcattca catagccatc atttcactg cttgccaacc     1380 ctaatgaata tggctgcatc ctttgatatc cccaaggaaa agagactgcg agccagtgca    1440
gccttgaact gttaaaaacg cttccatgaa atgaagaaac gaggacctaa gccttatagt    1500
cttcatttag accacattat tcagaaagca attgcaacac accagaaacg ggatcagtat    1560
ctccgagttc agaaagatat atttatcctt aaggatacag aggaagctct tttaattaac    1620
cttagagata gccaagtcct tcaacataaa gagaatcttg aatggaattg aatcttata    1680 gggaccattc ttaagtggcc aaatgtaaat ctaagaaact ataaagatga acagttacac    1740
aggtttgtac gaagactact ttatttttac aagcccagca gtaaattata tgccaacctg    1800
gatctggatt ttgccaaggc caaacagctc acggttgtag gttgccagtt tacagaattt    1860
cttcttgaat ctgaagagga tgggcaaggc tacttagaag atctagtaaa ggatattgtt    1920
cagtggctca atgcttcatc tggaatgaaa cccgaaagaa gtcttcaaaa taatggttta    1980
ttgaccaccc ttagtcaaca ctacttttta tttattggaa cactttcttg ccaccctcat    2040
ggagttaaaa tgctggaaaa atgcagtgta tttcagtgtc tccttaatct ttgctccttg    2100
aaaaaccaag atcacttgct aaaacttact gtttctagct tggactatag cagagatgga    2160
ttggctagag tcatcctttc caaaatttta actgcagcta ctgatgcctg cagactctat    2220
gcaacaaaac atttaagggt attattgaga gctaatgttg aattctttaa taattgggga    2280
attgagttgt tagtgaccca gctacatgat aaaaacaaaa cgatttcctc tgaagctctt    2340
gatatcctcg atgaagcatg tgaagacaag gccaatcttc atgctctcat tcagatgaaa    2400
ccagcgttat cccaccttgg agacaagggt ttgcttctcc tgctgagatt tctctccatt    2460
```

```
ccaaaaggat tttcctatct gaatgaaaga ggttatgtag caaaacaatt ggaaaagtgg    2520
cacagggaat acaactccaa atatgttgac ttgattgagg aacaactcaa tgaagcactt    2580
actacttacc ggaagcctgt tgatggtgat aactatgttc gtcggagtaa ccaaagatta    2640
cagcgtcctc acgtctacct gcctatacac ctttatggac aactagtaca ccataaaaca    2700
ggctgccatt tgttggaagt acagaatatt attacagaac tctgtcgtaa tgttcgtaca    2760
ccagatttgg ataagtggga agaaattaaa aaactgaaag catctctttg ggccttggga    2820
aatatcggct catcaaattg gggtctcaat ttgctacagg aagaaaacgt gattccagat    2880
atactaaaac ttgcaaaaca gtgtgaagtt cttttccatca gagggacctg tgtatatgta    2940
cttgggctca tagctaaaac caaacaaggc tgtgatattc taaaatgtca caactgggat    3000
gctgtgaggc atagtcgcaa acatctgtgg ccagtggttc cagatgatgt ggaacaactc    3060
tgtaatgaac tttcatctat cccaagcact ctaagtttga actcggagtc aaccagctct    3120
agacataata gtgaaagtga atctgtgcca tcgagtatgt tcatattgga ggatgaccgg    3180
tttggcagca gctctactag tacatttttc cttgatatca atgaagatac agagccaaca    3240
ttttatgacc gatctggacc cataaaggat aaaaattcat tccctttctt tgcttctagt    3300
aaacttgtga agaatcgtat cttaaattcg cttactttgc ctaacaaaaa acatcgtagt    3360
agcagtgatc caaaggagg gaaattatca tctgaaagta agacaagcaa caggcgaatc    3420
agaacactta cggagcccag tgttgatttt aatcatagtg atgattttac acccatatcc    3480
actgtacaga aaacattaca attagagact tcatttatgg ggaataagca cattgaagac    3540
actggtagta caccaagcat tggagaaaat gacttaaaat tcaccaagaa tttttggtaca    3600 gagaatcaca gagaaaatac aagccgagag aggttagtag tagaaagttc aacgagctca    3660
catatgaaga tacgtagcca aagtttcaat acagacacta caacaagtgg cataagttca    3720
atgagctcaa gtccttcacg agagacagta ggtgtagatg ctacaactat ggacacagac    3780
tgtggaagca tgagtactgt ggtaagtact aaaaactatta agacaagcca ctatttgacg    3840
ccacagtcta accatctgtc tctctcccaaa tcaaattcgg tgtccctggt gcctccaggt    3900
tcttctcata cgcttcctag aagagcacag tcccttaaag caccctctat tgctacaatt    3960
aaaagtctag cagattgtaa ctttagttac acaagttcta gagatgcttt tggctatgct    4020
acactgaaaa gactacagca acaaagaatg catccatcct tatctcactc tgaagctttg    4080
gcatctccag caaaagatgt gctatttact gataccatca ccatgaaggc caacagtttt    4140
gagtccagat taacaccaag caggttcatg aaagccttaa gttatgcatc attagataaa    4200
gaagatttat tgagtcctat taatcaaaat accctgcaac gatcttcctc agtgcggtcc    4260
atggtgtcca gtgccacata tggggttca gatgattaca ttggtcttgc tctcccggtg    4320
gatataaatg atatattcca ggtaaaggat attccctatt ttcagacaaa aaacatacca    4380
ccacatgatg atcgaggtgc aagagcattt gcccatgatg caggaggtct tccatctgga    4440
actggaggtc ttgtaaaaaa ttcttttcac ttgctacgac agcagatgag tcttacggaa    4500
ataatgaatt caatccattc agatgcctct ctgttttag aaagtacaga agacactgga    4560
ctacaggaac atacagatga taactgcctt tattgtgtct gtattgaaat tctgggtttc    4620
cagcccagca accaactgag tgcaatatgt agtcattcag actttcaaga tattccatat    4680
tctgattggt gtgagcagac tatccataat cctttagaag tggttccctc taagtttttcg    4740 gggatttctg gatgcagtga tggggtgtct caagaaggct cagctagcag caccaaaagc    4800
acagaattgt tactaggtgt taaaacaatt ccagatgata caccaatgtg ccgtatactc    4860
```

```
cttcgcaaag aagttctaag attagtcatt aatttgagta gttcagtttc aactaaatgt    4920
catgagactg ggcttttaac aattaaggag aagtatcctc aaacatttga tgacatatgc    4980
ctttactctg aggtttccca tttgctgtca cactgcacat tcagacttcc gtgtcggagg    5040
ttcatacaag aattatttca agatgtacag tttctacaaa tgcatgaaga agcagaggct    5100
gtgttggcaa caccaccaaa gcaacctata gttgatacat ctgctgaatc ctgacctcat    5160
atttatgatg gatatagata catactatat atattcatat ttgtggattt cctaaaagcc    5220
tcagaaaata cgactgacta ggcagcaaag acaggagtat cttctgtaca ctgttccgca    5280
gttactggta catgaacagt tggaactgct gactttccta accaaaacaa cttccttctc    5340
tcctttgttg agccttttga ggggttcatg attcattacc acagttttaa gagtttcagt    5400
taccattgta tgcaagagcc aagcactgaa tacctacata ggttttctat tttctttcat    5460
tttaaaagcg taatgacagt ggaacaataa tgggatatgc agaagcaccc ttcacaagtt    5520
atttctgaat gattttaggg taaataatac agatgccttg tatgttaact aacttgtgga    5580
aagcaggaat cagtgtctct aaggctgcat cctattacca caatggggtt gtgctataac    5640
tggctggtat tagagaggga ac                                              5662

<210> SEQ ID NO 2
<211> LENGTH: 5127
<212> TYPE: DNA
<213> ORGANISM: Homo sapiens

<400> SEQUENCE: 2
atggcggcga tcggccgcgg ccgctctctg aagaacctcc gagtacgagg gcggaatgac      60
agcggcgagg agaacgtccc gctggatctg acccgagaac cttctgataa cttaagagag     120
attctccaaa atgtggccag attgcaggga gtatcaaata tgagaaagct aggccatctg     180
aataacttta ctaagcttct ttgtgatatt ggccacagtg aagaaaaact gggctttcac     240
tatgaggata tcataatttg tttgcggtta gctttattaa atgaagcaaa agaagtgcga     300
gcagcagggc tacgagcgct tcgatatctc atccaagact ccagtattct ccagaaggtg     360
ctaaaattga aagtggacta tttaatagct aggtgcattg acatacaaca gagcaacgag     420
gtagagagga cacaagcact tcgattagtc agaaagatga ttactgtgaa tgcttccttg     480
tttcctagtt ctgtgaccaa ctcattaatt gcagttggaa atgatggact tcaagaagga     540
gacagaatgg tccgagcatg cattgccatt atctgtgaac tagcacttca gaatccagag     600
gtggtggccc ttgaggagg actaaacacc atattgaaaa atgtgattga ttgccaatta     660
agtcgaataa atgaggccct aattactaca attttgcacc ttcttaatca tccaaagact     720
cggcagtatg tgcgagctga tgtagaatta gagagaattt tagcacccta tactgatttt     780
cactacagac atagtccaga tacagctgaa ggacagctca agaagacag agaagcacga     840 tttctagcca gtaaaatggg aatcatagca acattccgat catgggcagg tattattaat     900
ttatgtaaac ctggaaattc tggatccag tctctaatag gagtactttg cataccaaat      960
atggaaataa ggcgaggtct acttgaagtg ctttatgata tatttcgtct tcctctacct    1020
gttgtgactg aggagttcat agaagcacta ctcagtgtag atccagggag gttccaagac    1080
agttggaggc tttcagatgg cttttgtggca gctgaggcaa aaactattct tcctcatcgt    1140
gccagatcca ggccagacct catggataat tatttggcac tgatactctc tgcatttatt    1200
cgtaatggac tttagagggt ctagttgaa gtgataacaa acagtgatga tcatatctca    1260
gttagagcta ccatcctttt aggagagctt ttacatatgg caaacacaat tcttcctcat    1320
```

```
tcacatagcc atcatttaca ctgcttgcca accctaatga atatggctgc atcctttgat    1380
atccccaagg aaaagagact gcgagccagt gcagccttga actgtttaaa acgcttccat    1440
gaaatgaaga aacgaggacc taagccttat agtcttcatt tagaccacat tattcagaaa    1500
gcaattgcaa cacaccagaa acgggatcag tatctccgag ttcagaaaga tatatttatc    1560
cttaaggata cagaggaagc tcttttaatt aaccttagag atagccaagt ccttcaacat    1620
aaagagaatc ttgaatggaa ttggaatctt atagggacca ttcttaagtg gccaaatgta    1680
aatctaagaa actataaaga tgaacagtta cacaggtttg tacgaagact actttatttt    1740
tacaagccca gcagtaaatt atatgccaac ctggatctgg attttgccaa ggccaaacag    1800
ctcacggttg taggttgcca gtttacagaa tttcttcttg aatctgaaga ggatgggcaa    1860
ggctacttag aagatctagt aaaggatatt gttcagtggc tcaatgcttc atctggaatg    1920
aaacccgaaa gaagtcttca aaataatggt ttattgacca cccttagtca acactacttt    1980
ttatttattg gaacactttc ttgccaccct catggagtta aaatgctgga aaaatgcagt    2040
gtatttcagt gtctccttaa tctttgctcc ttgaaaaacc aagatcactt gctaaaactt    2100
actgtttcta gcttggacta tagcagagat ggattggcta gagtcatcct ttccaaaatt    2160
ttaactgcag ctactgatgc ctgcagactc tatgcaacaa acatttaag ggtattattg    2220 agagctaatt ttgaattctt taataattgg ggaattgagt tgttagtgac ccagctacat    2280
gataaaaaca aaacgatttc ctctgaagct cttgatatcc tcgatgaagc atgtgaagac    2340
aaggccaatc ttcatgctct cattcagatg aaaccagcgt tatcccacct tggagacaag    2400
ggtttgcttc tcctgctgag atttctctcc attccaaaag gattttccta tctgaatgaa    2460
agaggttatg tagcaaaaca attggaaaag tggcacaggg aatacaactc caaatatgtt    2520
gacttgattg aggaacaact caatgaagca cttactactt accggaagcc tgttgatggt    2580
gataactatg ttcgtcggag taaccaaaga ttacagcgtc ctcacgtcta cctgcctata    2640
cacctttatg gacaactagt acaccataaa acaggctgcc atttgttgga agtacagaat    2700
attattacag aactctgtcg taatgttcgt acaccagatt tggataagtg ggaagaaatt    2760
aaaaaactga agcatctctc ttgggccttg ggaaatatcg gctcatcaaa ttggggtctc    2820
aatttgctac aggaagaaaa cgtgattcca gatatactaa aacttgcaaa acagtgtgaa    2880
gttctttcca tcagagggac ctgtgtatat gtacttgggc tcatagctaa aaccaaacaa    2940
ggctgtgata ttctaaaatg tcacaactgg gatgctgtga ggcatagtcg caaacatctg    3000
tggccagtgg ttccagatga tgtggaacaa ctctgtaatg aactttcatc tatcccaagc    3060
actctaagtt tgaactcgga gtcaaccagc tctagacata atagtgaaag tgaatctgtg    3120
ccatcgagta tgttcatatt ggaggatgac cggtttggca gcagctctac tagtacattt    3180
ttccttgata tcaatgaaga tacagagcca acattttatg accgatctgg acccataaag    3240
gataaaaatt cattcccttt ctttgcttct agtaaacttg tgaagaatcg tatcttaaat    3300
tcgcttactt tgcctaacaa aaaacatcgt agtagcagtg atccaaaagg agggaaatta    3360
tcatctgaaa gtaagacaag caacaggcga atcagaacac ttacggagcc cagtgttgat    3420
tttaatcata gtgatgattt tacacccata tccactgtac agaaaacatt acaattagag    3480 acttcatttta tggggaataa gcacattgaa gacactggta gtacaccaag cattggaaga    3540
aatgacttaa aattcaccaa gaattttggt acagagaatc acagagaaaa tacaagccga    3600
gagaggttag tagtagaaag ttcaacgagc tcacatatga agatacgtag ccaaagtttc    3660
aatacagaca ctacaacaag tggcataagt tcaatgagct caagtccttc acgagagaca    3720
```

```
gtaggtgtag atgctacaac tatggacaca gactgtggaa gcatgagtac tgtggtaagt    3780
actaaaacta ttaagacaag ccactatttg acgccacagt ctaaccatct gtctctctcc    3840
aaatcaaatt cggtgtccct ggtgcctcca ggttcttctc atacgcttcc tagaagagca    3900
cagtccctta aagcaccctc tattgctaca attaaaagtc tagcagattg taactttagt    3960
tacacaagtt ctagagatgc ttttggctat gctacactga aaagactaca gcaacaaaga    4020
atgcatccat ccttatctca ctctgaagct tggcatctc cagcaaaaga tgtgctattt     4080
actgatacca tcaccatgaa ggccaacagt tttgagtcca gattaacacc aagcaggttc    4140
atgaaagcct taagttatgc atcattagat aaagaagatt tattgagtcc tattaatcaa    4200 aatacccctgc aacgatcttc ctcagtgcgg tccatggtgt ccagtgccac atatgggggt   4260
tcagatgatt acattggtct tgctctcccg gtggatataa atgatatatt ccaggtaaag    4320
gatattccct attttcagac aaaaaacata ccaccacatg atgatcgagg tgcaagagca    4380
tttgcccatg atgcaggagg tcttccatct ggaactggag tcttgtaaa aaattctttt     4440 cacttgctac gacagcagat gagtcttacg gaaataatga attcaatcca ttcagatgcc    4500
tctctgtttt tagaaagtac agaagacact ggactacagg aacatacaga tgataactgc    4560
ctttattgtg tctgtattga aattctgggt ttccagccca gcaaccaact gagtgcaata    4620
tgtagtcatt cagactttca agatattcca tattctgatt ggtgtgagca gactatccat    4680
aatcctttag aagtggttcc ctctaagttt cggggatttt ctggatgcag tgatggggtg    4740
tctcaagaag gctcagctag cagcaccaaa agcacagaat tgttactagg tgttaaaaca    4800
attccagatg atacaccaat gtgccgtata ctccttcgca aagaagttct aagattagtc    4860
attaatttga gtagttcagt ttcaactaaa tgtcatgaga ctgggctttt aacaattaag    4920
gagaagtatc ctcaaacatt tgatgacata tgcctttact ctgaggtttc ccatttgctg    4980
tcacactgca cattcagact tccgtgtcgg aggttcatac aagaattatt tcaagatgta    5040
cagtttctac aaatgcatga agaagcagag gctgtgttgg caacaccacc aaagcaacct    5100
atagttgata catctgctga atcctga                                         5127
```

<210> SEQ ID NO 3
<211> LENGTH: 1708
<212> TYPE: PRT
<213> ORGANISM: Homo sapiens

<400> SEQUENCE: 3

```
Met Ala Ala Ile Gly Arg Gly Arg Ser Leu Lys Asn Leu Arg Val Arg
1               5                   10                  15

Gly Arg Asn Asp Ser Gly Glu Glu Asn Val Pro Leu Asp Leu Thr Arg
            20                  25                  30

Glu Pro Ser Asp Asn Leu Arg Glu Ile Leu Gln Asn Val Ala Arg Leu
        35                  40                  45

Gln Gly Val Ser Asn Met Arg Lys Leu Gly His Leu Asn Asn Phe Thr
    50                  55                  60

Lys Leu Leu Cys Asp Ile Gly His Ser Glu Glu Lys Leu Gly Phe His
65                  70                  75                  80

Tyr Glu Asp Ile Ile Ile Cys Leu Arg Leu Ala Leu Leu Asn Glu Ala
                85                  90                  95

Lys Glu Val Arg Ala Ala Gly Leu Arg Ala Leu Arg Tyr Leu Ile Gln
            100                 105                 110

Asp Ser Ser Ile Leu Gln Lys Val Leu Lys Leu Lys Val Asp Tyr Leu
        115                 120                 125
```

-continued

```
Ile Ala Arg Cys Ile Asp Ile Gln Gln Ser Asn Glu Val Glu Arg Thr
    130                 135                 140

Gln Ala Leu Arg Leu Val Arg Lys Met Ile Thr Val Asn Ala Ser Leu
145                 150                 155                 160

Phe Pro Ser Ser Val Thr Asn Ser Leu Ile Ala Val Gly Asn Asp Gly
                165                 170                 175

Leu Gln Glu Arg Asp Arg Met Val Arg Ala Cys Ile Ala Ile Ile Cys
            180                 185                 190

Glu Leu Ala Leu Gln Asn Pro Glu Val Val Ala Leu Arg Gly Gly Leu
        195                 200                 205

Asn Thr Ile Leu Lys Asn Val Ile Asp Cys Gln Leu Ser Arg Ile Asn
210                 215                 220

Glu Ala Leu Ile Thr Thr Ile Leu His Leu Leu Asn His Pro Lys Thr
225                 230                 235                 240

Arg Gln Tyr Val Arg Ala Asp Val Glu Leu Glu Arg Ile Leu Ala Pro
                245                 250                 255

Tyr Thr Asp Phe His Tyr Arg His Ser Pro Asp Thr Ala Glu Gly Gln
            260                 265                 270

Leu Lys Glu Asp Arg Glu Ala Arg Phe Leu Ala Ser Lys Met Gly Ile
        275                 280                 285

Ile Ala Thr Phe Arg Ser Trp Ala Gly Ile Ile Asn Leu Cys Lys Pro
290                 295                 300

Gly Asn Ser Gly Ile Gln Ser Leu Ile Gly Val Leu Cys Ile Pro Asn
305                 310                 315                 320

Met Glu Ile Arg Arg Gly Leu Leu Glu Val Leu Tyr Asp Ile Phe Arg
                325                 330                 335

Leu Pro Leu Pro Val Val Thr Glu Glu Phe Ile Glu Ala Leu Leu Ser
            340                 345                 350

Val Asp Pro Gly Arg Phe Gln Asp Ser Trp Arg Leu Ser Asp Gly Phe
        355                 360                 365

Val Ala Ala Glu Ala Lys Thr Ile Leu Pro His Arg Ala Arg Ser Arg
370                 375                 380

Pro Asp Leu Met Asp Asn Tyr Leu Ala Leu Ile Leu Ser Ala Phe Ile
385                 390                 395                 400

Arg Asn Gly Leu Leu Glu Gly Leu Val Glu Val Ile Thr Asn Ser Asp
                405                 410                 415

Asp His Ile Ser Val Arg Ala Thr Ile Leu Leu Gly Glu Leu Leu His
            420                 425                 430

Met Ala Asn Thr Ile Leu Pro His Ser His Ser His His Leu His Cys
        435                 440                 445

Leu Pro Thr Leu Met Asn Met Ala Ala Ser Phe Asp Ile Pro Lys Glu
450                 455                 460

Lys Arg Leu Arg Ala Ser Ala Ala Leu Asn Cys Leu Lys Arg Phe His
465                 470                 475                 480

Glu Met Lys Lys Arg Gly Pro Lys Pro Tyr Ser Leu His Leu Asp His
                485                 490                 495

Ile Ile Gln Lys Ala Ile Ala Thr His Gln Lys Arg Asp Gln Tyr Leu
            500                 505                 510

Arg Val Gln Lys Asp Ile Phe Ile Leu Lys Asp Thr Glu Glu Ala Leu
        515                 520                 525

Leu Ile Asn Leu Arg Asp Ser Gln Val Leu Gln His Lys Glu Asn Leu
530                 535                 540

Glu Trp Asn Trp Asn Leu Ile Gly Thr Ile Leu Lys Trp Pro Asn Val
545                 550                 555                 560
```

Asn Leu Arg Asn Tyr Lys Asp Glu Gln Leu His Arg Phe Val Arg Arg
            565                 570                 575

Leu Leu Tyr Phe Tyr Lys Pro Ser Ser Lys Leu Tyr Ala Asn Leu Asp
            580                 585                 590

Leu Asp Phe Ala Lys Ala Lys Gln Leu Thr Val Val Gly Cys Gln Phe
595                 600                 605

Thr Glu Phe Leu Leu Glu Ser Glu Glu Asp Gly Gln Gly Tyr Leu Glu
            610                 615                 620

Asp Leu Val Lys Asp Ile Val Gln Trp Leu Asn Ala Ser Ser Gly Met
625                 630                 635                 640

Lys Pro Glu Arg Ser Leu Gln Asn Asn Gly Leu Leu Thr Thr Leu Ser
            645                 650                 655

Gln His Tyr Phe Leu Phe Ile Gly Thr Leu Ser Cys His Pro His Gly
            660                 665                 670

Val Lys Met Leu Glu Lys Cys Ser Val Phe Gln Cys Leu Leu Asn Leu
            675                 680                 685

Cys Ser Leu Lys Asn Gln Asp His Leu Leu Lys Leu Thr Val Ser Ser
690                 695                 700

Leu Asp Tyr Ser Arg Asp Gly Leu Ala Arg Val Ile Leu Ser Lys Ile
705                 710                 715                 720

Leu Thr Ala Ala Thr Asp Ala Cys Arg Leu Tyr Ala Thr Lys His Leu
            725                 730                 735

Arg Val Leu Leu Arg Ala Asn Val Glu Phe Phe Asn Asn Trp Gly Ile
            740                 745                 750

Glu Leu Leu Val Thr Gln Leu His Asp Lys Asn Lys Thr Ile Ser Ser
            755                 760                 765

Glu Ala Leu Asp Ile Leu Asp Glu Ala Cys Glu Asp Lys Ala Asn Leu
            770                 775                 780

His Ala Leu Ile Gln Met Lys Pro Ala Leu Ser His Leu Gly Asp Lys
785                 790                 795                 800

Gly Leu Leu Leu Leu Arg Phe Leu Ser Ile Pro Lys Gly Phe Ser
            805                 810                 815

Tyr Leu Asn Glu Arg Gly Tyr Val Ala Lys Gln Leu Glu Lys Trp His
            820                 825                 830

Arg Glu Tyr Asn Ser Lys Tyr Val Asp Leu Ile Glu Glu Gln Leu Asn
            835                 840                 845

Glu Ala Leu Thr Thr Tyr Arg Lys Pro Val Asp Gly Asp Asn Tyr Val
850                 855                 860

Arg Arg Ser Asn Gln Arg Leu Gln Arg Pro His Val Tyr Leu Pro Ile
865                 870                 875                 880

His Leu Tyr Gly Gln Leu Val His His Lys Thr Gly Cys His Leu Leu
            885                 890                 895

Glu Val Gln Asn Ile Ile Thr Glu Leu Cys Arg Asn Val Arg Thr Pro
            900                 905                 910

Asp Leu Asp Lys Trp Glu Glu Ile Lys Lys Leu Lys Ala Ser Leu Trp
            915                 920                 925

Ala Leu Gly Asn Ile Gly Ser Ser Asn Trp Gly Leu Asn Leu Leu Gln
            930                 935                 940

Glu Glu Asn Val Ile Pro Asp Ile Leu Leu Ala Lys Gln Cys Glu
945                 950                 955                 960

Val Leu Ser Ile Arg Gly Thr Cys Val Tyr Val Leu Gly Leu Ile Ala
            965                 970                 975

Lys Thr Lys Gln Gly Cys Asp Ile Leu Lys Cys His Asn Trp Asp Ala

-continued

```
                980             985             990
Val Arg His Ser Arg Lys His Leu Trp Pro Val Pro Asp Asp Val
        995             1000            1005
Glu Gln Leu Cys Asn Glu Leu Ser Ser Ile Pro Ser Thr Leu Ser
        1010            1015            1020
Leu Asn Ser Glu Ser Thr Ser Ser Arg His Asn Ser Glu Ser Glu
1025            1030            1035
Ser Val Pro Ser Ser Met Phe Ile Leu Glu Asp Asp Arg Phe Gly
            1040            1045            1050
Ser Ser Ser Thr Ser Thr Phe Phe Leu Asp Ile Asn Glu Asp Thr
            1055            1060            1065
Glu Pro Thr Phe Tyr Asp Arg Ser Gly Pro Ile Lys Asp Lys Asn
        1070            1075            1080
Ser Phe Pro Phe Phe Ala Ser Ser Lys Leu Val Lys Asn Arg Ile
        1085            1090            1095
Leu Asn Ser Leu Thr Leu Pro Asn Lys Lys His Arg Ser Ser Ser
1100            1105            1110
Asp Pro Lys Gly Gly Lys Leu Ser Ser Glu Ser Lys Thr Ser Asn
            1115            1120            1125
Arg Arg Ile Arg Thr Leu Thr Glu Pro Ser Val Asp Phe Asn His
            1130            1135            1140
Ser Asp Asp Phe Thr Pro Ile Ser Thr Val Gln Lys Thr Leu Gln
        1145            1150            1155
Leu Glu Thr Ser Phe Met Gly Asn Lys His Ile Glu Asp Thr Gly
        1160            1165            1170
Ser Thr Pro Ser Ile Gly Glu Asn Asp Leu Lys Phe Thr Lys Asn
1175            1180            1185
Phe Gly Thr Glu Asn His Arg Glu Asn Thr Ser Arg Glu Arg Leu
            1190            1195            1200
Val Val Glu Ser Ser Thr Ser Ser His Met Lys Ile Arg Ser Gln
            1205            1210            1215
Ser Phe Asn Thr Asp Thr Thr Thr Ser Gly Ile Ser Ser Met Ser
        1220            1225            1230
Ser Ser Pro Ser Arg Glu Thr Val Gly Val Asp Ala Thr Thr Met
        1235            1240            1245
Asp Thr Asp Cys Gly Ser Met Ser Thr Val Val Ser Thr Lys Thr
1250            1255            1260
Ile Lys Thr Ser His Tyr Leu Thr Pro Gln Ser Asn His Leu Ser
            1265            1270            1275
Leu Ser Lys Ser Asn Ser Val Ser Leu Val Pro Pro Gly Ser Ser
            1280            1285            1290
His Thr Leu Pro Arg Arg Ala Gln Ser Leu Lys Ala Pro Ser Ile
        1295            1300            1305
Ala Thr Ile Lys Ser Leu Ala Asp Cys Asn Phe Ser Tyr Thr Ser
        1310            1315            1320
Ser Arg Asp Ala Phe Gly Tyr Ala Thr Leu Lys Arg Leu Gln Gln
1325            1330            1335
Gln Arg Met His Pro Ser Leu Ser His Ser Glu Ala Leu Ala Ser
            1340            1345            1350
Pro Ala Lys Asp Val Leu Phe Thr Asp Thr Ile Thr Met Lys Ala
            1355            1360            1365
Asn Ser Phe Glu Ser Arg Leu Thr Pro Ser Arg Phe Met Lys Ala
        1370            1375            1380
```

| | | | | | | | | | | |
|---|---|---|---|---|---|---|---|---|---|---|
|Leu|Ser|Tyr|Ala|Ser|Leu|Asp|Lys|Glu|Asp|Leu Leu Ser Pro Ile|
| |1385| | | |1390| | | |1395| |
|Asn|Gln|Asn|Thr|Leu|Gln|Arg|Ser|Ser|Val|Arg Ser Met Val|
|1400| | | | |1405| | | |1410| |
|Ser|Ser|Ala|Thr|Tyr|Gly|Gly|Ser|Asp|Tyr|Ile Gly Leu Ala|
| | |1415| | | | |1420| | |1425|
|Leu|Pro|Val|Asp|Ile|Asn|Asp|Ile|Phe|Gln|Val Lys Asp Ile Pro|
| | | |1430| | | |1435| | |1440|
|Tyr|Phe|Gln|Thr|Lys|Asn|Ile|Pro|Pro|His|Asp Asp Arg Gly Ala|
| | | |1445| | | |1450| | |1455|
|Arg|Ala|Phe|Ala|His|Asp|Ala|Gly|Gly|Leu|Pro Ser Gly Thr Gly|
| | |1460| | | |1465| | | |1470|
|Gly|Leu|Val|Lys|Asn|Ser|Phe|His|Leu|Leu|Arg Gln Gln Met Ser|
|1475| | | |1480| | | |1485| | |
|Leu|Thr|Glu|Ile|Met|Asn|Ser|Ile|His|Ser|Asp Ala Ser Leu Phe|
| | | |1490| | | |1495| | |1500|
|Leu|Glu|Ser|Thr|Glu|Asp|Thr|Gly|Leu|Gln|Glu His Thr Asp Asp|
| | | |1505| | | |1510| | |1515|
|Asn|Cys|Leu|Tyr|Cys|Val|Cys|Ile|Glu|Ile|Leu Gly Phe Gln Pro|
| | |1520| | | |1525| | | |1530|
|Ser|Asn|Gln|Leu|Ser|Ala|Ile|Cys|Ser|His|Ser Asp Phe Gln Asp|
|1535| | | |1540| | | |1545| | |
|Ile|Pro|Tyr|Ser|Asp|Trp|Cys|Glu|Gln|Thr|Ile His Asn Pro Leu|
|1550| | | |1555| | | |1560| | |
|Glu|Val|Val|Pro|Ser|Lys|Phe|Ser|Gly|Ile|Ser Gly Cys Ser Asp|
| | | |1565| | | |1570| | |1575|
|Gly|Val|Ser|Gln|Glu|Gly|Ser|Ala|Ser|Ser|Thr Lys Ser Thr Glu|
| | | |1580| | | |1585| | |1590|
|Leu|Leu|Leu|Gly|Val|Lys|Thr|Ile|Pro|Asp|Asp Thr Pro Met Cys|
| | |1595| | | |1600| | | |1605|
|Arg|Ile|Leu|Leu|Arg|Lys|Glu|Val|Leu|Arg|Leu Val Ile Asn Leu|
| |1610| | | |1615| | | |1620| |
|Ser|Ser|Ser|Val|Ser|Thr|Lys|Cys|His|Glu|Thr Gly Leu Leu Thr|
|1625| | | |1630| | | |1635| | |
|Ile|Lys|Glu|Lys|Tyr|Pro|Gln|Thr|Phe|Asp|Ile Cys Leu Tyr|
| | | |1640| | | |1645| | |1650|
|Ser|Glu|Val|Ser|His|Leu|Leu|Ser|His|Cys|Thr Phe Arg Leu Pro|
| | | |1655| | | |1660| | |1665|
|Cys|Arg|Arg|Phe|Ile|Gln|Glu|Leu|Phe|Gln|Asp Val Gln Phe Leu|
| | |1670| | | |1675| | | |1680|
|Gln|Met|His|Glu|Glu|Ala|Glu|Ala|Val|Leu|Ala Thr Pro Pro Lys|
| |1685| | | |1690| | | |1695| |
|Gln|Pro|Ile|Val|Asp|Thr|Ser|Ala|Glu|Ser| |
|1700| | | | |1705| | | | | |

<210> SEQ ID NO 4
<211> LENGTH: 1817
<212> TYPE: DNA
<213> ORGANISM: Homo sapiens

<400> SEQUENCE: 4

```
gtgcggagcc gcccgtaaga tgctctgacc tttgaccctg ccgttcagct ctagggcccg      60
tgcaggccac accatgaaca cctccccagg cacggtgggc agtgaccggg tcatcctggc     120
cactgcaggc tacgaccaca ccgtgcgctt ctggcaggcc acagcggca tctgcacccg      180
```

-continued

| | |
|---|---|
| gacggtgcag caccaggact cccaggtgaa tgccttggag gtcacaccgg accgcagcat | 240 |
| gattgctgct gcaggttacc agcacatccg catgtatgat ctcaactcca ataaccctaa | 300 |
| ccccatcatc agctacgacg gcgtcaacaa gaacatcgcg tctgtgggct tccacgaaga | 360 |
| cggccgctgg atgtacacgg gcggcgagga ctgcacagcc aggatctggg acctcaggtc | 420 |
| ccggaacctg cagtgccagc ggatcttcca ggtgaacgca cccattaact gcgtgtgcct | 480 |
| gcacccgaac caggcagagc tcatcgtggg tgaccgagc ggggctatcc acatctggga | 540 |
| cttgaaaaca gaccacaacg agcagctgat ccctgagccc gaggtctcca tcacgtccgc | 600 |
| ccacatcgat cccgacgcca gctacatggc agctgtcaat agcaccggaa actgctatgt | 660 |
| ctggaatctg acgggggca ttggtgacga ggtgacccag ctcatcccca agactaagat | 720 |
| ccctgcccac acgcgctacg ccctgcagtg tcgcttcagc cccgactcca cgctcctcgc | 780 |
| cacctgctcg gctgatcaga cgtgcaagat ctggaggacg tccaacttct ccctgatgac | 840 |
| ggagctgagc atcaagagcg gcaacccgg ggagtcctcc cgcggctgga tgtggggctg | 900 |
| cgccttctcg ggggactccc agtacatcgt cactggtgag ccccgccctg gcctcccca | 960 |
| tccctggccc ccggcgctgg cctccagagc cagcccacct cggctgcagc ttccctctg | 1020 |
| ctggggccgc ctgcttggcc tgcacctgcg ctcttagccc tgcacaatct cccctccag | 1080 |
| cttcctcgga caacctggcc cggctctggt gtgtggagac tggagagatc aagagagagt | 1140 |
| atggcggcca ccagaaggct gttgtctgcc tggccttcaa tgacagtgtg ctgggctagc | 1200 |
| ctgtgacccc tcgggactgc ctggtgcagg tggtggcagc tggagggacc catgcagcac | 1260 |
| ccaggtcaga gcagaccctc ccctgccggc ctgcgccagc tggacctgat ggccccctgt | 1320 |
| ggcgccttga cctgctgggc caggctgccc tgggactctc agcccccagt tgcttatcca | 1380 |
| gatgtgacag agctcgaccc aagccaggct gcacactcct ggactgggct agcctgcact | 1440 |
| gcctgggaaa gtcggccgag ggcccaaagc tgctgagggg tctgaggctg gtgcccaccc | 1500 |
| ccaagctagt gcgttctctg cccctccctg cccgcgtttc agggcctcgg tccatagaga | 1560 |
| acaccaccac catggccagg tggaagggtt tattagtccc tgccagcagc tgtcctccct | 1620 |
| ggtgcaggtg gcctggccag cccactggat tggggacggg ccaggctggg ccaggtcggg | 1680 |
| ggctcagtct gggaggtaat aaaagcagac cgacacgcag atgttgctcg ggaaaaaaaa | 1740 |
| aaaaaaaaaa aaaaaacca aaaaaaaaaa aaaaaaaaaa aaaaaaaaaa aaaaaaaaaa | 1800 |
| aaaaaaaaaa aaaaaaa | 1817 |

<210> SEQ ID NO 5
<211> LENGTH: 981
<212> TYPE: DNA
<213> ORGANISM: Homo sapiens

<400> SEQUENCE: 5

| | |
|---|---|
| atgaacacct ccccaggcac ggtgggcagt gacccggtca tcctggccac tgcaggctac | 60 |
| gaccacaccg tgcgcttctg gcaggcccac agcggcatct gcacccggac ggtgcagcac | 120 |
| caggactccc aggtgaatgc cttggaggtc acaccggacc gcagcatgat tgctgctgca | 180 |
| ggttaccagc acatccgcat gtatgatctc aactccaata accctaaccc catcatcagc | 240 |
| tacgacggc tcaacaagaa catcgcgtct gtgggcttcc acgaagacgg ccgctggatg | 300 |
| tacacgggcg gcgaggactg cacagccagg atctgggacc tcaggtcccg gaacctgcag | 360 |
| tgccagcgga tcttccaggt gaacgcaccc attaactgcg tgtgcctgca ccccaaccag | 420 |
| gcagagctca tcgtgggtga ccagagcggg gctatccaca tctgggactt gaaaacagac | 480 |

-continued

```
cacaacgagc agctgatccc tgagcccgag gtctccatca cgtccgccca catcgatccc    540
gacgccagct acatggcagc tgtcaatagc accggaaact gctatgtctg aatctgacg     600 gggggcattg gtgacgaggt gacccagctc atccccaaga ctaagatccc tgcccacacg    660
cgctacgccc tgcagtgtcg cttcagcccc gactccacgc tcctcgccac ctgctcgggt    720
gatcagacgt gcaagatctg gaggacgtcc aacttctccc tgatgacgga gctgagcatc    780
aagagcggca ccccggggga gtcctcccgc ggctggatgt ggggctgcgc cttctcgggg    840
gactcccagt acatcgtcac tgcttcctcg acaacctggg cccggctctg tgtgtggag     900 actggagaga tcaagagaga gtatggcggc caccagaagg ctgttgtctg cctggccttc    960
aatgacagtg tgctgggcta g                                              981
```

<210> SEQ ID NO 6
<211> LENGTH: 327
<212> TYPE: PRT
<213> ORGANISM: Homo sapiens

<400> SEQUENCE: 6

```
Met Asn Thr Ser Pro Gly Thr Val Gly Ser Asp Pro Val Ile Leu Ala
1               5                   10                  15

Thr Ala Gly Tyr Asp His Thr Val Arg Phe Trp Gln Ala His Ser Gly
            20                  25                  30

Ile Cys Thr Arg Thr Val Gln His Gln Asp Ser Gln Val Asn Ala Leu
        35                  40                  45

Glu Val Thr Pro Asp Arg Ser Met Ile Ala Ala Gly Tyr Gln His
    50                  55                  60

Ile Arg Met Tyr Asp Leu Asn Ser Asn Asn Pro Asn Pro Ile Ile Ser
65                  70                  75                  80

Tyr Asp Gly Val Asn Lys Asn Ile Ala Ser Val Gly Phe His Glu Asp
                85                  90                  95

Gly Arg Trp Met Tyr Thr Gly Gly Glu Asp Cys Thr Ala Arg Ile Trp
            100                 105                 110

Asp Leu Arg Ser Arg Asn Leu Gln Cys Gln Arg Ile Phe Gln Val Asn
        115                 120                 125

Ala Pro Ile Asn Cys Val Cys Leu His Pro Asn Gln Ala Glu Leu Ile
    130                 135                 140

Val Gly Asp Gln Ser Gly Ala Ile His Ile Trp Asp Leu Lys Thr Asp
145                 150                 155                 160

His Asn Glu Gln Leu Ile Pro Glu Pro Glu Val Ser Ile Thr Ser Ala
                165                 170                 175

His Ile Asp Pro Asp Ala Ser Tyr Met Ala Ala Val Asn Ser Thr Gly
            180                 185                 190

Asn Cys Tyr Val Trp Asn Leu Thr Gly Gly Ile Gly Asp Glu Val Thr
        195                 200                 205

Gln Leu Ile Pro Lys Thr Lys Ile Pro Ala His Thr Arg Tyr Ala Leu
    210                 215                 220

Gln Cys Arg Phe Ser Pro Asp Ser Thr Leu Leu Ala Thr Cys Ser Ala
225                 230                 235                 240

Asp Gln Thr Cys Lys Ile Trp Arg Thr Ser Asn Phe Ser Leu Met Thr
                245                 250                 255

Glu Leu Ser Ile Lys Ser Gly Asn Pro Gly Glu Ser Ser Arg Gly Trp
            260                 265                 270

Met Trp Gly Cys Ala Phe Ser Gly Asp Ser Gln Tyr Ile Val Thr Gly
        275                 280                 285
```

```
Glu Pro Arg Pro Gly Leu Pro His Pro Trp Pro Ala Leu Ala Ser
    290             295             300

Arg Ala Ser Pro Pro Arg Leu Gln Leu Pro Leu Cys Trp Gly Arg Leu
305             310             315             320

Leu Gly Leu His Leu Arg Ser
            325

<210> SEQ ID NO 7
<211> LENGTH: 19
<212> TYPE: RNA
<213> ORGANISM: Unknown
<220> FEATURE:
<223> OTHER INFORMATION: Description of Unknown: SiRNA oligonucleotide

<400> SEQUENCE: 7
acuugugaag aaucguauc                                               19

<210> SEQ ID NO 8
<211> LENGTH: 19
<212> TYPE: RNA
<213> ORGANISM: Unknown
<220> FEATURE:
<223> OTHER INFORMATION: Description of Unknown: SiRNA oligonucleotide

<400> SEQUENCE: 8
ugaacacuuc uuagcauag                                               19

<210> SEQ ID NO 9
<211> LENGTH: 19
<212> TYPE: RNA
<213> ORGANISM: Unknown
<220> FEATURE:
<223> OTHER INFORMATION: Description of Unknown: SiRNA oligonucleotide

<400> SEQUENCE: 9
uccuugucca aggaggcug                                               19

<210> SEQ ID NO 10
<211> LENGTH: 19
<212> TYPE: RNA
<213> ORGANISM: Unknown
<220> FEATURE:
<223> OTHER INFORMATION: Description of Unknown: SiRNA oligonucleotide

<400> SEQUENCE: 10
aggaacaggu uccuccgac                                               19

<210> SEQ ID NO 11
<211> LENGTH: 59
<212> TYPE: DNA
<213> ORGANISM: Unknown
<220> FEATURE:
<223> OTHER INFORMATION: Description of Unknown: oligonucleotide

<400> SEQUENCE: 11
ccggttcagc gtccctacct tcttctctcg agagaagaag gtagggacgc tgatttttg   59

<210> SEQ ID NO 12
<211> LENGTH: 59
<212> TYPE: DNA
<213> ORGANISM: Unknown
<220> FEATURE:
<223> OTHER INFORMATION: Description of Unknown: oligonucleotide

<400> SEQUENCE: 12
aattcaaaaa tcagcgtccc taccttcttc tctcgagaga agaaggtagg gacgctgaa   59
```

<210> SEQ ID NO 13
<211> LENGTH: 58
<212> TYPE: DNA
<213> ORGANISM: Unknown
<220> FEATURE:
<223> OTHER INFORMATION: Description of Unknown: oligonucleotide

<400> SEQUENCE: 13
ccggagggcc ctgctactcg cttttctcga gaaaagcgag tagcagggcc cttttttg    58

<210> SEQ ID NO 14
<211> LENGTH: 58
<212> TYPE: DNA
<213> ORGANISM: Unknown
<220> FEATURE:
<223> OTHER INFORMATION: Description of Unknown: oligonucleotide

<400> SEQUENCE: 14
aattcaaaaa agggccctgc tactcgcttt tctcgagaaa agcgagtagc agggccct    58

<210> SEQ ID NO 15
<211> LENGTH: 59
<212> TYPE: DNA
<213> ORGANISM: Unknown
<220> FEATURE:
<223> OTHER INFORMATION: Description of Unknown: oligonucleotide

<400> SEQUENCE: 15
ccggtacttg tgaagaatcg tatcttctcg agaagatacg attcttcaca gttttttg    59

<210> SEQ ID NO 16
<211> LENGTH: 59
<212> TYPE: DNA
<213> ORGANISM: Unknown
<220> FEATURE:
<223> OTHER INFORMATION: Description of Unknown: oligonucleotide

<400> SEQUENCE: 16
aattcaaaaa acttgtgaag aatcgtatct tctcgagaag atacgattct tcacaagta    59

<210> SEQ ID NO 17
<211> LENGTH: 25
<212> TYPE: DNA
<213> ORGANISM: Unknown
<220> FEATURE:
<223> OTHER INFORMATION: Description of Unknown: oligonucleotide

<400> SEQUENCE: 17
atggtgagca agggcgagga gctgt    25

<210> SEQ ID NO 18
<211> LENGTH: 25
<212> TYPE: DNA
<213> ORGANISM: Unknown
<220> FEATURE:
<223> OTHER INFORMATION: Description of Unknown: oligonucleotide

<400> SEQUENCE: 18
ttacttgtac agctcgtcca tgccg    25

<210> SEQ ID NO 19
<211> LENGTH: 25
<212> TYPE: DNA
<213> ORGANISM: Unknown
<220> FEATURE:
<223> OTHER INFORMATION: Description of Unknown: oligonucleotide

```
<400> SEQUENCE: 19
caggagttat tttaaatgtg cttcg                                              25

<210> SEQ ID NO 20
<211> LENGTH: 25
<212> TYPE: DNA
<213> ORGANISM: Unknown
<220> FEATURE:
<223> OTHER INFORMATION: Description of Unknown: oligonucleotide

<400> SEQUENCE: 20
ccaaaattct ttgatcagct taaaa                                              25

<210> SEQ ID NO 21
<211> LENGTH: 25
<212> TYPE: DNA
<213> ORGANISM: Unknown
<220> FEATURE:
<223> OTHER INFORMATION: Description of Unknown: oligonucleotide

<400> SEQUENCE: 21
tgtctgacaa cacccattaa catag                                              25

<210> SEQ ID NO 22
<211> LENGTH: 25
<212> TYPE: DNA
<213> ORGANISM: Unknown
<220> FEATURE:
<223> OTHER INFORMATION: Description of Unknown: oligonucleotide

<400> SEQUENCE: 22
gtacttgtat tccttgacca gatcc                                              25

<210> SEQ ID NO 23
<211> LENGTH: 25
<212> TYPE: DNA
<213> ORGANISM: Unknown
<220> FEATURE:
<223> OTHER INFORMATION: Description of Unknown: oligonucleotide

<400> SEQUENCE: 23
gcttattcct agacagcatt atcca                                              25

<210> SEQ ID NO 24
<211> LENGTH: 25
<212> TYPE: DNA
<213> ORGANISM: Unknown
<220> FEATURE:
<223> OTHER INFORMATION: Description of Unknown: oligonucleotide

<400> SEQUENCE: 24
ttttgagtac ttcgatgcct tttac                                              25

<210> SEQ ID NO 25
<211> LENGTH: 25
<212> TYPE: DNA
<213> ORGANISM: Unknown
<220> FEATURE:
<223> OTHER INFORMATION: Description of Unknown: oligonucleotide

<400> SEQUENCE: 25
ccttcatagt ggagctagtt tatgc                                              25

<210> SEQ ID NO 26
<211> LENGTH: 25
```

```
<212> TYPE: DNA
<213> ORGANISM: Unknown
<220> FEATURE:
<223> OTHER INFORMATION: Description of Unknown: oligonucleotide

<400> SEQUENCE: 26
cttagcgttg tatcatcagg tgaat                                              25

<210> SEQ ID NO 27
<211> LENGTH: 27
<212> TYPE: DNA
<213> ORGANISM: Unknown
<220> FEATURE:
<223> OTHER INFORMATION: Description of Unknown: oligonucleotide

<400> SEQUENCE: 27
gaattaatac gactcactat agggaga                                            27

<210> SEQ ID NO 28
<211> LENGTH: 326
<212> TYPE: PRT
<213> ORGANISM: Homo sapiens

<400> SEQUENCE: 28
```

Met Asn Thr Ser Pro Gly Thr Val Gly Ser Asp Pro Val Ile Leu Ala
1               5                   10                  15

Thr Ala Gly Tyr Asp His Thr Val Arg Phe Trp Gln Ala His Ser Gly
            20                  25                  30

Ile Cys Thr Arg Thr Val Gln His Gln Asp Ser Gln Val Asn Ala Leu
        35                  40                  45

Glu Val Thr Pro Asp Arg Ser Met Ile Ala Ala Gly Tyr Gln His
    50                  55                  60

Ile Arg Met Tyr Asp Leu Asn Ser Asn Asn Pro Asn Pro Ile Ile Ser
65                  70                  75                  80

Tyr Asp Gly Val Asn Lys Asn Ile Ala Ser Val Gly Phe His Glu Asp
                85                  90                  95

Gly Arg Trp Met Tyr Thr Gly Gly Glu Asp Cys Thr Ala Arg Ile Trp
            100                 105                 110

Asp Leu Arg Ser Arg Asn Leu Gln Cys Gln Arg Ile Phe Gln Val Asn
        115                 120                 125

Ala Pro Ile Asn Cys Val Cys Leu His Pro Asn Gln Ala Glu Leu Ile
    130                 135                 140

Val Gly Asp Gln Ser Gly Ala Ile His Ile Trp Asp Leu Lys Thr Asp
145                 150                 155                 160

His Asn Glu Gln Leu Ile Pro Glu Pro Glu Val Ser Ile Thr Ser Ala
                165                 170                 175

His Ile Asp Pro Asp Ala Ser Tyr Met Ala Ala Val Asn Ser Thr Gly
            180                 185                 190

Asn Cys Tyr Val Trp Asn Leu Thr Gly Gly Ile Gly Asp Glu Val Thr
        195                 200                 205

Gln Leu Ile Pro Lys Thr Lys Ile Pro Ala His Thr Arg Tyr Ala Leu
    210                 215                 220

Gln Cys Arg Phe Ser Pro Asp Ser Thr Leu Leu Ala Thr Cys Ser Ala
225                 230                 235                 240

Asp Gln Thr Cys Lys Ile Trp Arg Thr Ser Asn Phe Ser Leu Met Thr
                245                 250                 255

Glu Leu Ser Ile Lys Ser Gly Asn Pro Gly Glu Ser Ser Arg Gly Trp
            260                 265                 270

```
Met Trp Gly Cys Ala Phe Ser Gly Asp Ser Gln Tyr Ile Val Thr Ala
        275                 280                 285

Ser Ser Asp Asn Leu Ala Arg Leu Trp Cys Val Glu Thr Gly Glu Ile
    290                 295                 300

Lys Arg Glu Tyr Gly Gly His Gln Lys Ala Val Val Cys Leu Ala Phe
305                 310                 315                 320

Asn Asp Ser Val Leu Gly
                325

<210> SEQ ID NO 29
<211> LENGTH: 30
<212> TYPE: PRT
<213> ORGANISM: Homo sapiens

<400> SEQUENCE: 29

Cys Gln Gln Tyr Phe Leu Tyr Ile Gly Arg Met Cys Arg Thr Val Lys
1               5                   10                  15

Gly Ile Glu Val Leu Lys Asn Thr Thr Val Phe Glu Tyr Leu
            20                  25                  30

<210> SEQ ID NO 30
<211> LENGTH: 30
<212> TYPE: PRT
<213> ORGANISM: Homo sapiens

<400> SEQUENCE: 30

Cys Gln His Tyr Phe Leu Phe Ile Gly Arg Met Cys Arg Thr Glu Gly
1               5                   10                  15

Gly Leu Glu Ile Leu Arg Asn Thr Asp Val Phe Lys Glu Leu
            20                  25                  30

<210> SEQ ID NO 31
<211> LENGTH: 30
<212> TYPE: PRT
<213> ORGANISM: Homo sapiens

<400> SEQUENCE: 31

Ser Gln His Tyr Phe Leu Phe Ile Gly Thr Leu Ser Cys His Pro His
1               5                   10                  15

Gly Val Lys Met Leu Glu Lys Cys Ser Val Phe Gln Cys Leu
            20                  25                  30

<210> SEQ ID NO 32
<211> LENGTH: 30
<212> TYPE: PRT
<213> ORGANISM: Homo sapiens

<400> SEQUENCE: 32

Ser Arg Glu Tyr Phe Thr Met Leu Gly Thr Leu Ser Ser Asn Leu Leu
1               5                   10                  15

Gly Leu Glu Ile Leu Ala Arg Asn Asn Ile Phe Asp Tyr Ile
            20                  25                  30

<210> SEQ ID NO 33
<211> LENGTH: 30
<212> TYPE: PRT
<213> ORGANISM: Homo sapiens

<400> SEQUENCE: 33

Thr His Gly Tyr Phe Pro Met Leu Lys Val Leu Ser Ser Gln Lys Glu
1               5                   10                  15

Gly His Ala Ile Met Glu Arg Trp Arg Ile Phe Thr Thr Leu
```

<210> SEQ ID NO 34
<211> LENGTH: 30
<212> TYPE: PRT
<213> ORGANISM: Homo sapiens

<400> SEQUENCE: 34

Pro Asn Val Ala Pro His Leu Tyr Gly Gln Met Ala Gln Thr Gly Gln
1               5                   10                  15

Gly Met Thr Ala Leu Arg Lys His Gly Asp Leu Pro Gln Leu
            20                  25                  30

<210> SEQ ID NO 35
<211> LENGTH: 30
<212> TYPE: PRT
<213> ORGANISM: Homo sapiens

<400> SEQUENCE: 35

Pro Asn Leu Ala Pro His Leu Tyr Gly Gln Leu Val Gln Thr Ser Lys
1               5                   10                  15

Gly Phe Ser Gln Leu Leu Thr His Gly Arg Leu Leu Glu Leu
            20                  25                  30

<210> SEQ ID NO 36
<211> LENGTH: 30
<212> TYPE: PRT
<213> ORGANISM: Homo sapiens

<400> SEQUENCE: 36

Val Tyr Leu Pro Ile His Leu Tyr Gly Gln Leu Val His His Lys Thr
1               5                   10                  15

Gly Cys His Leu Leu Glu Val Gln Asn Ile Ile Thr Glu Leu
            20                  25                  30

<210> SEQ ID NO 37
<211> LENGTH: 30
<212> TYPE: PRT
<213> ORGANISM: Homo sapiens

<400> SEQUENCE: 37

Val Tyr Leu Pro Pro His Phe Phe Gly Glu Leu Ala Lys Thr Glu Lys
1               5                   10                  15

Gly Cys Gln Leu Ile Arg Lys Ser Asn Asn Tyr Gln Arg Phe
            20                  25                  30

<210> SEQ ID NO 38
<211> LENGTH: 29
<212> TYPE: PRT
<213> ORGANISM: Homo sapiens

<400> SEQUENCE: 38

Ile Leu Pro Leu His Phe Tyr Gly Glu Leu Val Lys Ser Pro Gln Gly
1               5                   10                  15

Cys Glu Val Leu Glu Ser Ser Gly His Phe Glu Ser Phe
            20                  25

<210> SEQ ID NO 39
<211> LENGTH: 30
<212> TYPE: PRT
<213> ORGANISM: Homo sapiens

<400> SEQUENCE: 39

Leu Lys Ala Ala Ile Trp Ala Leu Ala His Ala Ser Thr His Ser Asn
1               5                   10                  15

Gly Ile Glu Tyr Phe Val Glu Leu Asn Ala Arg Leu Tyr Glu
            20                  25                  30

<210> SEQ ID NO 40
<211> LENGTH: 30
<212> TYPE: PRT
<213> ORGANISM: Homo sapiens

<400> SEQUENCE: 40

Leu Lys Ala Ala Leu Trp Ala Leu Met His Ala Cys Thr Ser Lys Glu
1               5                   10                  15

Ala Ile Glu Tyr Phe Thr Glu His Val Pro Trp Leu Leu Ala
            20                  25                  30

<210> SEQ ID NO 41
<211> LENGTH: 30
<212> TYPE: PRT
<213> ORGANISM: Homo sapiens

<400> SEQUENCE: 41

Leu Lys Ala Ser Leu Trp Ala Leu Gly Asn Ile Gly Ser Ser Asn Trp
1               5                   10                  15

Gly Leu Asn Leu Leu Gln Glu Glu Asn Val Ile Pro Asp Ile
            20                  25                  30

<210> SEQ ID NO 42
<211> LENGTH: 30
<212> TYPE: PRT
<213> ORGANISM: Homo sapiens

<400> SEQUENCE: 42

Lys Arg Ala Ser Leu Ile Ala Ile Gly His Ile Gly Ser Ser Val Asp
1               5                   10                  15

Gly Tyr Ser Phe Val Lys Glu Ser Asp Thr Ile Lys Leu Leu
            20                  25                  30

<210> SEQ ID NO 43
<211> LENGTH: 30
<212> TYPE: PRT
<213> ORGANISM: Homo sapiens

<400> SEQUENCE: 43

Leu Lys Ser Ala Leu Trp Ala Ile Gly Asn Ile Gly Lys Thr Asp Gln
1               5                   10                  15

Gly Ile Thr Phe Leu Ile Asn His Asp Thr Ile Pro Leu Ile
            20                  25                  30

<210> SEQ ID NO 44
<211> LENGTH: 30
<212> TYPE: PRT
<213> ORGANISM: Homo sapiens

<400> SEQUENCE: 44

Arg Ala Thr Cys Phe Ser Ala Leu Gly Leu Ile Ala Gly Thr Gln Ala
1               5                   10                  15

Gly Ala Asn Ile Leu Phe Lys Leu Asn Trp Leu Ser Val Arg
            20                  25                  30

<210> SEQ ID NO 45
<211> LENGTH: 30
<212> TYPE: PRT

```
<213> ORGANISM: Homo sapiens

<400> SEQUENCE: 45

Arg Ala Thr Ala Leu Gly Gly Leu Cys Leu Val Ala Ser Thr Ala Gln
1               5                   10                  15

Gly Ala Asp Ala Leu Arg Thr Leu Gly Trp Val Ala Val Arg
            20                  25                  30

<210> SEQ ID NO 46
<211> LENGTH: 30
<212> TYPE: PRT
<213> ORGANISM: Homo sapiens

<400> SEQUENCE: 46

Arg Gly Thr Cys Val Tyr Val Leu Gly Leu Ile Ala Lys Thr Lys Gln
1               5                   10                  15

Gly Cys Asp Ile Leu Lys Cys His Asn Trp Asp Ala Val Arg
            20                  25                  30

<210> SEQ ID NO 47
<211> LENGTH: 30
<212> TYPE: PRT
<213> ORGANISM: Homo sapiens

<400> SEQUENCE: 47

Arg Ser Thr Cys Phe Tyr Ala Leu Gly Met Ile Ser Cys Ile Glu Glu
1               5                   10                  15

Ala Gln Pro Ile Phe Asn Ser Phe Gly Trp Glu Ser Pro Ser
            20                  25                  30

<210> SEQ ID NO 48
<211> LENGTH: 30
<212> TYPE: PRT
<213> ORGANISM: Homo sapiens

<400> SEQUENCE: 48

Arg Gly Thr Ala Tyr Phe Val Leu Gly Leu Ile Ser Arg Thr Ser Lys
1               5                   10                  15

Gly Val Glu Ile Leu Glu Ser Leu His Trp Tyr Ser Leu Met
            20                  25                  30

<210> SEQ ID NO 49
<211> LENGTH: 325
<212> TYPE: PRT
<213> ORGANISM: Homo sapiens

<400> SEQUENCE: 49

Met Asn Thr Ser Pro Gly Thr Val Gly Ser Asp Pro Val Ile Leu Ala
1               5                   10                  15

Thr Ala Gly Tyr Asp His Thr Val Arg Phe Trp Gln Ala His Ser Gly
            20                  25                  30

Ile Cys Thr Arg Thr Val Gln His Gln Asp Ser Gln Val Asn Ala Leu
        35                  40                  45

Glu Val Thr Pro Asp Arg Ser Met Ile Ala Ala Gly Tyr Gln His
    50                  55                  60

Ile Arg Met Tyr Asp Leu Asn Ser Asn Asn Pro Asn Pro Ile Ile Ser
65                  70                  75                  80

Tyr Asp Gly Val Asn Lys Asn Ile Ala Ser Val Gly Phe His Glu Asp
                85                  90                  95

Gly Arg Trp Met Tyr Thr Gly Gly Glu Asp Cys Thr Ala Arg Ile Trp
            100                 105                 110
```

Asp Leu Arg Ser Arg Asn Leu Gln Cys Gln Arg Ile Phe Gln Val Asn
            115                 120                 125

Ala Pro Ile Asn Cys Val Cys Leu His Pro Asn Gln Ala Glu Leu Ile
        130                 135                 140

Val Gly Asp Gln Ser Gly Ala Ile His Ile Trp Asp Leu Lys Thr Asp
145                 150                 155                 160

His Asn Glu Gln Leu Ile Pro Glu Pro Glu Val Ser Ile Thr Ser Ala
                165                 170                 175

His Ile Asp Pro Asp Ala Ser Tyr Met Ala Ala Val Asn Ser Thr Gly
            180                 185                 190

Asn Cys Tyr Val Trp Asn Leu Gly Gly Ile Gly Asp Glu Val Thr Gln
        195                 200                 205

Leu Ile Pro Lys Thr Lys Ile Pro Ala His Thr Arg Tyr Ala Leu Gln
    210                 215                 220

Cys Arg Phe Ser Pro Asp Ser Thr Leu Leu Ala Thr Cys Ser Ala Asp
225                 230                 235                 240

Gln Thr Cys Lys Ile Trp Arg Thr Ser Asn Phe Ser Leu Met Thr Glu
                245                 250                 255

Leu Ser Ile Lys Ser Gly Asn Pro Gly Glu Ser Ser Arg Gly Trp Met
            260                 265                 270

Trp Gly Cys Ala Phe Ser Gly Asp Ser Gln Tyr Ile Val Thr Ala Ser
        275                 280                 285

Ser Asp Asn Leu Ala Arg Leu Trp Cys Val Glu Thr Gly Glu Ile Lys
    290                 295                 300

Arg Glu Tyr Gly Gly His Gln Lys Ala Val Val Cys Leu Ala Phe Asn
305                 310                 315                 320

Asp Ser Val Leu Gly
                325

<210> SEQ ID NO 50
<211> LENGTH: 15
<212> TYPE: PRT
<213> ORGANISM: Homo sapiens

<400> SEQUENCE: 50

Arg Gly Arg Ser Leu Lys Asn Leu Arg Val Arg Gly Arg Asn Asp
1               5                   10                  15

<210> SEQ ID NO 51
<211> LENGTH: 20
<212> TYPE: PRT
<213> ORGANISM: Homo sapiens

<400> SEQUENCE: 51

Met Glu Ser Glu Met Leu Gln Ser Pro Leu Leu Gly Leu Gly Glu Glu
1               5                   10                  15

Asp Glu Ala Asp
            20

<210> SEQ ID NO 52
<211> LENGTH: 2549
<212> TYPE: PRT
<213> ORGANISM: Homo sapiens

<400> SEQUENCE: 52

Met Leu Gly Thr Gly Pro Ala Ala Ala Thr Thr Ala Ala Thr Thr Ser
1               5                   10                  15

Ser Asn Val Ser Val Leu Gln Gln Phe Ala Ser Gly Leu Lys Ser Arg

-continued

```
                20                  25                  30
Asn Glu Glu Thr Arg Ala Lys Ala Ala Lys Glu Leu Gln His Tyr Val
                35                  40                  45
Thr Met Glu Leu Arg Glu Met Ser Gln Glu Glu Ser Thr Arg Phe Tyr
                50                  55                  60
Asp Gln Leu Asn His His Ile Phe Glu Leu Val Ser Ser Ser Asp Ala
65                  70                  75                  80
Asn Glu Arg Lys Gly Gly Ile Leu Ala Ile Ala Ser Leu Ile Gly Val
                85                  90                  95
Glu Gly Gly Asn Ala Thr Arg Ile Gly Arg Phe Ala Asn Tyr Leu Arg
                100                 105                 110
Asn Leu Leu Pro Ser Asn Asp Pro Val Val Met Glu Met Ala Ser Lys
                115                 120                 125
Ala Ile Gly Arg Leu Ala Met Ala Gly Asp Thr Phe Thr Ala Glu Tyr
                130                 135                 140
Val Glu Phe Glu Val Lys Arg Ala Leu Glu Trp Leu Gly Ala Asp Arg
145                 150                 155                 160
Asn Glu Gly Arg Arg His Ala Ala Val Leu Val Leu Arg Glu Leu Ala
                165                 170                 175
Ile Ser Val Pro Thr Phe Phe Phe Gln Gln Val Gln Pro Phe Phe Asp
                180                 185                 190
Asn Ile Phe Val Ala Val Trp Asp Pro Lys Gln Ala Ile Arg Glu Gly
                195                 200                 205
Ala Val Ala Ala Leu Arg Ala Cys Leu Ile Leu Thr Thr Gln Arg Glu
                210                 215                 220
Pro Lys Glu Met Gln Lys Pro Gln Trp Tyr Arg His Thr Phe Glu Glu
225                 230                 235                 240
Ala Glu Lys Gly Phe Asp Glu Thr Leu Ala Lys Lys Gly Met Asn
                245                 250                 255
Arg Asp Asp Arg Ile His Gly Ala Leu Leu Ile Leu Asn Glu Leu Val
                260                 265                 270
Arg Ile Ser Ser Met Glu Gly Glu Arg Leu Arg Glu Glu Met Glu Glu
                275                 280                 285
Ile Thr Gln Gln Gln Leu Val His Asp Lys Tyr Cys Lys Asp Leu Met
                290                 295                 300
Gly Phe Gly Thr Lys Pro Arg His Ile Thr Pro Phe Thr Ser Phe Gln
305                 310                 315                 320
Ala Val Gln Pro Gln Gln Ser Asn Ala Leu Val Gly Leu Leu Gly Tyr
                325                 330                 335
Ser Ser His Gln Gly Leu Met Gly Phe Gly Thr Ser Pro Ser Pro Ala
                340                 345                 350
Lys Ser Thr Leu Val Glu Ser Arg Cys Cys Arg Asp Leu Met Glu Glu
                355                 360                 365
Lys Phe Asp Gln Val Cys Gln Trp Val Leu Lys Cys Arg Asn Ser Lys
                370                 375                 380
Asn Ser Leu Ile Gln Met Thr Ile Leu Asn Leu Pro Arg Leu Ala
385                 390                 395                 400
Ala Phe Arg Pro Ser Ala Phe Thr Asp Thr Gln Tyr Leu Gln Asp Thr
                405                 410                 415
Met Asn His Val Leu Ser Cys Val Lys Lys Glu Lys Glu Arg Thr Ala
                420                 425                 430
Ala Phe Gln Ala Leu Gly Leu Leu Ser Val Ala Val Arg Ser Glu Phe
                435                 440                 445
```

```
Lys Val Tyr Leu Pro Arg Val Leu Asp Ile Ile Arg Ala Ala Leu Pro
        450                 455                 460

Pro Lys Asp Phe Ala His Lys Arg Gln Lys Ala Met Gln Val Asp Ala
465                 470                 475                 480

Thr Val Phe Thr Cys Ile Ser Met Leu Ala Arg Ala Met Gly Pro Gly
                485                 490                 495

Ile Gln Gln Asp Ile Lys Glu Leu Leu Glu Pro Met Leu Ala Val Gly
                500                 505                 510

Leu Ser Pro Ala Leu Thr Ala Val Leu Tyr Asp Leu Ser Arg Gln Ile
        515                 520                 525

Pro Gln Leu Lys Lys Asp Ile Gln Asp Gly Leu Leu Lys Met Leu Ser
530                 535                 540

Leu Val Leu Met His Lys Pro Leu Arg His Pro Gly Met Pro Lys Gly
545                 550                 555                 560

Leu Ala His Gln Leu Ala Ser Pro Gly Leu Thr Thr Leu Pro Glu Ala
                565                 570                 575

Ser Asp Val Gly Ser Ile Thr Leu Ala Leu Arg Thr Leu Gly Ser Phe
            580                 585                 590

Glu Phe Glu Gly His Ser Leu Thr Gln Phe Val Arg His Cys Ala Asp
        595                 600                 605

His Phe Leu Asn Ser Glu His Lys Glu Ile Arg Met Glu Ala Ala Arg
610                 615                 620

Thr Cys Ser Arg Leu Leu Thr Pro Ser Ile His Leu Ile Ser Gly His
625                 630                 635                 640

Ala His Val Val Ser Gln Thr Ala Val Gln Val Ala Asp Val Leu
                645                 650                 655

Ser Lys Leu Leu Val Val Gly Ile Thr Asp Pro Asp Pro Asp Ile Arg
            660                 665                 670

Tyr Cys Val Leu Ala Ser Leu Asp Glu Arg Phe Asp Ala His Leu Ala
            675                 680                 685

Gln Ala Glu Asn Leu Gln Ala Leu Phe Val Ala Leu Asn Asp Gln Val
        690                 695                 700

Phe Glu Ile Arg Glu Leu Ala Ile Cys Thr Val Gly Arg Leu Ser Ser
705                 710                 715                 720

Met Asn Pro Ala Phe Val Met Pro Phe Leu Arg Lys Met Leu Ile Gln
                725                 730                 735

Ile Leu Thr Glu Leu Glu His Ser Gly Ile Gly Arg Ile Lys Glu Gln
                740                 745                 750

Ser Ala Arg Met Leu Gly His Leu Val Ser Asn Ala Pro Arg Leu Ile
        755                 760                 765

Arg Pro Tyr Met Glu Pro Ile Leu Lys Ala Leu Ile Leu Lys Leu Lys
770                 775                 780

Asp Pro Asp Pro Asp Pro Asn Pro Gly Val Ile Asn Asn Val Leu Ala
785                 790                 795                 800

Thr Ile Gly Glu Leu Ala Gln Val Ser Gly Leu Glu Met Arg Lys Trp
                805                 810                 815

Val Asp Glu Leu Phe Ile Ile Met Asp Met Leu Gln Asp Ser Ser
                820                 825                 830

Leu Leu Ala Lys Arg Gln Val Ala Leu Trp Thr Leu Gly Gln Leu Val
        835                 840                 845

Ala Ser Thr Gly Tyr Val Val Glu Pro Tyr Arg Lys Tyr Pro Thr Leu
850                 855                 860

Leu Glu Val Leu Leu Asn Phe Leu Lys Thr Glu Gln Asn Gln Gly Thr
865                 870                 875                 880
```

```
Arg Arg Glu Ala Ile Arg Val Leu Gly Leu Leu Gly Ala Leu Asp Pro
                885                 890                 895
Tyr Lys His Lys Val Asn Ile Gly Met Ile Asp Gln Ser Arg Asp Ala
                900                 905                 910
Ser Ala Val Ser Leu Ser Glu Ser Lys Ser Ser Gln Asp Ser Ser Asp
                915                 920                 925
Tyr Ser Thr Ser Glu Met Leu Val Asn Met Gly Asn Leu Pro Leu Asp
                930                 935                 940
Glu Phe Tyr Pro Ala Val Ser Met Val Ala Leu Met Arg Ile Phe Arg
945                 950                 955                 960
Asp Gln Ser Leu Ser His His Thr Met Val Gln Ala Ile Thr
                965             970                 975
Phe Ile Phe Lys Ser Leu Gly Leu Lys Cys Val Gln Phe Leu Pro Gln
                980                 985                 990
Val Met Pro Thr Phe Leu Asn Val Ile Arg Val Cys Asp Gly Ala Ile
                995                 1000                1005
Arg Glu Phe Leu Phe Gln Gln Leu Gly Met Leu Val Ser Phe Val
     1010                1015                1020
Lys Ser His Ile Arg Pro Tyr Met Asp Glu Ile Val Thr Leu Met
     1025                1030                1035
Arg Glu Phe Trp Val Met Asn Thr Ser Ile Gln Ser Thr Ile Ile
     1040                1045                1050
Leu Leu Ile Glu Gln Ile Val Val Ala Leu Gly Gly Glu Phe Lys
     1055                1060                1065
Leu Tyr Leu Pro Gln Leu Ile Pro His Met Leu Arg Val Phe Met
     1070                1075                1080
His Asp Asn Ser Pro Gly Arg Ile Val Ser Ile Lys Leu Leu Ala
     1085                1090                1095
Ala Ile Gln Leu Phe Gly Ala Asn Leu Asp Asp Tyr Leu His Leu
     1100                1105                1110
Leu Leu Pro Pro Ile Val Lys Leu Phe Asp Ala Pro Glu Ala Pro
     1115                1120                1125
Leu Pro Ser Arg Lys Ala Ala Leu Glu Thr Val Asp Arg Leu Thr
     1130                1135                1140
Glu Ser Leu Asp Phe Thr Asp Tyr Ala Ser Arg Ile Ile His Pro
     1145                1150                1155
Ile Val Arg Thr Leu Asp Gln Ser Pro Glu Leu Arg Ser Thr Ala
     1160                1165                1170
Met Asp Thr Leu Ser Ser Leu Val Phe Gln Leu Gly Lys Lys Tyr
     1175                1180                1185
Gln Ile Phe Ile Pro Met Val Asn Lys Val Leu Val Arg His Arg
     1190                1195                1200
Ile Asn His Gln Arg Tyr Asp Val Leu Ile Cys Arg Ile Val Lys
     1205                1210                1215
Gly Tyr Thr Leu Ala Asp Glu Glu Glu Asp Pro Leu Ile Tyr Gln
     1220                1225                1230
His Arg Met Leu Arg Ser Gly Gln Gly Asp Ala Leu Ala Ser Gly
     1235                1240                1245
Pro Val Glu Thr Gly Pro Met Lys Lys Leu His Val Ser Thr Ile
     1250                1255                1260
Asn Leu Gln Lys Ala Trp Gly Ala Ala Arg Arg Val Ser Lys Asp
     1265                1270                1275
Asp Trp Leu Glu Trp Leu Arg Arg Leu Ser Leu Glu Leu Leu Lys
```

```
                1280                1285                1290

Asp Ser Ser Ser Pro Ser Leu Arg Ser Cys Trp Ala Leu Ala Gln
    1295            1300            1305

Ala Tyr Asn Pro Met Ala Arg Asp Leu Phe Asn Ala Ala Phe Val
    1310            1315            1320

Ser Cys Trp Ser Glu Leu Asn Glu Asp Gln Gln Asp Glu Leu Ile
    1325            1330            1335

Arg Ser Ile Glu Leu Ala Leu Thr Ser Gln Asp Ile Ala Glu Val
    1340            1345            1350

Thr Gln Thr Leu Leu Asn Leu Ala Glu Phe Met Glu His Ser Asp
    1355            1360            1365

Lys Gly Pro Leu Pro Leu Arg Asp Asp Asn Gly Ile Val Leu Leu
    1370            1375            1380

Gly Glu Arg Ala Ala Lys Cys Arg Ala Tyr Ala Lys Ala Leu His
    1385            1390            1395

Tyr Lys Glu Leu Glu Phe Gln Lys Gly Pro Thr Pro Ala Ile Leu
    1400            1405            1410

Glu Ser Leu Ile Ser Ile Asn Asn Lys Leu Gln Gln Pro Glu Ala
    1415            1420            1425

Ala Ala Gly Val Leu Glu Tyr Ala Met Lys His Phe Gly Glu Leu
    1430            1435            1440

Glu Ile Gln Ala Thr Trp Tyr Glu Lys Leu His Glu Trp Glu Asp
    1445            1450            1455

Ala Leu Val Ala Tyr Asp Lys Lys Met Asp Thr Asn Lys Asp Asp
    1460            1465            1470

Pro Glu Leu Met Leu Gly Arg Met Arg Cys Leu Glu Ala Leu Gly
    1475            1480            1485

Glu Trp Gly Gln Leu His Gln Gln Cys Cys Glu Lys Trp Thr Leu
    1490            1495            1500

Val Asn Asp Glu Thr Gln Ala Lys Met Ala Arg Met Ala Ala Ala
    1505            1510            1515

Ala Ala Trp Gly Leu Gly Gln Trp Asp Ser Met Glu Glu Tyr Thr
    1520            1525            1530

Cys Met Ile Pro Arg Asp Thr His Asp Gly Ala Phe Tyr Arg Ala
    1535            1540            1545

Val Leu Ala Leu His Gln Asp Leu Phe Ser Leu Ala Gln Gln Cys
    1550            1555            1560

Ile Asp Lys Ala Arg Asp Leu Leu Asp Ala Glu Leu Thr Ala Met
    1565            1570            1575

Ala Gly Glu Ser Tyr Ser Arg Ala Tyr Gly Ala Met Val Ser Cys
    1580            1585            1590

His Met Leu Ser Glu Leu Glu Glu Val Ile Gln Tyr Lys Leu Val
    1595            1600            1605

Pro Glu Arg Arg Glu Ile Ile Arg Gln Ile Trp Trp Glu Arg Leu
    1610            1615            1620

Gln Gly Cys Gln Arg Ile Val Glu Asp Trp Gln Lys Ile Leu Met
    1625            1630            1635

Val Arg Ser Leu Val Val Ser Pro His Glu Asp Met Arg Thr Trp
    1640            1645            1650

Leu Lys Tyr Ala Ser Leu Cys Gly Lys Ser Gly Arg Leu Ala Leu
    1655            1660            1665

Ala His Lys Thr Leu Val Leu Leu Leu Gly Val Asp Pro Ser Arg
    1670            1675            1680
```

```
Gln Leu Asp His Pro Leu Pro Thr Val His Pro Gln Val Thr Tyr
1685                1690                1695

Ala Tyr Met Lys Asn Met Trp Lys Ser Ala Arg Lys Ile Asp Ala
1700                1705                1710

Phe Gln His Met Gln His Phe Val Gln Thr Met Gln Gln Gln Ala
1715                1720                1725

Gln His Ala Ile Ala Thr Glu Asp Gln Gln His Lys Gln Glu Leu
1730                1735                1740

His Lys Leu Met Ala Arg Cys Phe Leu Lys Leu Gly Glu Trp Gln
1745                1750                1755

Leu Asn Leu Gln Gly Ile Asn Glu Ser Thr Ile Pro Lys Val Leu
1760                1765                1770

Gln Tyr Tyr Ser Ala Ala Thr Glu His Asp Arg Ser Trp Tyr Lys
1775                1780                1785

Ala Trp His Ala Trp Ala Val Met Asn Phe Glu Ala Val Leu His
1790                1795                1800

Tyr Lys His Gln Asn Gln Ala Arg Asp Glu Lys Lys Lys Leu Arg
1805                1810                1815

His Ala Ser Gly Ala Asn Ile Thr Asn Ala Thr Thr Ala Ala Thr
1820                1825                1830

Thr Ala Ala Thr Ala Thr Thr Thr Ala Ser Thr Glu Gly Ser Asn
1835                1840                1845

Ser Glu Ser Glu Ala Glu Ser Thr Glu Asn Ser Pro Thr Pro Ser
1850                1855                1860

Pro Leu Gln Lys Lys Val Thr Glu Asp Leu Ser Lys Thr Leu Leu
1865                1870                1875

Met Tyr Thr Val Pro Ala Val Gln Gly Phe Phe Arg Ser Ile Ser
1880                1885                1890

Leu Ser Arg Gly Asn Asn Leu Gln Asp Thr Leu Arg Val Leu Thr
1895                1900                1905

Leu Trp Phe Asp Tyr Gly His Trp Pro Asp Val Asn Glu Ala Leu
1910                1915                1920

Val Glu Gly Val Lys Ala Ile Gln Ile Asp Thr Trp Leu Gln Val
1925                1930                1935

Ile Pro Gln Leu Ile Ala Arg Ile Asp Thr Pro Arg Pro Leu Val
1940                1945                1950

Gly Arg Leu Ile His Gln Leu Leu Thr Asp Ile Gly Arg Tyr His
1955                1960                1965

Pro Gln Ala Leu Ile Tyr Pro Leu Thr Val Ala Ser Lys Ser Thr
1970                1975                1980

Thr Thr Ala Arg His Asn Ala Ala Asn Lys Ile Leu Lys Asn Met
1985                1990                1995

Cys Glu His Ser Asn Thr Leu Val Gln Gln Ala Met Met Val Ser
2000                2005                2010

Glu Glu Leu Ile Arg Val Ala Ile Leu Trp His Glu Met Trp His
2015                2020                2025

Glu Gly Leu Glu Glu Ala Ser Arg Leu Tyr Phe Gly Glu Arg Asn
2030                2035                2040

Val Lys Gly Met Phe Glu Val Leu Glu Pro Leu His Ala Met Met
2045                2050                2055

Glu Arg Gly Pro Gln Thr Leu Lys Glu Thr Ser Phe Asn Gln Ala
2060                2065                2070

Tyr Gly Arg Asp Leu Met Glu Ala Gln Glu Trp Cys Arg Lys Tyr
2075                2080                2085
```

-continued

Met Lys Ser Gly Asn Val Lys Asp Leu Thr Gln Ala Trp Asp Leu
    2090            2095                2100

Tyr Tyr His Val Phe Arg Arg Ile Ser Lys Gln Leu Pro Gln Leu
    2105            2110                2115

Thr Ser Leu Glu Leu Gln Tyr Val Ser Pro Lys Leu Leu Met Cys
    2120            2125                2130

Arg Asp Leu Glu Leu Ala Val Pro Gly Thr Tyr Asp Pro Asn Gln
    2135            2140                2145

Pro Ile Ile Arg Ile Gln Ser Ile Ala Pro Ser Leu Gln Val Ile
    2150            2155                2160

Thr Ser Lys Gln Arg Pro Arg Lys Leu Thr Leu Met Gly Ser Asn
    2165            2170                2175

Gly His Glu Phe Val Phe Leu Leu Lys Gly His Glu Asp Leu Arg
    2180            2185                2190

Gln Asp Glu Arg Val Met Gln Leu Phe Gly Leu Val Asn Thr Leu
    2195            2200                2205

Leu Ala Asn Asp Pro Thr Ser Leu Arg Lys Asn Leu Ser Ile Gln
    2210            2215                2220

Arg Tyr Ala Val Ile Pro Leu Ser Thr Asn Ser Gly Leu Ile Gly
    2225            2230                2235

Trp Val Pro His Cys Asp Thr Leu His Ala Leu Ile Arg Asp Tyr
    2240            2245                2250

Arg Glu Lys Lys Lys Ile Leu Leu Asn Ile Glu His Arg Ile Met
    2255            2260                2265

Leu Arg Met Ala Pro Asp Tyr Asp His Leu Thr Leu Met Gln Lys
    2270            2275                2280

Val Glu Val Phe Glu His Ala Val Asn Asn Thr Ala Gly Asp Asp
    2285            2290                2295

Leu Ala Lys Leu Leu Trp Leu Lys Ser Pro Ser Ser Glu Val Trp
    2300            2305                2310

Phe Asp Arg Arg Thr Asn Tyr Thr Arg Ser Leu Ala Val Met Ser
    2315            2320                2325

Met Val Gly Tyr Ile Leu Gly Leu Gly Asp Arg His Pro Ser Asn
    2330            2335                2340

Leu Met Leu Asp Arg Leu Ser Gly Lys Ile Leu His Ile Asp Phe
    2345            2350                2355

Gly Asp Cys Phe Glu Val Ala Met Thr Arg Glu Lys Phe Pro Glu
    2360            2365                2370

Lys Ile Pro Phe Arg Leu Thr Arg Met Leu Thr Asn Ala Met Glu
    2375            2380                2385

Val Thr Gly Leu Asp Gly Asn Tyr Arg Ile Thr Cys His Thr Val
    2390            2395                2400

Met Glu Val Leu Arg Glu His Lys Asp Ser Val Met Ala Val Leu
    2405            2410                2415

Glu Ala Phe Val Tyr Asp Pro Leu Leu Asn Trp Arg Leu Met Asp
    2420            2425                2430

Thr Asn Thr Lys Gly Asn Lys Arg Ser Arg Thr Arg Thr Asp Ser
    2435            2440                2445

Tyr Ser Ala Gly Gln Ser Val Glu Ile Leu Asp Gly Val Glu Leu
    2450            2455                2460

Gly Glu Pro Ala His Lys Lys Thr Gly Thr Thr Val Pro Glu Ser
    2465            2470                2475

Ile His Ser Phe Ile Gly Asp Gly Leu Val Lys Pro Glu Ala Leu

|  |  |  |  |  | 2480 |  |  |  | 2485 |  |  |  | 2490 |  |
|---|---|---|---|---|---|---|---|---|---|---|---|---|---|---|
| Asn | Lys | Lys | Ala | Ile | Gln | Ile | Ile | Asn | Arg | Val | Arg | Asp | Lys | Leu |
|  |  |  |  |  | 2495 |  |  |  | 2500 |  |  |  | 2505 |  |
| Thr | Gly | Arg | Asp | Phe | Ser | His | Asp | Asp | Thr | Leu | Asp | Val | Pro | Thr |
|  |  |  |  |  | 2510 |  |  |  | 2515 |  |  |  | 2520 |  |
| Gln | Val | Glu | Leu | Leu | Ile | Lys | Gln | Ala | Thr | Ser | His | Glu | Asn | Leu |
|  |  |  |  |  | 2525 |  |  |  | 2530 |  |  |  | 2535 |  |
| Cys | Gln | Cys | Tyr | Ile | Gly | Trp | Cys | Pro | Phe | Trp |  |  |  |  |
|  |  |  |  |  | 2540 |  |  |  | 2545 |  |  |  |  |  |

MTOR KINASE-ASSOCIATED PROTEINS

RELATED APPLICATIONS

This application is a divisional of U.S. application Ser. No. 10/782,244, now U.S. Pat. No. 7,052,870, which claims the benefit of priority of U.S. Provisional Application No. 60/448,035 filed Feb. 18, 2003. The entire teachings of each of the referenced applications are incorporated herein by reference in their entirety.

FUNDING

Work described herein was supported by National Institutes of Health Grant RO1 AI47389. The United States government has certain rights in the invention.

BACKGROUND OF THE INVENTION

Cell growth is the fundamental biological process whereby cells accumulate mass and is an important determinant of the sizes of cells, organs, and organisms (Conlon, I. and Raff, M. (1999), Cell 96, 235-44; Dixon, D. and Fordham-Skelton, T. (1998), Curr. Opin. Plant Biol. 1, 1; Gomer, R. H. (2001), Nat. Rev. Mol. Cell Biol. 2, 48-54; Johnston, L. A. and Gallant, P. (2002), Bioessays 24, 54-64; Stocker, H. and Hafen, E. (2000), Curr. Opin. Genet. Dev. 10, 529-35). The mTOR pathway, along with the PI-3Kinase/PKB/PTEN axis, is emerging as a critical regulator of growth in mammals in response to nutrients, hormones and growth factors (Gingras, A. C., et al., (2001), Genes Dev. 15, 807-26; Kozma, S. C. and Thomas, G. (2002), Bioessays 24, 65-71; Schmelzle, T. and Hall M. N. (2000), Cell 103, 253-62). The central component of the pathway, mTOR (also known as RAFT1 or FRAP, the sequence of which is provided as SEQ ID NO: 52), was discovered during studies into the mechanism of action of rapamycin (Brown, E. J., et al. (1994), Nature 369, 756-758; Sabatini, D. M., et al. (1994), Cell 78, 35-43; Sabers, C. J., et al. (1995), J. Biol. Chem. 270, 815-822), an anti-proliferative drug with valuable immunosuppressive and anti-cancer clinical applications (Saunders, R. N., et al. (2001), Kidney Int. 59, 3-16; Vogt, P. K. (2001), Trends Mol. Med. 7, 482-4). mTOR is a member of the PIK-related family of large protein kinases (Keith, C. T. and Schreiber, S. L. (1995), Science 270, 50-1) and mediates the phosphorylation of at least two regulators of protein synthesis and cell growth: S6 Kinase 1 (S6K1) and an inhibitor of translation initiation, the eIF-4E binding protein 1 (4E-BP1) (Brunn, G. J., et al. (1997), Science 277, 99-101; Burnett, P. E., et al. (1998), PNAS 95, 1432-1437; Isotani, S., et al. (1999), J. Biol. Chem. 274, 34493-8). Recent work suggests that deregulation of the mTOR pathway plays a role in the pathogenesis of human disease, as the pathway is constitutively active in tuberous sclerosis (Goncharova, E. A. (2002), J. Biol. Chem. 277, 30958-67; Kwiatkowski, D. J., et al. (2002), Hum. Mol. Genset 11, 525-34), a tumor-prone syndrome caused by mutations in the TSC1 (van Slegtenhorst, M., et al. (1997), Science 277, 805-8) or TSC2 (Consortium, T. E. C. T. S. (1993), Cell 75, 1305-15) genes. Exactly how the mTOR, TSC1/2 and PI-3K/Akt/PTEN pathways interconnect is unknown, but it is likely that these systems integrate growth factor- and nutrient-derived signals to determine overall growth rates. The mTOR pathway is particularly sensitive to the levels of nutrients, such as amino acids (Hara, K., et al. (1998), J. Biol. Chem. 273, 14484-94) and glucose (Dennis, P. B., et al. (2001), Science 294, 1102-5; Kim, D. H., et al. (2002), Cell 110, 163-75), but the molecular mechanisms by which nutrients regulate mTOR are to be understood.

It would be helpful to have methods and compositions that regulate the mTOR pathway, which would be useful as therapeutic approaches for diseases such as cancer, diabetes, and cardiovascular diseases.

SUMMARY OF THE INVENTION

The present invention relates to the discovery of two mTOR-associated proteins (mTOR-APs), termed GβL (G protein β-subunit-like protein) and rictor (rapamycin insensitive companion of mTOR). GβL and rictor are screening targets for the identification and development of novel pharmaceutical agents which modulate the activity of these mTOR-APs. Activities of the mTOR-AP include, but are not limited to, forming a complex with an mTOR protein, activation of the mTOR kinase, modulating signaling through the mTOR pathway, stimulating phosphorylation of PKCα, modulating the actin cytoskeleton organization, and inhibiting or reducing cell growth or proliferation.

In certain embodiments, the invention provides isolated mTOR-AP (e.g., GβL and rictor) polypeptides. Polypeptide fragments or variants of an mTOR-AP polypeptide are additional embodiments of this invention. The invention additionally relates to isolated nucleic acids (e.g., DNA, RNA) encoding an mTOR-AP polypeptide, mTOR-AP fragments, and mTOR-AP variants. The invention further relates to nucleic acids that are complementary to nucleic acid encoding an mTOR-AP polypeptide. In certain embodiments, the invention relates to nucleic acid which hybridizes under high stringency conditions to all or a portion of nucleic acid encoding an mTOR-AP polypeptide.

In certain embodiments, the invention provides expression vectors comprising nucleic acid encoding an mTOR-AP polypeptide, such as a GβL polypeptide and a rictor polypeptide. Host cells comprising exogenous nucleic acid (e.g., DNA, RNA) encoding an mTOR-AP polypeptide, such as host cells containing an expression vector comprising nucleic acid encoding an mTOR-AP polypeptide, are also the subject of this invention.

In certain embodiments, the invention relates to a method for producing an mTOR-AP polypeptide, such as a method of producing a GβL polypeptide or a rictor polypeptide in isolated host cells containing a vector expressing a GβL or a rictor polypeptide. In certain aspects, the invention relates to an antibody that is specific for a GβL polypeptide or a rictor polypeptide of the invention.

In certain embodiments, the invention provides a method for detecting the presence of the subject mTOR-AP polypeptide (e.g., GβL or rictor) in a sample. This method comprises: a) contacting the sample with an antibody which selectively binds to the mTOR-AP polypeptide; and b) determining whether the antibody binds to the mTOR-AP polypeptide in the sample. In another embodiment, the invention provides a kit for detecting an mTOR-AP polypeptide. The kit comprises an antibody of the invention and a detectable label for detecting said antibody.

In certain embodiments, the invention provides a method for detecting the presence of the subject mTOR-AP nucleic acid (e.g., GβL or rictor) in a sample. This method comprises: a) contacting the sample with an mTOR-AP probe or primer; and b) determining whether the probe or primer binds to the mTOR-AP nucleic acid in the sample. In another embodiment, the invention provides a kit for detecting an mTOR-AP nucleic acid. The kit comprises an mTOR-AP nucleic acid as a probe or a primer and instructions for use.

In certain embodiments, the invention provides an isolated, purified or recombinant complex comprising an mTOR polypeptide and an mTOR-associated protein (mTOR-AP). In one specific embodiment, the complex of the invention comprises an mTOR polypeptide and a GβL polypeptide. In this specific embodiment, the complex further comprises a raptor polypeptide in addition to the mTOR polypeptide and the GβL polypeptide. In another specific embodiment, the complex of the invention comprises an mTOR polypeptide and a rictor polypeptide. In this specific embodiment, the complex further comprises a GβL polypeptide in addition to the mTOR polypeptide and the rictor polypeptide.

In certain embodiments, the invention provides a method of screening for compounds which modulate the activity or expression of an mTOR-AP, such as a GβL protein or a rictor protein. Compounds (e.g., agonists or antagonists) which modulate the mTOR-AP activity or expression are also the subject of this invention.

In certain embodiments, the invention provides a method of inhibiting aberrant activity of an mTOR-AP (e.g., a GβL protein or a rictor protein) in a cell. In this method, a cell is contacted with a compound that modulates the activity or expression of the mTOR-AP, in an amount which is effective to reduce or inhibit the aberrant activity of the mTOR-AP. An exemplary compound includes, but is not limited to, a peptide, a phosphopeptide, a small organic molecule, an antibody, and a peptidomimetic. In this method, a specific cell is a cancer cell. A preferred cell is a human cell.

In certain embodiments, the invention provides a method of treatment for a disease (disorder or condition) affected by aberrant activity of an mTOR-AP (e.g., GβL or rictor). Such disease (disorder or condition) is responsive to mTOR-AP modulation. In this method, a compound that modulates the mTOR-AP activity or expression is administered to an individual (subject or patient) in need thereof, in a therapeutically effective amount, such that the aberrant activity or expression of the mTOR-AP is reduced or inhibited. Examples of such diseases include, but are not limited to, cancer, diabetes, and cardiovascular diseases (e.g., restenosis).

In another embodiment, the invention provides a transgenic mouse having germline and somatic cells comprising a chromosomally incorporated transgene that disrupts the genomic mTOR-AP gene (e.g., GβL or rictor) and inhibits expression of said gene. In certain cases, the mTOR-AP gene is disrupted by insertion of a selectable marker sequence. Optionally, the transgenic mouse of the invention exhibits increased or decreased susceptibility to the formation of tumors as compared to the wildtype mouse. The transgenic mouse can be homozygous r heterozygous for the disruption.

In other embodiments, the invention relates to use of a GβL polypeptide or a rictor polypeptide, a nucleic acid encoding a GβL or a rictor polypeptide, or an antibody specific for a GβL or a rictor polypeptide, and a compound which modulates GβL or rictor activity in the manufacture of a medicament for the treatment of diseases affected by GβL and/or rictor activity (e.g., cancer, diabetes, or cardiovascular disorders). GβL and/or rictor nucleic acids and the proteins encoded thereby, as well as the fragments and variants thereof, can be used as therapeutic drugs, drug targets, and for diagnostic purposes.

Figure 1:
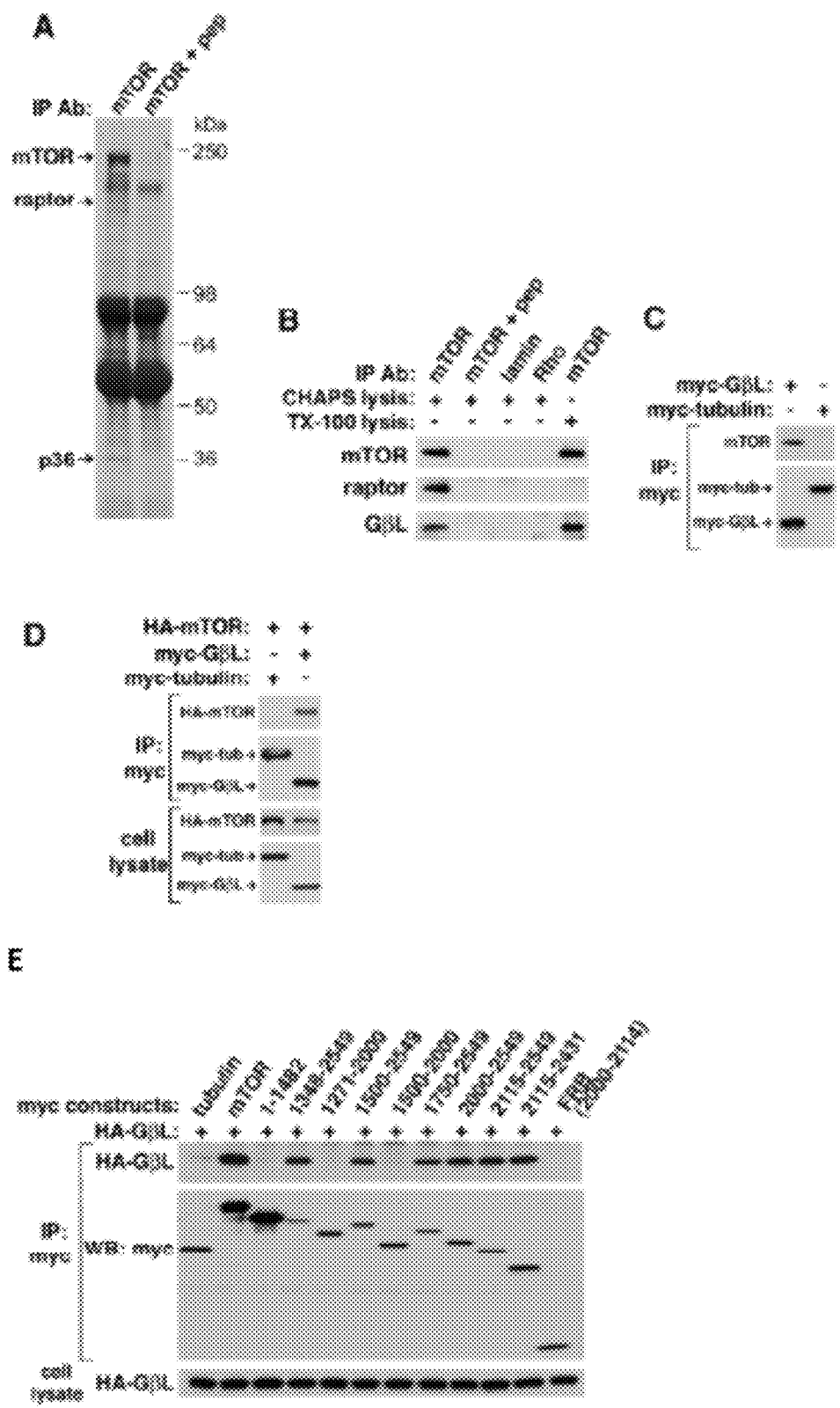
FIGS. 1A-1E show identification of GβL as an mTOR-associated protein. (A) Coomassie blue stained SDS-PAGE analysis of mTOR immunoprecipitates prepared from HEK-293T cell extracts in the absence or presence (+pep) of the blocking peptide for the anti-mTOR antibody. Quantitation by densitometry (Kim et al., 2002) of the bands corresponding to mTOR and p36 reveals a ratio of 1.0 mTOR to 0.9 p36. (B) Specific in vivo interaction between mTOR and GβL. A polyclonal anti-GβL antibody recognizes GβL in mTOR immunoprecipitates prepared from cells lysed in buffers containing either 0.3% CHAPS or 1% Triton X-100 but not in immunoprecipitates prepared with the indicated control antibodies or in the presence of the blocking peptide for the mTOR antibody. (C) Endogenous mTOR interacts with recombinant GβL but not γ-tubulin. Immunoblotting for mTOR and myc-tagged proteins was performed on anti-myc immunoprecipitates prepared from HEK-293T cells expressing myc-GβL or myc-γ-tubulin. (D) Recombinant versions of mTOR and GβL interact with each other. Immunoblotting of HA-mTOR and myc-tagged proteins was performed on myc immunoprecipitates prepared from HEK-293T cells coexpressing HA-mTOR with either myc-GβL or myc-γ-tubulin. (E) GβL interacts with the mTOR kinase domain. Myc-tagged full-length mTOR, its indicated fragments or γ-tubulin were co-expressed with HA-GβL, and anti-myc immunoprecipitates analyzed by anti-HA and anti-myc immunoblotting.

Immunoblotting was used to analyze the amounts of endogenous raptor and HA-GβL recovered in myc immunoprecipitates prepared from HEK-293T cells expressing myc-mTOR or myc-γ-tubulin with or without HA-GβL. (D) GβL has independent binding sites for mTOR and raptor. Immunoblotting was used to determine the amounts of endogenous mTOR and raptor in anti-myc immunoprecipitates prepared from HEK-293T cells expressing HA-tagged γ-tubulin, or wild-type or mutant GβL. (E) GβL promotes the binding of raptor to the mTOR kinase domain. Immunoblotting was used to determine the amounts of endogenous raptor and HA-tagged wild-type or mutant GβL in myc-immunoprecipitates prepaed from HEK-293T cells co-expressing a myc-mTOR fragment (amino acids 2115 to 2549) and the indicated GβL variants. (F) The capacity of GβL to stimulate the mTOR was co-expressed with HA-tagged wild-type or mutant GβL and its kinase activity determined as in FIG. 2D using myc-immunoprecipitates prepared from cells lysed in the Triton X-100-containing Buffer A (Kim et al., 2002).

FIGS. 4A-4E show that regulation of mTOR activity by raptor requires GβL. (A) Disruption of GβL-raptor interaction leads to an increase in S6K1 phosphorylation. Immunoblotting was used to determine the phosphorylation level of S6K1 in myc-immunoprecipitates prepared from HEK-293T cells co-expressing myc-S6K1 and the indicated HA-tagged variants of GβL. (B) The GβL-raptor interaction is inhibitory for S6K1 phosphorylation. The phosphorylation level of S6K1 was analyzed, as in (A), in myc-immunoprecipitates from HEK-293T cells co-expressing myc-S6K1 with HA-tagged wild type or mutant raptor (Kim et al., 2002), and wild type or mutant GβL. (C) The GβL-raptor interaction is part of the nutrient-sensitive mechanism necessary to stabilize the mTOR-raptor association. Cells co-expressing HA-mTOR with the indicated myc-tagged GβL variants were treated with (+) or without (−) DSP before lysis as described (Kim et al., 2002). Immunoblot analyses were used to determine the amounts of endogenous raptor and myc-GβL in HA-immunoprecipitates and the expression levels of myc-GβL in cellular lysates. (D) GβL and raptor have opposite effects on the mTOR kinases activity. Myc-mTOR kinase activity toward GST-S6K1 was determined as in FIG. 2D from HEK-293T cells co-expressing myc-mTOR with the indicated HA-tagged GβL and/or raptor variants. (E) Model for regulation of mTOR by GβL and raptor.

FIGS. 5A-5C show the human p200 mRNA sequence (SEQ ID NO: 1).

Figure 6B:
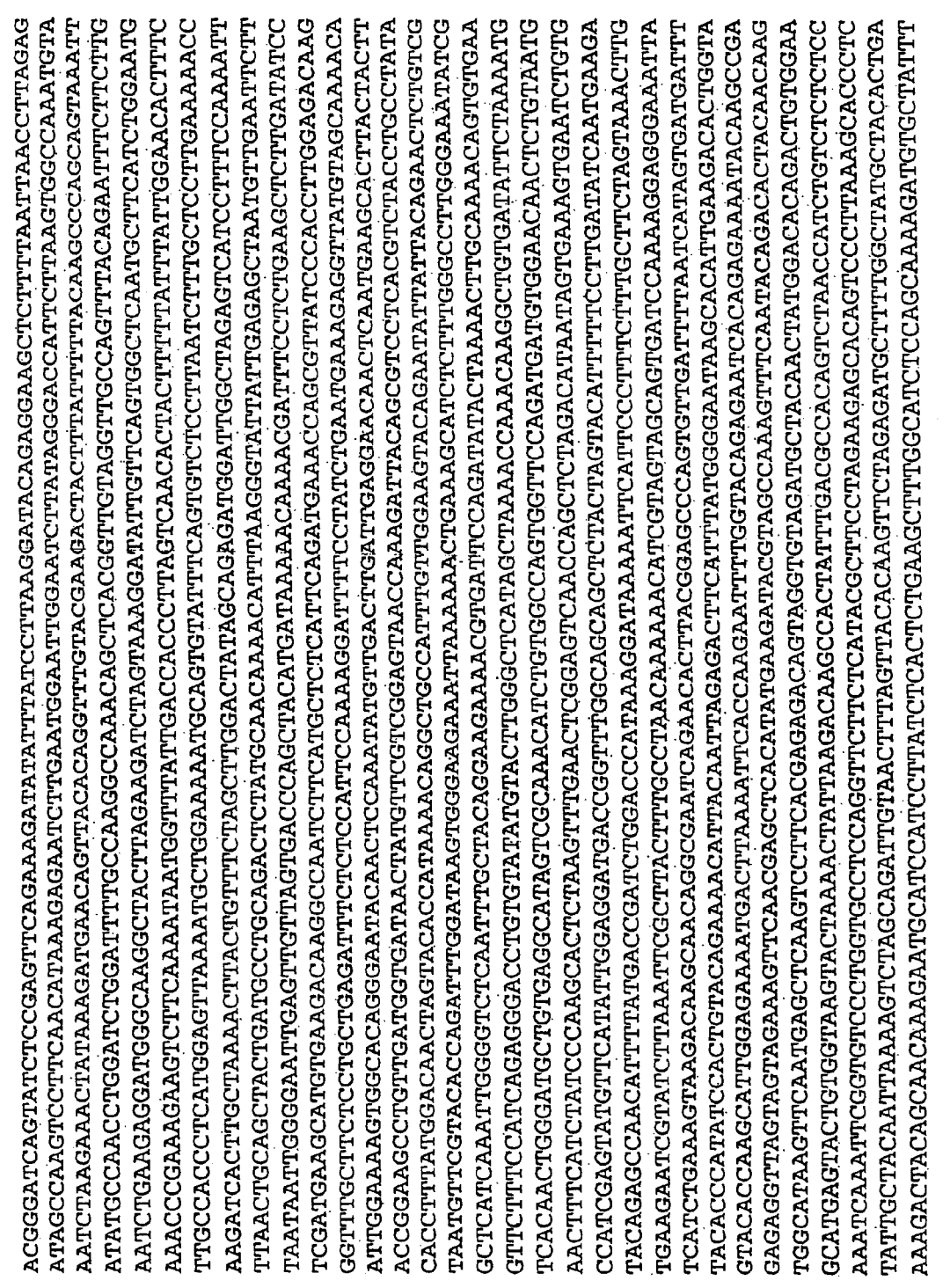

FIGS. 6A-6C show the human p200 ORF sequence (SEQ ID NO: 2).

FIGS. 7A and 7B show the p200 amino acid sequence (SEQ ID NO: 3).

FIG. 8 shows the human GβL mRNA sequence (SEQ ID NO: 4).

FIGS. 9A and 9B show the GβL ORF sequence without UTRs (SEQ ID NO: 5).

FIG. 10 shows the GβL amino acid sequence (SEQ ID NO: 6).

FIGS. 11A-11D show that rictor is a novel mTOR-associated protein. (A) Silver stain of SDS-PAGE analysis of mTOR immunoprecipitates prepared from HeLa cells lysed in a CHAPS- or Triton X-100-containing buffer. (+) indicates inclusion of the blocking peptide for the mTOR antibody during the immunoprecipitation. The ~200 kDa band corresponds to rictor and a non-specific band (NS) obscures raptor. (B) Rictor homologues share common domain architectures. Analyses of indicated rictor homologues identified seven domains with sequence conservation and similar relative locations within each protein and are shown schematically as boxes. Domain five is repeated four times within each of the homologues and the multiple sequence alignment shows the sequence pattern of this repeat. Sequences with the following accession numbers were used to create the alignment: *D. melanogaster*, AAQ22398.1; *A. gambiae*, XP_309233.1; *H. sapiens*, AY515854; *D. discoidieum*, AAC35553.1; *S. pombe*, NP_596021.1; *S. cerevisiae*; NP_011018.1. (C) Specific interaction between endogenous mTOR and rictor. Immunoprecipitates prepared with the indicated antibodies were analyzed by immunoblotting for mTOR, rictor and raptor. Prior to use cells were treated with 5 μM Antimycin A for 15 min (Antimy), 20 nM rapamycin for 15 min (Rapa), deprived of leucine for 90 min (−Leu), or deprived of leucine and stimulated with 52 μg/ml leucine for 10 min (−Leu+Leu). (D) Endogenous mTOR interacts with recombinant rictor and raptor. Cellular lysates and mTOR immunoprecipitates prepared from HEK293T cells expressing myc-rictor, myc-raptor, or myc-GCP3 were analyzed by immunoblotting for myc-tagged proteins. In parallel, anti-myc immunoprecipitates were analyzed by immunoblotting for mTOR.

Figure 12:
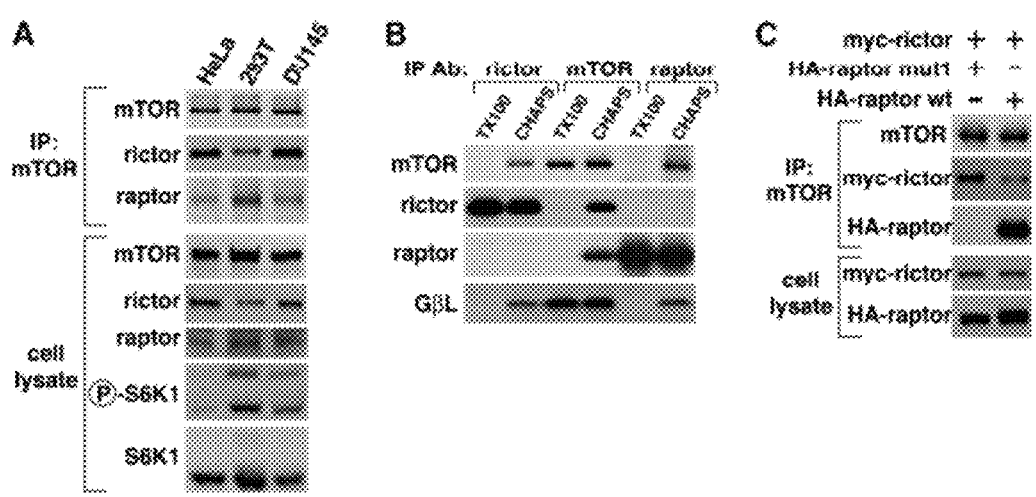

FIGS. 12A-12C show that rictor and raptor define two distinct mTOR-containing complexes. (A) Immunoblot analyses for indicated proteins of mTOR immunoprecipitates and cell lysates prepared from HeLa, HEK293T, and DU145 cells. Equal amounts of total protein were analyzed from each cell type. (B) Immunoblot analyses for the presence of the indicated components of the mTOR signaling complex in immunoprecipitates prepared from HEK293T cell lysates with antibodies against rictor, mTOR, or raptor. (C) Recombinant wild type raptor but not a mutant raptor suppresses the binding of rictor to mTOR. mTOR immunoprecipitates prepared from HEK293T cells expressing the indicated tagged proteins were analyzed by immunoblotting with anti-myc and anti-HA antibodies.

FIGS. 13A-13E show that rictor does not participate in rapamycin-sensitive mTOR functions. (A) The sensitivity of the raptor-mTOR interaction to rapamycin depends on the presence of phosphate-containing molecules in the lysis buffer. mTOR immunoprecipitates prepared from cells treated with or without 20 nM rapamycin for 10 min and lysed in a phosphate-containing or phosphate-free buffer were analyzed by immunoblotting for the indicated proteins. (B) Raptor and mTOR, but not rictor, co-purify with FKBP 12-rapamycin. Anti-HA immunoprecipitates prepared from HEK293T cells expressing HA-FKBP 12 and treated with or without 20 nM rapamycin for 15 min were analyzed by immunoblotting for the indicated proteins. (C) Suppression of rictor expression slightly increases the amount of raptor in the mTOR complex and S6K1 activity. mTOR immunoprecipitates and cell lysates prepared from HEK293T or HeLa cells transfected with siRNAs targeting lamin or rictor were analyzed by immunoblotting for the indicated proteins. (D) Suppression of *Drosophila* rictor expression increases the phosphorylation state of dS6K. The indicated dsRNAs were applied to *Drosophila* S2 cells and cell lysates were analyzed by immunoblotting with the mammalian phospho-specific S6K1 and *Drosophila* S6K antibodies. (E) The rictor-containing mTOR complex does not phosphorylate S6K1. Immunoprecipitates prepared with the indicated antibodies were used in mTOR kinase assays using S6K1 as a substrate. Where indicated immunoprecipitates were treated with 100 nM FKBP12-rapamycin for 40 min before the start of the assays. Immunoblotting was used to monitor the levels of rictor, mTOR, and raptor in the kinase reactions.

FIGS. 14A-14C show that rictor and mTOR, but not raptor, regulate the PKCα phosphorylation state in human and *Drosophila* cells. (A) siRNA-mediated reduction in the expression of total PKCα in HeLa cells also reduces the immunoblot signal from a phosphospecific antibody recognizing phospho-S657 of PKCα but does not affect the levels of S6K1. (B) Immunoblotting was used to analyze the phosphorylation states of PKCα and S6K1 in HeLa cells with reduced expression of rictor, raptor, or mTOR or treated with rapamycin. Lentiviruses were used to express siRNAs targeting rictor, raptor, mTOR or luciferase. (C) dsRNAs corresponding to the genes for the indicated proteins were applied to S2 Drosophila cells. After 4 days lysates were prepared and analyzed by immunoblotting for dPKCα and phospho-dPKCα levels.

Figure 15B:
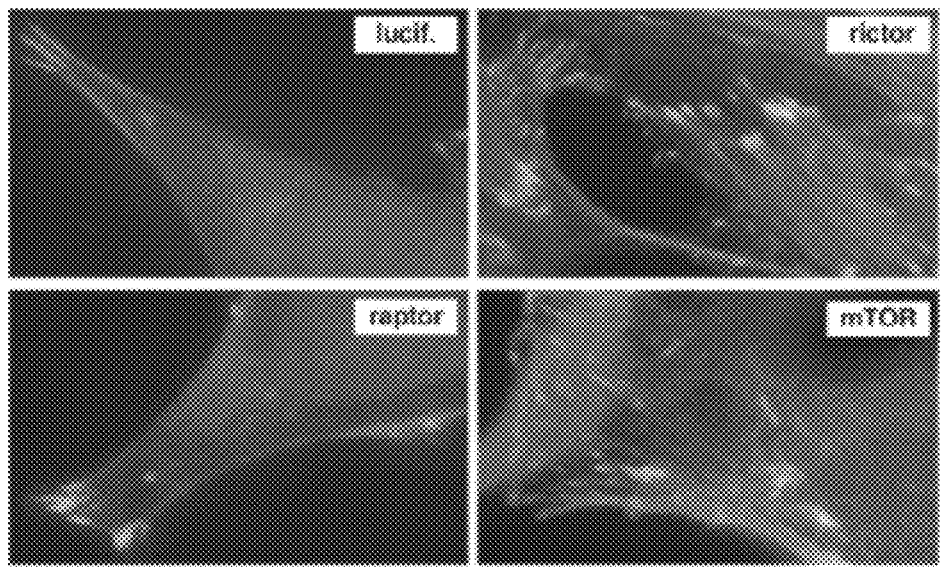
Figure 15C:
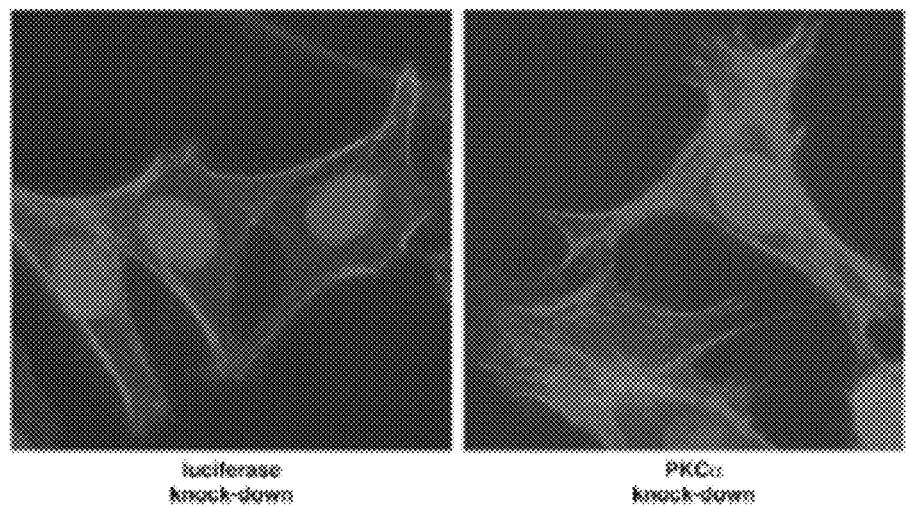

FIGS. 15A-15C show that rictor, mTOR and PKCα regulate the organization of the actin cytoskeleton. (A) Staining for actin (red), paxillin (green) and DNA (blue) reveals the organization of the actin cytoskeleton in HeLa cells transduced with the siRNA-expressing lentiviruses described in FIG. 14A. Arrows point to bundles of actin fibers. Images captured with a 60× objective are shown. (B) Higher magnification of portions of the merged images from FIG. 15A. (C) Like cells with reduced rictor expression, cells with reduced expression of PKCα have an altered actin cytoskeleton.

FIGS. 16A-16D that mTOR regulates the rictor phosphorylation state. (A) HeLa cells with reduced expression of mTOR or of a control protein were metabolically labeled with $^{32}P$ and the level of phosphorylated rictor determined by immunoprecipitation followed by autoradiography and immunoblotting for the indicated proteins. (B) The mobility of rictor in SDS-PAGE is affected by mTOR. HeLa cells with siRNA-mediated reductions in mTOR or controls were analyzed by immunoblotting for mTOR, rictor, and raptor. (C) The phosphorylation state of rictor affects its mobility in SDS-PAGE. Rictor immunoprecipitates were incubated with or without calf intestinal phosphatase (CIP) or heat inactivated CIP and analyzed by SDS-PAGE and immunoblotting for rictor. (D) Osmotic stress increases the mobility of rictor in SDS-PAGE. Lysates of HeLa cells exposed for 1 hr to 20 nM rapamycin, 20 nM LY294002, 100 mM 2 deoxyglucose (2-DG), medium without leucine or glucose, or medium without leucine or glucose followed by the readdition of the missing component for 10 minutes were analyzed by immunoblotting for rictor.

FIG. 17 shows the amino acid sequence of the GβL protein and the seven WD40 repeats in this protein.

FIG. 18 shows the structural model of the GβL protein.

FIG. 19 shows that GβL interacts with the mTOR kinase domain. Myc-tagged full-length mTOR, its indicated fragments, or γ-tubulin were coexpressed with HA-GβL, and anti-myc immunoprecipitates were analyzed by anti-HA and anti-myc immunoblotting.

DETAILED DESCRIPTION OF THE INVENTION

The present invention is based in part on Applicants' discovery that two proteins (designated GβL and rictor) associate with the mTOR kinase and participate in the mTOR signaling pathway. As described herein, the term "mTOR-associated protein" or "mTOR-AP" refers to a protein capable of interacting with and/or binding to an mTOR polypeptide. Generally, the mTOR-AP may interact directly or indirectly with the mTOR polypeptide. According to the application, specific types of the mTOR-AP are GβL polypeptides and rictor polypeptides.

In one aspect, the present invention relates to a GβL protein. As described herein, GβL acts to positively regulate the mTOR pathway by stimulating (activating) mTOR kinase activity and also mediates raptor-mTOR interaction. This protein interacts strongly with the C-terminal portion of mTOR (approximately amino acid residues 1348-2549) but does not interact with the N-terminal amino acid residues of mTOR. GβL has been shown to form a complex with mTOR (a GβL-mTOR complex) and, complex with mTOR and raptor (a GβL-mTOR-raptor complex). In the GβL-mTOR complex, GβL is linked to the mTOR kinase domain. Through its role as an activator of mTOR kinase activity, GβL plays an essential positive role in controlling cell growth and, thus, is a target that can, in turn, be regulated in order to alter (enhance or decrease) cell growth.

Certain embodiments of the present invention provide isolated GβL, alone, in complex with mTOR (linked to the mTOR kinase domain to form a GβL-mTOR complex) or in complex with mTOR kinase and raptor (a GβL-mTOR-raptor complex), the formation of which is necessary for raptor to inhibit the mTOR pathway (inhibit mTOR kinase activity). As shown herein, GβL mediates interaction between raptor and the mTOR kinase domain.

In another aspect, the present invention relates to a rictor protein (also referred to as a p200 protein). As described herein, mTOR also exists as part of a distinct complex defined by the novel protein rictor (rapamycin insensitive companion of mTOR). For example, the rictor-containing mTOR complex contains GβL but not raptor and it neither regulates the mTOR effector S6K1 nor is it a target of rapamycin. Through a rapamycin-insensitive and raptor-independent pathway, the rictor-containing complex modulates the phosphorylation state of Protein Kinase C alpha (PKCα) and the organization of the actin cytoskeleton. Thus, the mTOR pathway has both rapamycin-sensitive and rapamycin-insensitive functions. The latter one may be unrelated to mass accumulation and of different therapeutic interest.

Certain embodiments of the present invention provide isolated rictor, alone, in complex with mTOR, or in complex with mTOR kinase and GβL, the formation of which is necessary for rictor to modulate signaling through the mTOR pathway, such as phosphorylation of PKCα and the organization of the actin cytoskeleton.

Raptor (regulated associated protein of TOR) is a subunit of an mTOR-containing complex whose association with mTOR is modulated by nutrients and which regulates the mTOR kinase activity (Kim, D. H., et al. (2002), Cell 110, 163-75). Hara et al. independently identified the same interacting protein and adopted the raptor name (Hara, K., et al. (2002), Cell 110, 177-89). Raptor is a large protein of 149 kDa in molecular weight and contains an N-terminal RNC (Raptor N-terminal Conserved) domain found in all its eukaryotic homologues, three HEAT repeats following the RNC, and seven WD-40 repeats in the C-terminal third of the protein (Kim, D. H., et al. (2002), Cell 110, 163-75). The mTOR-binding site on raptor is not easily defined and, based on mutagenesis and truncation studies, may require the overall confrontation of raptor and/or multiple contacts between the proteins. Previously, Applicants proposed that raptor has at least two functions in the mTOR pathway. It clearly has a positive role within cells in maintaining an active mTOR pathway, as revealed by the inhibitory effects of reducing raptor expression on S6K1 activity and cell size (Kim, D. H., et al. (2002), Cell 110, 163-75). Raptor over-expression also stimulates the kinase activity of recombinant mTOR towards S6K1 and 4E-BP1, suggesting that raptor may be an adaptor protein that recruits mTOR substrates to the mTOR kinase domain (Hara, K., et al. (2002), Cell 110, 177-89). In addition to a positive function for a raptor, Applicants proposed that raptor also negatively regulates the mTOR kinase. Conditions that inhibit the pathway, such as nutrient deprivation, stabilized the raptor-mTOR association and inhibited the kinase activity of endogenous mTOR, and raptor over expression decreased the phosphorylation state of S6K1 within cells and the mTOR kinase activity in vitro (Kim, D. H., et al. (2002), Cell 110, 163-75). These results imply that regulation of mTOR kinase activity is complex and may be difficult to understand without knowledge of how mTOR and raptor interact with each other or with unidentified components of the complex that may affect the regulatory function(s) of raptor.

Exemplary mTOR-AP Nucleic Acids and Polypeptides

The present invention provides nucleic acids and the polypeptides encoded thereby relating to two mTOR-associated proteins (mTOR-APs), termed GβL and rictor. Described herein are isolated GβL polypeptides and rictor polypeptides, fragments and variants thereof; isolated nucleic acids (e.g., DNA, RNA) encoding GβL and rictor polypeptides, fragments and variants thereof; methods of producing GβL and rictor polypeptides; and methods in which GβL and rictor polypeptides are used. Such nucleic acids and polypeptides are of eukaryotic origin, such as mammalian origin (e.g., mouse or human).

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotides. The terms "protein" and "polypeptide" are used interchangeably herein.

In some aspects, the invention provides GβL and rictor nucleic acid sequences and proteins encoded thereby, as well as oligonucleotides that are portions of the nucleic acid sequences, antibodies that bind the encoded proteins, screening assays to identify agents that modulate activity of GβL, rictor or both, and/or biological events affected by GβL, rictor or both. These compounds may be used in the treatment and/or prophylaxis of diseases that are responsive to mTOR-AP modulation, for example, cancer and diabetes.

In one aspect, the invention provides an isolated nucleic acid comprising a nucleic acid which hybridizes under high stringency conditions to a nucleic acid having the sequence of SEQ ID NO: 2 or a sequence complementary thereto or having the sequence of SEQ ID NO: 4 or a sequence complementary thereto. In a further embodiment, the invention is an isolated nucleic acid that is at least about 70%, 80%, 90%, 95%, 97-98%, or greater than 99% identical to a sequence corresponding to at least about 12, at least about 15, at least about 25, at least about 40, at least about 100, at least about 300, at least about 500, at least about 1000, or at least about 2100 consecutive nucleotides up to the full length of SEQ ID NO: 2 or 4, or a sequence complementary thereto.

In one specific embodiment, nucleic acids exhibit one of the foregoing levels of identity to SEQ ID NO: 1 or 2 and encode polypeptides that also exhibit substantially the same activity or function as a rictor protein encoded by SEQ ID NO: 3. In another specific embodiment, nucleic acids exhibit one of the foregoing levels of identity to SEQ ID NO: 4 or 5 and encode polypeptides that also exhibit substantially the same activity or function as a GβL protein encoded by SEQ ID NO: 6.

Isolated nucleic acids of the present invention are substantially free from unrelated nucleic acids as well as contaminating polypeptides, nucleic acids and other cellular material that normally are associated with the nucleic acid in a cell or that are associated with the nucleic acid in a library.

In other embodiments, the invention provides expression vectors (constructs) comprising: (a) a nucleic acid which hybridizes under high stringency conditions to a sequence of SEQ ID NO: 2 or 4, or a nucleotide sequence that is at least about 70%, 80%, 90%, 95%, 97-98%, or greater than 99% identical to a sequence that is at least about 12, at least about 15, at least about 25, at least about 40, at least about 100, at least about 300, at least about 500, at least about 1000, or at least about 2100 consecutive nucleotides up to the full length of SEQ ID NO: 2 or 4, or a sequence complementary thereto; and (b) a transcriptional regulatory sequence operably linked to the nucleotide sequence. In certain embodiments, an expression vector of the present invention additionally comprises a transcriptional regulatory sequence, e.g., at least one of a transcriptional promoter or transcriptional enhancer sequence, which regulatory sequence is operably linked to a rictor or GβL sequence. In another embodiment, the nucleic acid may be included in an expression vector capable of replicating in and expressing the encoded rictor or GβL polypeptide in a prokaryotic or eukaryotic cell. In a related embodiment, the invention provides a host cell transfected with the expression vector.

Any of a wide variety of expression control sequences that control the expression of a DNA sequence when operatively linked to it may be used in these vectors to express DNA sequences encoding a rictor or GβL polypeptide. Such useful expression control sequences include, for example, the early and late promoters of SV40, tet promoter, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

As will be apparent, the subject gene constructs can be used to express rictor or GβL polypeptides in cells propagated in culture, e.g., to produce proteins or polypeptides, including fusion proteins or polypeptides, for purification.

This invention also pertains to a host cell transfected with a recombinant gene comprising a coding sequence for the subject rictor or GβL polypeptides. The host cell may be any prokaryotic or eukaryotic cell. For example, a polypeptide of the present invention may be expressed in bacterial cells (e.g., *E. coli*), insect cells (e.g., using a baculovirus expression system), yeast, avian, or mammalian cells (e.g., human cells such as 293T, HeLa).

Accordingly, the present invention further pertains to methods of producing the subject rictor or GβL polypeptides. For example, a host cell transfected with an expression vector encoding a rictor or GβL polypeptide can be cultured under appropriate conditions to allow expression of the polypeptide to occur. The polypeptide may be secreted and isolated from a mixture of cells and medium containing the polypeptide. Alternatively, the polypeptide may be retained cytoplasmically and the cells harvested, lysed and the protein isolated. A cell culture includes host cells, media and other byproducts.

Suitable media for cell culture are well known in the art. The polypeptide can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the polypeptide. In one embodiment, the rictor or GβL polypeptide is a fusion protein containing a domain which facilitates its purification, such as a rictor-GST or GβL-GST fusion protein, rictor-intein or GβL-intein fusion protein, rictor-cellulose binding domain or GβL-cellulose binding domain fusion protein, and rictor-polyhistidine or GβL-polyhistidine fusion protein.

A nucleotide sequence encoding a rictor or GβL polypeptide can be used to produce a recombinant form of the protein via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial) cells, are standard procedures.

A recombinant rictor or GβL nucleic acid can be produced by ligating the cloned gene, or a portion thereof, into a vector suitable for expression in either prokaryotic cells, eukaryotic cells, or both. Expression vehicles for production of recombinant rictor or GβL polypeptides include plasmids and other vectors. For instance, suitable vectors for the expression of a rictor or GβL polypeptide include plasmids of the types: pBR322-derived plasmids, pEMBL-derived plasmids, pEX-derived plasmids, pBTac-derived plasmids and pUC-derived plasmids for expression in prokaryotic cells, such as E. coli.

A number of vectors exist for the expression of recombinant proteins in yeast. For instance, YEP24, YIP5, YEP51, YEP52, pYES2, and YRP17 are cloning and expression vehicles useful in the introduction of genetic constructs into S. cerevisiae. These vectors can replicate in E. coli due to the presence of the pBR322 ori, and in S. cerevisiae due to the replication determinant of the yeast 2 micron plasmid. In addition, drug resistance markers such as ampicillin can be used.

Certain mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. In some instances, it may be desirable to express the recombinant rictor or GβL polypeptide by the use of a baculovirus expression system. Examples of such baculovirus expression systems include pVL-derived vectors (such as pVL1392, pVL1393 and pVL941), pAcUW-derived vectors (such as pAcUWI), and pBlueBac-derived vectors (such as the β-gal containing pBlueBac III).

Alternatively, the coding sequences for the polypeptide can be incorporated as a part of a fusion gene including a nucleotide sequence encoding a different polypeptide. This type of expression system can be useful under conditions where it is desirable, e.g., to produce an immunogenic fragment of a rictor or GβL polypeptide. For example, the VP6 capsid protein of rotavirus can be used as an immunologic carrier protein for portions of polypeptide, either in the monomeric form or in the form of a viral particle. The nucleic acid sequences corresponding to the portion of the rictor or GβL polypeptide to which antibodies are to be raised can be incorporated into a fusion gene construct which includes coding sequences for a late vaccinia virus structural protein to produce a set of recombinant viruses expressing fusion proteins comprising a portion of the protein as part of the virion. The Hepatitis B surface antigen can also be utilized in this role as well. Similarly, chimeric constructs coding for fusion proteins containing a portion of a rictor or GβL polypeptide and the poliovirus capsid protein can be created to enhance immunogenicity.

In yet another embodiment, the invention provides a substantially pure nucleic acid which hybridizes under high stringency conditions to a nucleic acid probe that comprises at least about 12, at least about 15, at least about 25, or at least about 40 consecutive nucleotides up to the full length of SEQ ID NO: 2 or 4, or a sequence complementary thereto or up to the full length of the gene of which said sequence is a fragment. The invention also provides an antisense oligonucleotide analog which hybridizes under stringent conditions to at least 12, at least 25, or at least 50 consecutive nucleotides up to the full length of SEQ ID NO: 2 or 4, or a sequence complementary thereto.

One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature. In another embodiment, the invention provides nucleic acids which hybridize under high stringency conditions of 0.5×SSC at 60° C. followed by 2 washes at 0.5×SSC at 60° C.

In a further embodiment, the invention provides a nucleic acid comprising a nucleic acid encoding the amino acid sequence of SEQ ID NO: 3 or 6, or a nucleic acid complementary thereto. In a further embodiment, the encoded amino acid sequence is at least about 70%, 80%, 90%, 95%, or 97-98%, or greater than 99% identical to a sequence corresponding to at least about 12, at least about 15, at least about 25, or at least about 40, at least about 100, at least about 200, at least about 300, at least about 400 or at least about 500 consecutive amino acid residues up to the full length of SEQ ID NO: 3 or 6.

Nucleic acids of the invention further include nucleic acids that comprise variants of SEQ ID NO: 2 or 4. Variant nucleotide sequences include sequences that differ by one or more nucleotide substitutions, additions or deletions, such as allelic variants; and will, therefore, include coding sequences that differ from the nucleotide sequence of the coding sequence designated in SEQ ID NO: 2 or 4, e.g., due to the degeneracy of the genetic code. In other embodiments, variants will also include sequences that will hybridize under highly stringent conditions to a nucleotide sequence of a coding sequence designated in SEQ ID NO: 2 or 4.

Isolated nucleic acids which differ from SEQ ID NO: 2 or 4 due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. All such nucleotide variations and resulting amino acid polymorphisms are within the scope of this invention.

In another embodiment, the invention provides a probe or primer (e.g., DNA, RNA) which hybridizes under stringent conditions to at least about 12, at least about 15, at least about 25, or at least about 40 consecutive nucleotides of sense or antisense sequence selected from SEQ ID NO: 2 or 4, or a sequence complementary thereto. In certain embodiments, a probe of the present invention hybridizes to a characteristic region of SEQ ID NO: 2 or 4 and is useful to identify additional toll-like receptors. The probe may include a detachable label, such as a radioisotope, a fluorescent compound, an enzyme, or an enzyme co-factor. The invention further provides arrays of at least about 10, at least about 25, at least about 50, or at least about 100 different probes as described above attached to a solid support. Such arrays are useful to assess samples (e.g., tissues, blood, cells) for the presence of rictor or GβL nucleic acids (e.g., rictor mRNA or GβL mRNA).

Optionally, a rictor or GβL nucleic acid of the invention will genetically complement a partial or complete rictor or GβL loss of function phenotype in a cell. For example, a rictor or GβL nucleic acid of the invention may be expressed in a cell in which endogenous rictor or GβL gene expression has been reduced by RNAi, and the introduced rictor or GβL nucleic acid will mitigate a phenotype resulting from the RNAi. The term "RNA interference" or "RNAi" refers to any method by which expression of a gene or gene product is decreased by introducing into a target cell one or more double-stranded RNAs which are homologous to the gene of interest (particularly to the messenger RNA of the gene of interest).

Another aspect of the invention relates to rictor or GβL nucleic acids that are used for antisense, RNAi or ribozymes. As used herein, nucleic acid therapy refers to administration or in situ generation of a nucleic acid or a derivative thereof which specifically hybridizes (e.g., binds) under cellular conditions with the cellular mRNA and/or genomic DNA encoding one of the subject rictor or GβL polypeptides so as to inhibit production of that protein, e.g., by inhibiting transcription and/or translation. The binding may be by conventional base pair complementarity, or, for example, in the case of binding to DNA duplexes, through specific interactions in the major groove of the double helix.

A nucleic acid therapy construct of the present invention can be delivered, for example, as an expression plasmid which, when transcribed in the cell, produces RNA which is complementary to at least a unique portion of the cellular mRNA which encodes a rictor or GβL polypeptide. Alternatively, the construct is an oligonucleotide which is generated ex vivo and which, when introduced into the cell causes inhibition of expression by hybridizing with the mRNA and/or genomic sequences encoding a rictor or GβL polypeptide. Such oligonucleotide probes are optionally modified oligonucleotides which are resistant to endogenous nucleases, e.g., exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in nucleic acid therapy have been reviewed, for example, by van der Krol et al., (1988) Biotechniques 6:958-976; and Stein et al., (1988) Cancer Res 48:2659-2668. Nucleic acid constructs of the invention are useful in therapeutic, diagnostic, and research contexts.

In addition to their use in therapy, the oligomers of the invention may be used as diagnostic reagents to detect the presence or absence of the rictor or GβL DNA or RNA sequences to which they specifically bind, such as for determining the level of expression of a gene of the invention or for determining whether a gene of the invention contains a genetic lesion.

In another aspect, the invention provides polypeptides. In one embodiment, the invention pertains to a polypeptide encoded by a nucleic acid which hybridizes under stringent conditions to a nucleic acid of SEQ ID NO: 2 or 4, a sequence complementary thereto, or a fragment encoding an amino acid sequence comprising at least about 25, or at least about 40 amino acid residues thereof.

In another embodiment, the rictor or GβL polypeptide comprises a sequence that is identical with or homologous to SEQ ID NO: 3 or 6. For instance, a rictor or GβL polypeptide preferably has an amino acid sequence at least 70% identical to a polypeptide represented by SEQ ID NO: 3 or 6 or an amino acid sequence that is 80%, 90% or 95% identical thereto. The rictor or GβL polypeptide can be full-length, such as the polypeptide represented by the amino acid sequence in SEQ ID NO: 3 or 6, or it can comprise a fragment of, for instance, at least 5, 10, 20, 50, 100, 150, 200, 250, 300, 400 or 500 or more amino acid residues in length.

In another embodiment, the invention features a purified or recombinant polypeptide fragment of a rictor or GβL polypeptide, which polypeptide has the ability to modulate (e.g., stimulate or antagonize) an activity of a wild-type rictor or GβL protein. In one embodiment, the polypeptide fragment comprises a sequence identical or homologous to the amino acid sequence designated in SEQ ID NO: 3 or 6.

Moreover, as described below, the rictor or GβL polypeptide can be either an agonist or alternatively, an antagonist of a biological activity of a naturally occurring form of the protein, e.g., the polypeptide is able to modulate the intrinsic biological activity of a rictor or GβL protein. Optionally, the subject rictor or GβL polypeptide is able to modulate signaling through a complex containing an mTOR protein and a rictor protein, or through a complex containing an mTOR protein and a GβL protein. Signaling through such complexes include, but are not limited to, activation of mTOR kinase activity, phosporylation of S6 kinase 1 (S6K1), phosphorylation of protein kinase C a (PKC α), and organization of the actin cytoskeleton.

The present invention also relates to chimeric molecules, such as fusion proteins, that comprise all or a portion of a rictor or GβL polypeptide and a second polypeptide that is heterologous (not a rictor or GβL polypeptide), such as the extracellular domain of a CD4 receptor or an epitope tag, such as a Flag or myc epitope tag.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature.

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, eds. Ausubel et al., John Wiley & Sons: 1992).

The present invention also makes available isolated and/or purified forms of the subject rictor or GβL polypeptides, which are isolated from, or otherwise substantially free of, other intracellular proteins which might normally be associated with the protein or a particular complex including the protein. Rictor or GβL polypeptides which are recombinantly produced (e.g., by recombinant DNA methods) or chemically synthesized are also the subject of this invention.

Optionally, a rictor or GβL polypeptide of the invention will function in place of an endogenous rictor or GβL polypeptide, respectively, for example by mitigating a partial or complete rictor or GβL loss of function phenotype in a cell.

Variants and fragments of a rictor or GβL polypeptide may have enhanced activity or constitutive activity, or, alternatively, act to prevent rictor or GβL polypeptides from performing one or more functions. For example, a truncated form lacking one or more domains may have a dominant negative effect.

Another aspect of the invention relates to polypeptides derived from a full-length rictor or GβL polypeptide. Isolated peptidyl portions of the subject proteins can be obtained by screening polypeptides recombinantly produced from the corresponding fragment of the nucleic acid encoding such polypeptides. In addition, fragments can be chemically synthesized using techniques known in the art such as conventional Merrifield solid phase f-Moc or t-Boc chemistry. For example, the subject protein can be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of the formation of a specific protein complex, or more generally of a rictor- or GβL-containing complex, such as by microinjection assays.

It is also possible to modify the structure of the subject rictor or GβL polypeptides for such purposes as enhancing therapeutic or prophylactic efficacy, or stability (e.g., ex vivo shelf life and resistance to proteolytic degradation in vivo). Such modified polypeptides, when designed to retain at least one activity of the naturally-occurring form of the protein, are considered functional equivalents of the rictor or GβL polypeptides described in more detail herein. Such modified polypeptides include peptide mimetics. Peptide mimetics include chemically modified peptides and peptide-like molecules containing non-naturally occurring amino acids. Modified polypeptides can also be produced, for instance, by amino acid substitution, deletion, or addition.

For instance, it is reasonable to expect, for example, that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of a polypeptide results in a functional homolog can be readily determined by assessing the ability of the variant polypeptide to produce a response in cells in a fashion similar to the wild-type protein. For instance, such variant forms of a rictor or GβL polypeptide can be assessed, e.g., for their ability to activate the mTOR kinase; e.g., to stimulate phosphorylation of S6K1; to stimulate phosphorylation of PKCα; to modulate organization of the actin cytoskeleton; or to bind to another polypeptide such as for example, an mTOR polypeptide. Polypeptides in which more than one replacement has taken place can readily be tested in the same manner.

This invention further contemplates a method of generating sets of combinatorial mutants of the subject mTOR-AP (e.g., rictor or GβL) polypeptides, as well as truncation mutants, and is especially useful for identifying potential variant sequences (e.g., homologs) that are functional in binding to a rictor or GβL polypeptide. The purpose of screening such combinatorial libraries is to generate, for example, rictor or GβL homologs which can act as either agonists or antagonists, or alternatively, which possess novel activities all together. Combinatorially-derived homologs can be generated which have a selective potency relative to a naturally occurring rictor or GβL polypeptide. Such proteins, when expressed from recombinant DNA constructs, can be used in gene therapy protocols.

Yet another aspect of the present invention concerns an immunogen which comprises an mTOR-AP (e.g., rictor or GβL) polypeptide capable of eliciting an immune response specific for the mTOR-AP polypeptide; e.g., a humoral response, an antibody response; or a cellular response. In certain embodiments, the immunogen comprises an antigenic determinant, e.g., a unique determinant, from a protein represented by SEQ ID NO: 3 or 6.

Antibodies

Another aspect of the invention pertains to an antibody specifically reactive with an mTOR-AP (e.g., rictor or GβL) polypeptide. For example, by using immunogens derived from a rictor or GβL polypeptide, e.g., based on the cDNA sequences, anti-protein/anti-peptide antisera or monoclonal antibodies can be made by standard protocols. A mammal, such as a mouse, a hamster or rabbit can be immunized with an immunogenic form of the peptide (e.g., an mTOR-AP polypeptide or an antigenic fragment which is capable of eliciting an antibody response, or a fusion protein as described above). Techniques for conferring immunogenicity on a protein or peptide include conjugation to carriers or other techniques well known in the art. An immunogenic portion of a rictor or GβL polypeptide can be administered in the presence of adjuvant. The progress of immunization can be monitored by detection of antibody titers in plasma or serum. Standard ELISA or other immunoassays can be used with the immunogen as antigen to assess the levels of antibodies. In one embodiment, the subject antibodies are immunospecific for antigenic determinants of a rictor or GβL polypeptide of a mammal, e.g., antigenic determinants of a protein set forth in SEQ ID NO: 3 or 6.

In another embodiment, the antibodies are immunoreactive with one or more proteins having an amino acid sequence that is at least 70% identical, at least 80% identical to an amino acid sequence as set forth in SEQ ID NO: 3 or 6. In other embodiments, an antibody is immunoreactive with one or more proteins having an amino acid sequence that is 75%, 80%, 85%, 90%, 95%, 98%, 99% or identical to an amino acid sequence as set forth in SEQ ID NO: 3 or 6.

Following immunization of an animal with an antigenic preparation of an mTOR-AP (e.g., rictor or GβL) polypeptide, anti-rictor or anti-GβL antisera can be obtained and, if desired, polyclonal anti-rictor or anti-GβL antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with a mammalian rictor or GβL polypeptide of the present invention and monoclonal antibodies isolated from a culture comprising such hybridoma cells. In one embodiment, anti-mouse rictor or anti-mouse GβL antibodies specifically react with the protein encoded by a nucleic acid having SEQ ID NO: 2 or 4, respectively.

The term antibody as used herein is intended to include fragments thereof which are also specifically reactive with one of the subject mTOR-AP (e.g., rictor or GβL) polypeptides. Antibodies can be fragmented using conventional techniques and the fragments screened for utility in the same manner as described above for whole antibodies. For example, $F(ab)_2$ fragments can be generated by treating antibody with pepsin. The resulting $F(ab)_2$ fragment can be treated to reduce disulfide bridges to produce Fab fragments. The antibody of the present invention is further intended to include bispecific, single-chain, and chimeric and humanized molecules having affinity for a rictor or GβL polypeptide conferred by at least one CDR region of the antibody. In certain embodiments, the antibody further comprises a label attached thereto and able to be detected, (e.g., the label can be a radioisotope, fluorescent compound, enzyme or enzyme co-factor).

An application of anti-rictor or anti-GβL antibodies of the present invention is in the immunological screening of cDNA libraries constructed in expression vectors such as gt11, gt18-23, ZAP, and ORF8. Messenger libraries of this type, having coding sequences inserted in the correct reading frame and orientation, can produce fusion proteins. For instance, gt11 will produce fusion proteins whose amino termini consist of β-galactosidase amino acid sequences and whose carboxy termini consist of a foreign polypeptide. Antigenic epitopes of a rictor or GβL polypeptide, e.g., other orthologs of a particular protein or other paralogs from the same species, can then be detected with antibodies, as, for example, reacting nitrocellulose filters lifted from infected plates with the appropriate anti-rictor or anti-GβL antibodies. Positive phage detected by this assay can then be isolated from the infected plate. Thus, the presence of rictor or GβL homologs can be detected and cloned from other animals, including humans.

Transgenic Animals

Another aspect of the invention features transgenic non-human animals which express a heterologous mTOR-AP (rictor or GβL) gene, e.g., having a sequence of SEQ ID NO: 2 or 5, or fragments thereof. In another aspect, the invention features transgenic non-human animals which have had one or both copies of the endogenous mTOR-AP gene disrupted in at least one of the tissue or cell-types of the animal. In one embodiment, the transgenic non-human animals is a mammal such as a mouse, rat, rabbit, goat, sheep, dog, cat, cow or non-human primate. Without being bound to theory, it is proposed that such an animal may display a phenomenon associated with reduced or increased chance of a disease or a condition, such as cancer, diabetes, or cardiovascular diseases. Accordingly, such a transgenic animal may serve as a useful animal model to study the progression of such diseases or conditions.

The term "transgene" is used herein to describe genetic material that has been or is about to be artificially inserted into the genome of a mammalian cell, particularly a mammalian cell of a living animal. The transgene is used to transform a cell, meaning that a permanent or transient genetic change, preferably a permanent genetic change, is induced in a cell following incorporation of exogenous DNA. A permanent genetic change is generally achieved by introduction of the DNA into the genome of the cell. Vectors for stable integration include plasmids, retroviruses and other animal viruses, YACs, and the like. Of interest are transgenic mammals. Preferably, the transgenic-animals are mice.

Transgenic animals comprise an exogenous nucleic acid sequence present as an extrachromosomal element or stably integrated in all or a portion of its cells, especially in germ cells. Unless otherwise indicated, it will be assumed that a transgenic animal comprises stable changes to the germline sequence. During the initial construction of the animal, "chimeras" or "chimeric animals" are generated, in which only a subset of cells have the altered genome. Chimeras are primarily used for breeding purposes in order to generate the desired transgenic animal. Animals having a heterozygous alteration are generated by breeding of chimeras. Male and female heterozygotes are typically bred to generate homozygous animals.

The exogenous gene is usually either from a different species than the animal host, or is otherwise altered in its coding or non-coding sequence. The introduced gene may be a wild-type gene, naturally occurring polymorphism, or a genetically manipulated sequence, for example having deletions, substitutions or insertions in the coding or non-coding regions. Where the introduced gene is a coding sequence, it is usually operably linked to a promoter, which may be constitutive or inducible, and other regulatory sequences required for expression in the host animal.

In one aspect of the invention, an mTOR-AP (rictor or GβL) transgene can encode the wild-type form of the protein, homologs thereof, as well as antisense constructs. An mTOR-AP transgene can also encode a soluble form of an mTOR-AP, e.g., one that has tumor suppressor activity.

It may be desirable to express the heterologous mTOR-AP transgene conditionally such that either the timing or the level of mTOR-AP gene expression can be regulated. Such conditional expression can be provided using prokaryotic promoter sequences which require prokaryotic proteins to be simultaneous expressed in order to facilitate expression of the mTOR-AP transgene. Exemplary promoters and the corresponding trans-activating prokaryotic proteins are given in U.S. Pat. No. 4,833,080.

Moreover, transgenic animals exhibiting tissue specific expression can be generated, for example, by inserting a tissue specific regulatory element, such as an enhancer, into the transgene. For example, the endogenous mTOR-AP gene promoter or a portion thereof can be replaced with another promoter and/or enhancer, e.g., a CMV or a Moloney murine leukemia virus (MLV) promoter and/or enhancer.

Transgenic animals containing an inducible mTOR-AP transgene can be generated using inducible regulatory elements (e.g., metallothionein promoter), which are well-known in the art. mTOR-AP transgene expression can then be initiated in these animals by administering to the animal a compound which induces gene expression (e.g., heavy metals). Another preferred inducible system comprises a tetracycline-inducible transcriptional activator (U.S. Pat. Nos. 5,654,168 and 5,650,298).

The present invention provides transgenic animals that carry the transgene in all their cells, as well as animals that carry the transgene in some, but not all cells, i.e., mosaic animals. The transgene can be integrated as a single transgene or in tandem, e.g., head to head tandems, or head to tail or tail to tail or as multiple copies.

The successful expression of the transgene can be detected by any of several means well known to those skilled in the art. Non-limiting examples include Northern blot, in situ hybridization of mRNA analysis, Western blot analysis, immunohistochemistry, and FACS analysis of protein expression.

In a further aspect, the invention features non-human animal cells containing an mTOR-AP transgene, preferentially a human mTOR-AP transgene. For example, the animal cell (e.g., somatic cell or germ cell) can be obtained from the transgenic animal. Transgenic somatic cells or cell lines can be used, for example, in drug screening assays. Transgenic germ cells, on the other hand, can be used in generating transgenic progeny.

Although not necessary to the operability of the invention, the transgenic animals described herein may comprise alterations to endogenous genes in addition to, or alternatively, to the genetic alterations described above. For example, the host animals may be either "knockouts" or "knockins" for the mTOR-AP gene. Knockouts have a partial or complete loss of function in one or both alleles of an endogenous gene of interest. Knockins have an introduced transgene with altered genetic sequence and/or function from the endogenous gene. The two may be combined, for example, such that the naturally occurring gene is disabled, and an altered form introduced. For example, it may be desirable to knockout the host animal's endogenous mTOR-AP gene, while introducing an exogenous mTOR-AP gene (e.g., a human mTOR-AP gene).

In a knockout, preferably the target gene expression is undetectable or insignificant. For example, a knock-out of an mTOR-AP gene means that function of the mTOR-AP has been substantially decreased so that expression is not detectable or only present at insignificant levels. This may be achieved by a variety of mechanisms, including introduction of a disruption of the coding sequence, e.g., insertion of one or more stop codons, insertion of a DNA fragment, deletion of coding sequence, substitution of stop codons for coding sequence, etc. In some cases, the exogenous transgene sequences are ultimately deleted from the genome, leaving a net change to the native sequence. Different approaches may be used to achieve the "knock-out." A chromosomal deletion of all or part of the native gene may be induced, including deletions of the non-coding regions, particularly the promoter region, 3' regulatory sequences, enhancers, or deletions of gene that activate expression of APP genes. A functional knock-out may also be achieved by the introduction of an anti-sense construct that blocks expression of the native genes (for example, see Li and Cohen (1996) Cell 85:319-329). "Knock-outs" also include conditional knock-outs, for example, where alteration of the target gene occurs upon exposure of the animal to a substance that promotes target gene alteration, introduction of an enzyme that promotes recombination at the target gene site (e.g., Cre in the Cre-lox system), or other method for directing the target gene alteration postnatally.

A "knockin" of a target gene means an alteration in a host cell genome that results in altered expression or function of a native target gene. Increased (including ectopic) or decreased expression may be achieved by introduction of an additional copy of the target gene, or by operatively inserting a regulatory sequence that provides for enhanced expression of an endogenous copy of the target gene. These changes may be constitutive or conditional, i.e., dependent on the presence of an activator or repressor. The use of knockin technology may be combined with production of exogenous sequences to produce the transgenic animals of the invention.

Drug Screening Assays

In certain embodiments, the present invention provides assays for identifying therapeutic agents which either interfere with or promote function of the mTOR-AP protein (e.g., rictor or GβL). In certain embodiments, agents of the invention specifically modulate rictor activity. In another embodiment, agents of the invention specifically modulate GβL activity. In certain embodiments, agents of the invention modulate the activity of rictor and/or GβL and may be used to treat certain diseases such as cancer or diabetes, or a disease or condition that is responsive to modulation of the mTOR or mTOR-AP (e.g., rictor or GβL). In certain embodiments, the invention provides assays to identify, optimize or otherwise assess agents that increase or decrease the activity of a rictor polypeptide, a GβL polypeptide, or both a rictor and a GβL polypeptide.

In certain embodiments, an assay of the invention comprises screening for activation of mTOR kinase. For example, mammalian cells such as HeLa cells are contacted with a compound, and then lysed. mTOR kinases are then immunoprecipitated and assayed for its activation. See for example, Example 6 as described below.

In certain embodiments, an assay as described above may be used to identify agents that modulate the anti-tumor activity of an mTOR-AP (e.g., rictor or GβL). Alternative, the present invention contemplates a screening assay that generally involves adding a test agent to an assay designed to assess the anti-tumor activity of a rictor or GβL polypeptide. The parameters detected in a screening assay may be compared to a suitable reference. A suitable reference may be an assay run previously, in parallel or later that omits the test agent. A suitable reference may also be an average of previous measurements in the absence of the test agent. In general, the components of a screening assay mixture may be added in any order consistent with the overall activity to be assessed, but certain variations may be preferred.

In a screening assay, the effect of a test agent may be assessed by, for example, assessing the effect of the test agent on kinetics, steady-state and/or endpoint of the reaction.

Certain embodiments of the invention relate to assays for identifying agents that bind to an mTOR-AP polypeptide (e.g., rictor or GβL), optionally a particular domain of rictor or GβL, such as a domain that binds to an mTOR protein. In certain embodiments, the invention relates to assays for identifying agents that bind to both a rictor and a GβL polypeptide. A wide variety of assays may be used for this purpose, including labeled in vitro protein-protein binding assays, electrophoretic mobility shift assays, and immunoassays for protein binding. The purified protein may also be used for determination of three-dimensional crystal structure, which can be used for modeling intermolecular interactions and design of test agents. In one embodiment, an assay detects agents which inhibit the activation of one or more subject rictor and/or GβL polypeptides. In another embodiment, the assay detects agents which modulate the intrinsic biological activity of a rictor and/or GβL polypeptide, such as binding to an mTOR protein, activation of the mTOR kinase, or stimulating phosphorylation of PKCα, or modulating the actin cytoskeleton.

In additional embodiments of the invention, assay formats include those which approximate such conditions as formation of protein complexes, enzymatic activity, and rictor or GβL antitumor activity, e.g., purified proteins or cell lysates, as well as cell-based assays which utilize intact cells. Simple binding assays can also be used to detect agents which bind to rictor and/or GβL. Such binding assays may also identify agents that act by disrupting the interaction of a rictor or a GβL polypeptide with an mTOR protein. Agents to be tested can be produced, for example, by bacteria, yeast or other organisms (e.g., natural products), produced chemically (e.g., small molecules, including peptidomimetics), or produced recombinantly. In one embodiment, the test agent is a small organic molecule having a molecular weight of less than about 2,000 daltons.

In a further embodiment, the invention provides an assay for identifying a test compound which inhibits or potentiates the activation of a rictor and/or GβL polypeptide, comprising: (a) forming a reaction mixture including a rictor or GβL polypeptide and a test compound; and (b) detecting activation of said rictor or GβL polypeptides; wherein a change in the activation of said rictor or GβL polypeptide in the presence of the test compound, relative to activation in the absence of the test compound, indicates that said test compound potentiates or inhibits activation of said rictor or GβL polypeptide.

Assaying rictor-containing or GβL-containing complexes (e.g., a complex comprising an mTOR protein and a rictor protein, or a complex comprising an mTOR protein and a GβL protein) in the presence and absence of a candidate inhibitor, can be accomplished in any vessel suitable for containing the reactants. Examples include microtitre plates, test tubes, and micro-centrifuge tubes.

In one embodiment of the present invention, drug screening assays can be generated which detect inhibitory agents on the basis of their ability to interfere with assembly or stability of a rictor-containing or GβL-containing complex. In an exemplary binding assay, the compound of interest is contacted with a mixture comprising a rictor or GβL polypeptide and at least one interacting polypeptide such as an mTOR protein. Detection and quantification of rictor-containing or GβL-containing complexes provides a means for determining the compound's efficacy at inhibiting (or potentiating) interaction between the two polypeptides. The efficacy of the compound can be assessed by generating dose response curves from data obtained using various concentrations of the test compound. Moreover, a control assay can also be performed to provide a baseline for comparison. In the control assay, the formation of complexes is quantitated in the absence of the test compound.

In many drug screening programs which test libraries of compounds and natural extracts, high throughput assays are desirable in order to maximize the number of compounds surveyed in a given period of time. Assays of the present invention which are performed in cell-free systems, such as may be developed with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or changes in enzymatic properties of the molecular target.

Administrations and Pharmaceutical Formulations

In certain embodiments, the present invention provides a method of treatment for a disease (disorder or condition) affected by aberrant activity of an mTOR-AP (e.g., GβL or rictor). Any disease that is responsive to mTOR-AP modulation can be treated by the method of the invention. Examples of such diseases include, but are not limited to, cancer, diabetes, and cardiovascular diseases (e.g., restenosis).

In an additional embodiment of the invention, an mTOR-AP polypeptide of the invention or fragment thereof is administered to an individual. For example, a rictor or a GβL polypeptide of the invention or fragment thereof is administered to an individual. In certain embodiments, both a rictor polypeptide or fragment thereof and a GβL polypeptide or fragment thereof are administered together to an individual. The individual can be a mammal such as a human.

When administered to an individual, the mTOR-AP polypeptide (e.g., rictor and/or GβL) can be administered as a pharmaceutical composition containing, for example, the mTOR-AP polypeptide and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil or injectable organic esters.

A pharmaceutically acceptable carrier can contain physiologically acceptable compounds that act, for example, to stabilize or to increase the absorption of the mTOR-AP polypeptide (e.g., rictor and/or GβL). Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the composition.

One skilled in the art would know that a pharmaceutical composition containing an mTOR-AP polypeptide (e.g., rictor and/or GβL) can be administered to a subject by various routes including, for example, oral administration; intramuscular administration; intravenous administration; anal administration; vaginal administration; parenteral administration; nasal administration; intraperitoneal administration; subcutaneous administration and topical administration. The composition can be administered by injection or by incubation. The pharmaceutical composition also can be an mTOR-AP polypeptide (e.g., rictor and/or GβL) linked to a liposome or other polymer matrix. Liposomes, for example, which consist of phospholipids or other lipids, are nontoxic, physiologically acceptable and metabolizable carriers that are relatively simple to make and administer.

EXEMPLIFICATION

Example 1

Identification of GβL as a Subunit of the mTOR-Signaling Complex

Using cell lysis conditions that preserve the raptor-mTOR complex, Applicants isolated, from HEK-293T cells growing in nutrient-rich media, a 36-kDa protein that specifically interacts with mTOR. Coomasie-blue staining of SDS-PAGE analyses of mTOR immunoprecipitates revealed that the 36-kDa protein and mTOR are present in near stoichiometric ratios (FIG. 1A). Raptor was found in substoichiometric amounts with mTOR (FIG. 1A). Mass spectrometric analysis identified the 36-kDa protein as GβL (G protein β subunit Like protein, pronounced 'Gable'), a widely expressed protein of unknown function (Rodgers, B. D., et al. (2001), J. Endocrinol 168, 325-32). The structure of GβL consists almost entirely of seven WD40 repeats with high sequence similarity to those in the β subunits of heterotrimeric G-proteins (Rodgers, B. D., et al. (2001), J. Endocrinol 168, 325-32) (FIGS. 17 and 18). Like mTOR and raptor, GβL is conserved among all eukaryotes, including *D. melanogaster, S. pombe, S. cerevisiae, C. elegans*, and *A. thaliana* (Ochotorena, I. L., et al. (2001), J. Cell Sci. 114, 2911-20; Roberg, K. J., et al. (1997), Genetics 147, 1569-84). Interestingly, genetic analyses show that Lst8p, the budding yeast homologue of GβL, regulates cell growth, the localization of amino-acid transporters and the expression of RTG genes, processes in which the TOR pathway plays a role (Roberg, K. J., et al. (1997), Genetics 147, 1569-84; Liu, Z., et al. (2001), Embo. J. 20, 7209-19). The fission yeast homologue of GβL, Wat1p, has functions in maintaining the stability of the genome and the integrity of microtubules (Ochotorena, I. L., et al. (2001), J. Cell Sci. 114, 2911-20).

Example 2

GβL Binds to the mTOR Kinase Domain Specifically and Independently or Raptor An anti-GβL antibody generated against residues 298-312 detected GβL in immunoprecipitates prepared from HEK-293T cells using an mTOR, but not control antibodies (FIG. 1B). Unlike raptor, GβL remained bound to mTOR in buffers containing the detergent Triton X-100, suggesting that the GβL-mTOR interaction does not require raptor. In addition to HEK-293T cells, Applicants also detected the mTOR-GβL complex in mouse NIH-3T3 and C2C12 cell lines. Furthermore, when over-expressed in HEK-293T cells, recombinant myc-tagged GβL interacted with endogenous (FIG. 1C) and co-expressed HA-mTOR (FIG. 1D).

To identify the GβL binding site(s) on mTOR, Applicants tested the capacity of full-length HA-GβL to interact with myc-tagged fragments of mTOR co-expressed in HEK-293T cells (FIG. 1E). GβL interacted strongly with the C-terminal half of mTOR (amino acids 1348 to 2549), a region that binds weakly, but specifically to raptor (Kim, D. H., et al. (2002), Cell 110, 163-75), On the other hand, GβL did not interact at all with the N-terminal half of mTOR (amino acids 1-1480), the region containing the principal binding site for raptor, the mTOR HEAT repeats. Further delineation of the GβL binding site revealed that GβL interacts with the mTOR kinase domain (amino acids 2115-2431) but not with the adjacent FRB domain (amino acids 2000-2115), the known binding site for FKBP12-rapamycin (Chen, J., et al. (1995), Proc. Natl. Acad. Sci. U.S.A. 92, 4947-51). Truncation of the mTOR kinase domain destroyed its strong interaction with GβL, but revealed that two separate regions of mTOR, amino acids 2185-2254 and 2255-2431, weakly bind to GβL.

Example 3

GβL Positively Regulates the mTOR Pathway

Figure 2:
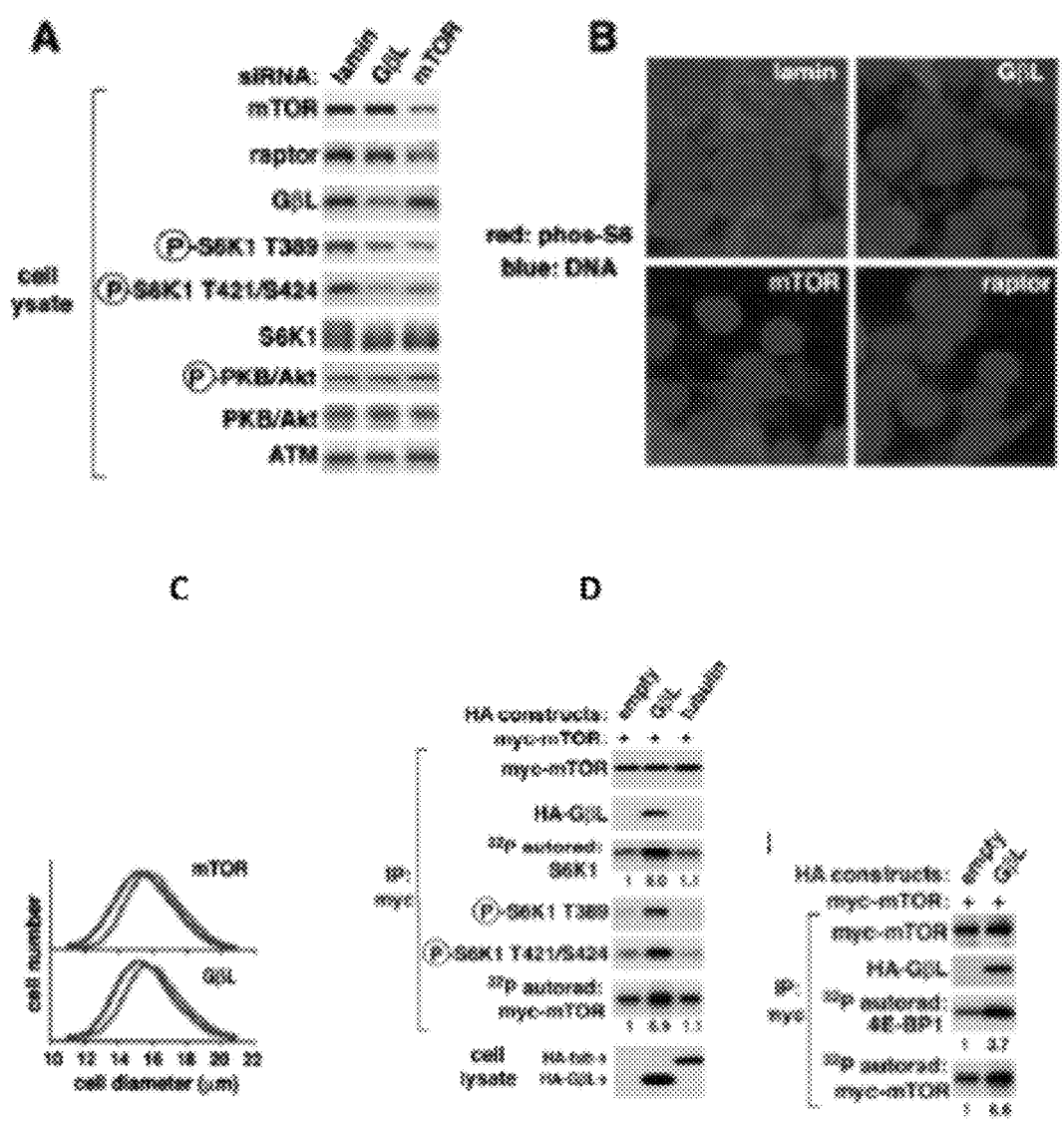
FIGS. 2A-2E show that GβL has a positive function in the mTOR pathway. (A) Inhibition of S6K1 phosphorylation in cells transfected with siRNAs targeting GβL. Cell lysates prepared from HEK-293T cells transfected with the lamin, mTOR, or GβL siRNAs were analyzed with immunoblotting for the indicated proteins. (B) Transfection of the siRNA targeting GβL eliminates S6 phosphorylation. HeLa cells transfected with the indicated siRNAs were immunostained with an antibody recognizing S6 phosphorylated at residues 235 and 236 (red channel) and stained with Hoechst to detect cell nuclei (blue channel). (C) GβL plays a role in cell size control. Shown are distributions of cell diameters of actively growing HEK-293T cells three days after transfection with siRNA targeting lamin (red line), mTOR or GβL (blue line). The mean±S.D. (μm) of the cell diameters are: lamin siRNA 16.02±0.05 (n=4); mTOR siRNA 15.47±0.05 (*) (n=4); GβL siRNA 15.45±0.06 (*) (n=4). (*) p<0.05 when compared to lamin control. (D) GβL stimulates the in vitro mTOR kinase activity. mTOR kinase activities towards GST-S6K1, 4E-BP1 and itself were determined using anti-myc immunoprecipitates prepared from cells transfected with the indicated plasmids. (E) GβL-mediated stimulation of the mTOR kinase activity correlates with the amount of GβL bound to mTOR and is independent of raptor. Myc-immonoprecipitates were prepared from HEK-293T cells expressing myc-mTOR and increasing amounts of HA-GβL and lysed in the Triton X-100-containing Buffer A (Kim et al., 2002). mTOR autophosphorylation and activity towards GST-S6K1 were determined as in (D). In (D) and (E), the numbers below the autoradiographs indicate the fold changes in $^{32}P$ incorporation as determined with a phospho-imager.
Figure 2:
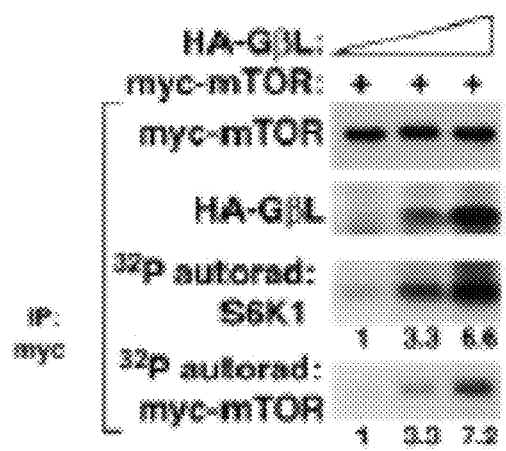

To determine the role of GβL in the mTOR pathway, Applicants investigated the effects on mTOR signaling of decreasing the expression level of GβL using siRNAs. Consistent with a critical role for GβL in mTOR function, a decrease in the expression of GβL reduced the in vivo phosphorylation state of S6K1 to a similar extent as a decrease in the expression of mTOR (FIG. 2A). The siRNA targeting GβL did not significantly affect the expression of S6K1 or ATM, or the phosphorylation state or amount of PKB1/Akt1, a downstream effector of PI 3-Kinase. Unlike raptor-targeting siRNAs (Kim, D. H., et al. (2002), Cell 110, 163-75), siRNA targeting GβL did not reduce mTOR expression levels. The partial effects of the siRNAs targeting GβL and mTOR on S6K1 phosphorylation probably reflect a low transfection efficiency of the siRNAs. This was proven to be the case when Applicants monitored the activity of the mTOR pathway in individual cells using an immunofluorescence assay that detects phosphorylated S6 protein, a major S6K1 substrate. In HeLa cell monolayers transfected with siRNAs targeting mTOR, raptor, or GβL, but not lamin, many cells had no phospho-S6 staining, a result suggesting that these pathway components have necessary roles in mediating S6 phosphorylation (FIG. 2B). The mTOR pathway and S6K1 in particular, play a critical role in regulating cell growth and determining mammalian cell size (Fingar, D. C., et al. (2002), Genes Dev. 16, 1472-87; Kim, D. H., et al. (2002), Cell 110, 163-75). Consistent with a positive role for GβL in cell size control, actively growing HEK-293T cells transfected with siRNAs targeting GβL or mTOR underwent comparable reductions in size compared to cells transfected with a control siRNA (FIG. 2C). Thus, these loss of function studies indicate that GβL has a positive, likely essential role in the mTOR pathway.

In testing potential mechanisms by which GβL exerts its positive function, Applicants found that co-expressing HA-GβL with myc-mTOR strongly increased the kinase activity of mTOR towards S6K1 and 4E-BP1 and its capacity for autophosphorylation (FIG. 2D). There was a dose-response relationship between the amount of co-expressed GβL and the level of mTOR activation. GβL-mediated stimulation of the mTOR kinase did not require raptor; as it occurred even when myc-mTOR was washed with buffers containing Triton X-100, conditions that removed endogenous raptor (FIG. 2E). These results suggest that stimulation of the mTOR kinase activity is an important mechanism by which GβL positively regulates the mTOR pathway.

Example 4

GβL Mediates the Interaction Between Raptor and mTOR

Figure 3:
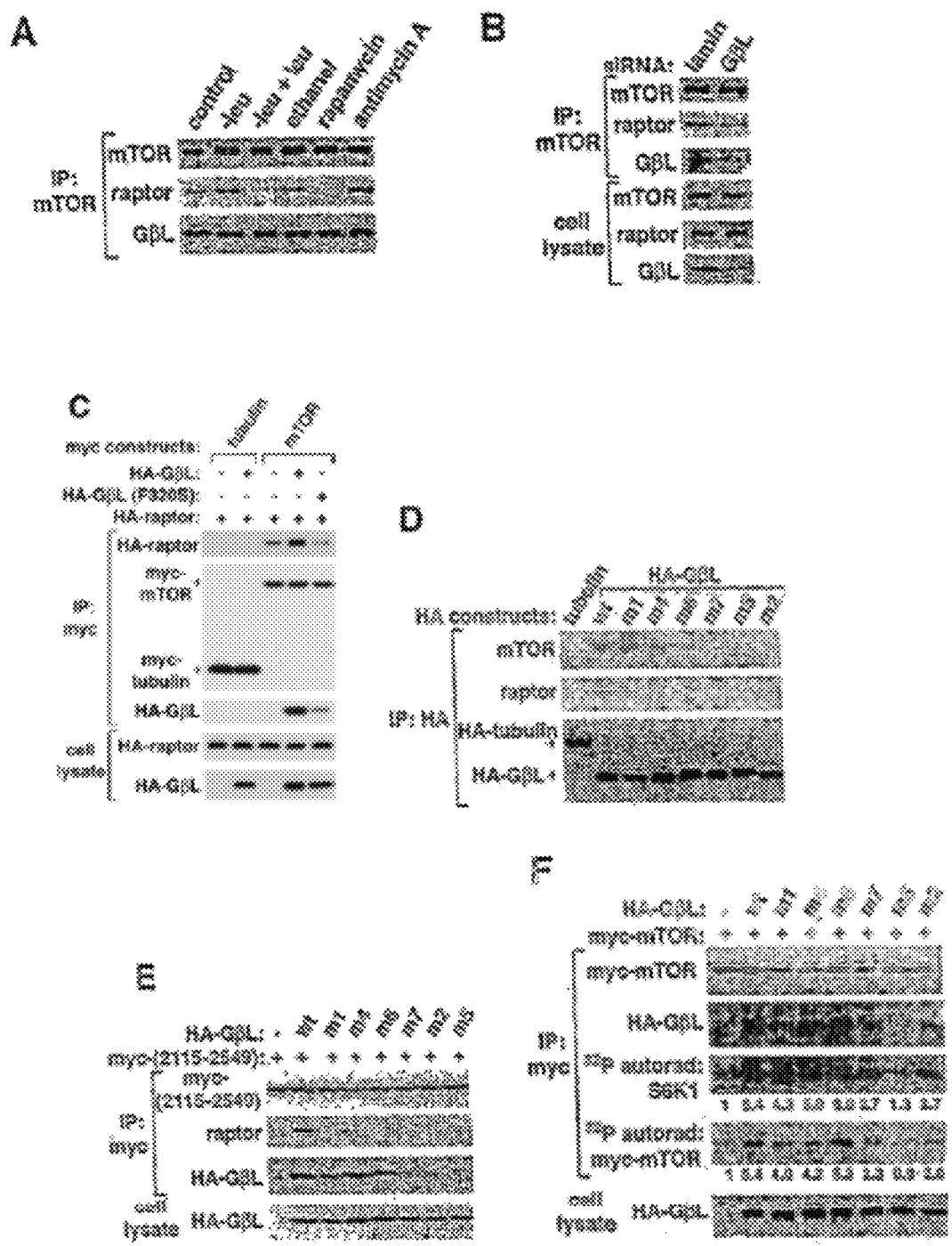
FIGS. 3A-3F show that GβL forms a heterotrimeric complex with raptor and the mTOR kinase domain. (A) The GβL-mTOR interaction is unaffected by nutrient conditions, rapamycin, and mitochondrial function. HEK-293T cells were not treated (control), deprived of leucine for 50 min (−leu), or deprived of leucine for 50 min and restimulated for 10 min with 52 μg/ml leucine (−leu+leu), or treated for 10 min with 0.001% ethanol, 20 nM rapamycin or 5 μM antimycin A. mTOR immunoprecipitates were prepared and analyzed by immunoblotting for mTOR, raptor, and GβL. (B) Destabilization of the raptor-mTOR interaction by a reduction in GβL expression. mTOR immunoprecipitates and cell lysates prepared from cells transfected with siRNA targeting lamin or GβL were analyzed by immunoblotting for mTOR, raptor, and GβL. (C) GβL stabilizes the mTOR-raptor association.

The stability of the GβL-mTOR association, unlike that of raptor-mTOR, was unaffected by nutrient conditions, such as leucine stimulation or deprivation, or by treatment with rapamycin or the mitochondrial inhibitor, antimycin A (FIG. 3A). In addition, the GβL-mTOR association was resistant to detergents like Triton X-100 (FIG. 1B) and Nonidet P-40 and high salt concentrations, suggesting that the interaction is not only constitutive, but also more stable than that of mTOR with raptor. An siRNA-mediated decrease in the expression level of GβL reduced the amount of both GβL and raptor bound to mTOR, implying that GβL has a role in stabilizing the raptor-mTOR interaction (FIG. 3B). Consistent with this, co-expression of HA-GβL with myc-mTOR significantly increased the amount of endogenous raptor that coimmunoprecipitates with myc-mTOR compared to when the latter was expressed alone (FIG. 3C).

To further explore how GβL stabilizes the association of raptor with mTOR, Applicants tested the possibility that GβL has independent binding sites for raptor and mTOR. They reasoned that if this were the case, they should be able to generate GβL mutants in which either the raptor or mTOR binding site is perturbed while the other is intact. Supporting this prediction, GβL point mutants m1, m4, and m6, when expressed in HEK-293T cells, associated with endogenous mTOR as well as wild-type GβL, but interacted very weakly with endogenous raptor (FIG. 3D). On the other hand, Applicants could not generate GβL mutants that interact only with raptor and not mTOR, although mutants m2, m5, and m7 failed to interact with either protein. This result implies that for GβL to form a stable association with raptor it must also contact mTOR. Thus, in addition to the previously discovered association between raptor and the mTOR HEAT repeats (Kim, D. H., et al. (2002), Cell 110, 163-75), raptor may also form an interaction with a structure consisting of GβL docked to the mTOR kinase domain. Supporting this possibility, an mTOR fragment consisting of mostly the kinase domain (amino acids 2115-2549) interacted with endogenous raptor only when it was co-expressed with wild-type GβL, but not the m1, m4, and m6 mutants (FIG. 3E). These results indicate that mTOR, raptor, and GβL form a heterotrimeric complex in which raptor interacts with both the mTOR HEAT repeats and a structure consisting of the GβL docked to the mTOR kinase domain. Because all the GβL mutants that bind mTOR also stimulated its in vitro kinase activity (FIG. 3F), the activating capacity of GβL is likely independent of its capacity to mediate the association of raptor with the mTOR.

Example 5

Figure 4:
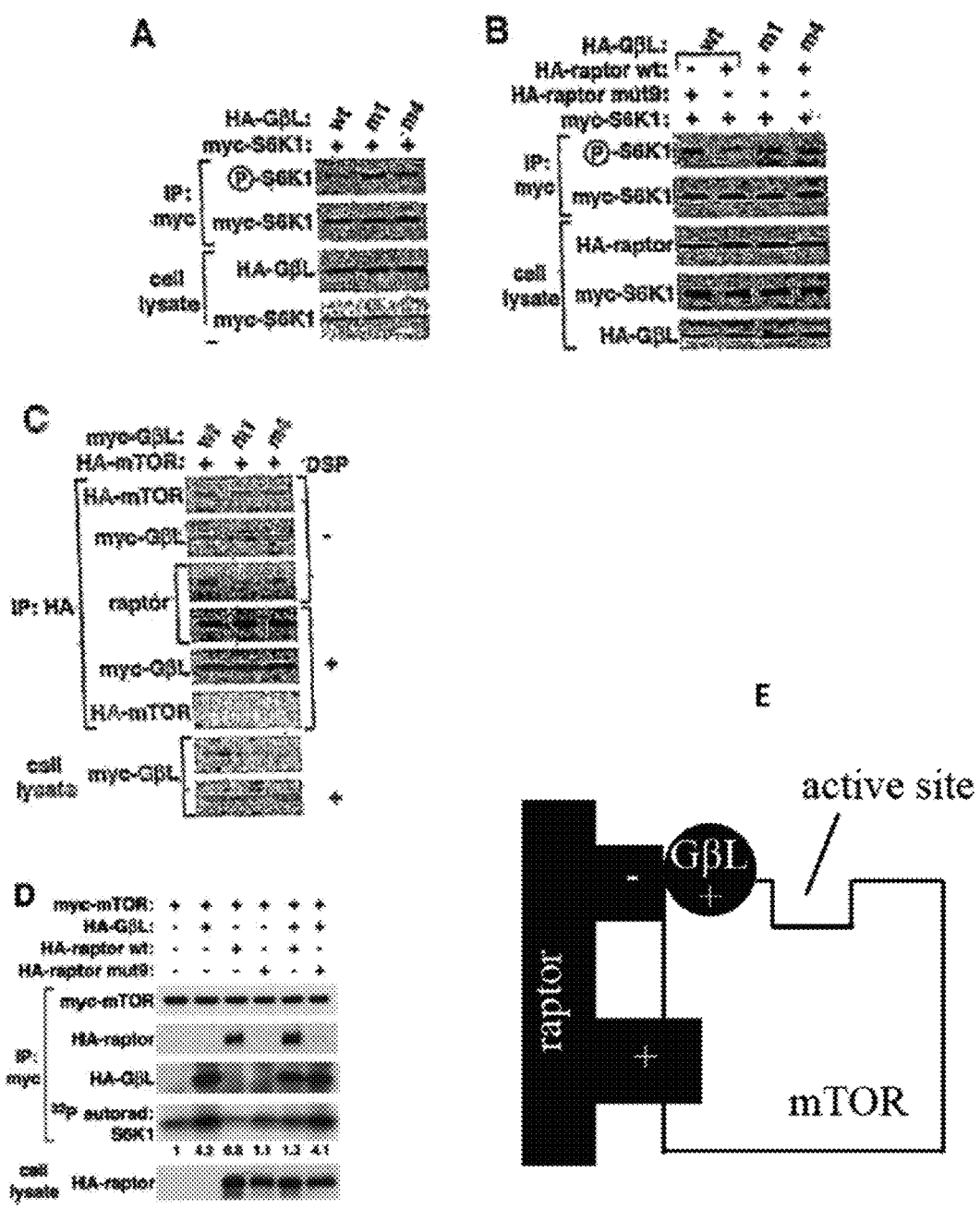

GβL Forms Part of the Nutrient-Sensitive Interaction Site for Raptor on mTOR-GβL Before the discovery of GβL, Applicants hypothesized that both a constitutive and a nutrient-sensitive interaction site mediates the association between raptor and mTOR (Kim, D. H., et al. (2002), Cell 110, 163-75). They proposed that the nutrient-sensitive interaction strengthens under nutrient-poor conditions, stabilizes the mTOR-raptor complex so that it survives in vitro isolation, and leads to an inhibition of the mTOR kinase activity. Because GβL mediates the interaction between raptor and the mTOR kinase domain and stabilizes the raptor-mTOR interaction, Applicants considered the possibility that GβL is part of the nutrient-sensitive interaction site and that the GβL-raptor interaction is needed for raptor to inhibit the mTOR kinase activity. If this model is correct, GβL mutants that cannot target raptor to the mTOR kinase domain should protect mTOR from the inhibitory effects of raptor. Based on this model, Applicants would expect, then, that expression of these mutants would activate the mTOR parthway in vivo. As predicted, expression of the GβL mutants (m1 or m4) with selective perturbations in the raptor-GβL (FIG. 4A) led to higher phosphorylation levels of co-expressed myc-S6K1 than did expression of wild-type GβL. Applicants next asked if the expression of these mutants could prevent the inhibitory effects of overexpressing wild-type raptor on the mTOR pathway (Kim, D. H., et al. (2002), Cell 110, 163-75). The over-expression of wild-type raptor, but not of a mutant (mutant 9) that cannot bind mTOR (Kim, D. H., et al. (2002), Cell 110, 163-75), decreased the phosphorylation state of a myc-S6K1 reporter. This effect was not blocked by the co-expression of wild-type GβL (FIG. 4B), but by the expression of the GβL mutants (m1 or m4) that cannot interact with raptor. Finally, as predicted, the m1 and m4 GβL mutants mimicked the destabilizing effects of nutrient-rich conditions on the association between raptor and the mTOR-GβL complex. Mutant-containing mTOR-GβL complexes bound less endogenous raptor than complexes with wild-type GβL (FIGS. 3D and 4C). However, when cells were lysed in the presence of the cross-linker DSP, similar amounts of raptor were recovered with the mTOR-GβL complexes, irrespective of whether they contained wild-type or mutant GβL (FIG. 4C). Applicants have previously shown that DSP can similarly preserve the unstable interaction between raptor and mTOR seen under nutrient-rich conditions (Kim, D. H., et al. (2002), Cell 110, 163-75). These observations indicate that, like nutrient-rich conditions, the GβL m1 and m4 mutants destabilize, but do not dissociate within cells, the association between raptor and mTOR-GβL. Thus, the raptor-GβL interaction site has the characteristics of the nutrient-sensitive interaction site and GβL is likely to play a critical role in mediating raptor regulation of mTOR activity. Furthermore, these results suggest that for raptor to inhibit the mTOR pathway it must interact with mTOR bound to GβL.

Consistent with this notion, in the absence of GβL, HA-raptor had only a small inhibitory effect on the kinase activity of co-expressed myc-mTOR. On the other hand, when the three proteins were expressed together to form a heterotrimeric complex, HA-raptor almost completely inhibited the HA-GβL-stimulated increase in myc-mTOR kinase activity (FIG. 4D). The raptor mutant 9 incapable of interacting with mTOR did not affect the basal or the GβL-stimulated mTOR kinase activity.

Results of work described herein indicate that inhibition of the mTOR kinase by raptor requires GβL and suggests a model in which the opposing actions of GβL and raptor regulate mTOR activity (FIG. 4E). They also support the conclusion that GβL interacts constitutively with mTOR, activates the mTOR kinase, and creates a nutrient-sensitive binding site for raptor. How GβL stimulates the mTOR kinase activity is unknown. It could contribute to the stability or folding of the mTOR kinase domain, a possibility supported by the finding that several heat shock protein bind the GβL-binding fragment of mTOR when it is expressed in the absence of GβL. GβL may also play a role in the recognition of mTOR substrates, although Applicants did not detect an interaction between GβL and S6K1 or 4E-BP1. Alternatively, GβL might recruit another, currently unidentified, protein that positively regulates mTOR function. Irrespective of the mechanism by which GβL activates mTOR, in Applicants' model the binding of raptor to the complex of GβL and the mTOR kinase domain inhibits this activation (FIG. 4E). Although the docking site for FKBP12-rapamycin, the FRB domain (Chen, J., et al. (1995), Proc. Natl. Acad. Sci. U.S.A. 92, 4947-51), is directly N-terminal on mTOR to the GβL binding site, rapamycin does not significantly affect the amount of GβL bound to mTOR (FIG. 3A). Instead, rapamycin destabilizes the GβL-dependent interaction between mTOR and raptor (Kim, D. H., et al. (2002), Cell 110, 163-75), and may inhibit mTOR activity by affecting the positive function of GβL.

Between GβL and raptor, the mTOR signaling complex contains 14 WD-40 repeats, which are found in numerous proteins involved in diverse cellular processes, including signal transduction, cell cycle progression, vesicular trafficking, and RNA processing (Neer, E. J., et al. (1994), Nature 371, 297-300; Smith, T. F., et al. (1999), Trends Biochem. Sci. 24, 181-5). In many cases, proteins containing WD-40 repeats form multimeric complexes with other proteins, in which the repeats serve as scaffolds for building the complexes (Smith, T. F., et al. (1999), Trends Biochem. Sci. 24, 181-5). In a few cases, domains containing WD-40 repeats play a role in recruiting phosphorylated proteins to the catalytic sites of enzymes (Nash, P., et al. (2001), Nature 414, 514-21; Yaffe, M. B. and Elia, A. E. (2001), Curr. Opin. Cell Biol. 13, 131-8). Interestingly, WD-40 repeat domains are also found in proteins interacting with PP2A, a phosphatase for which there is substantial evidence suggesting that it has a major role in regulating downstream signaling by the mTOR pathway (Moreno, C. S., et al. (2002), J. Biol. Chem. 275, 5257-63; Peterson, R. T., et al. (1999), Proc. Natl. Acad. Sci. U.S.A. 96, 4438-42). Either as scaffolds or adaptors for recruiting substrates, the WD-40 repeat domains of GβL and raptor are likely to play important roles in regulation the mTOR pathway. Furthermore, as the kinase domain of mTOR, which is also the GβL-docking site, is fairly well-conserved amongst all the PIK-related proteins (Keith, C. T. and Schreiber, S. L. (1995), Science 270, 50-1), it will be interesting to see whether other members of this family also bind GβL or related proteins.

Studies in fission yeast already hint that GβL is likely to participate in other signaling systems besides the TOR pathway. Mutations in Wat1p, the fission yeast homologue of GβL, lead to genomic instability and cell morphological changes, phenotypes not necessarily associated with TOR pathway dysfunction (Kemp, J. T., et al. (1997), Mol. Gen. Genset 254, 127-38; Ochotorena, I. L., et al. (2001), J. Cell Sci. 114, 2911-20). Furthermore, Wat1p interacts with Prp2p, the large subunit of the essential splicing factor U2AF (Ochotorena, I. L., et al. (2001), J. Cell Sci. 114, 2911-20). Nevertheless, the function experiments described herein strongly indicate that GβL plays an essential, positive role in controlling cell growth by activating the mTOR kinase (FIG. 2A-2C).

The opposing effects on mTOR activity of the interactions mediated by GβL and raptor provide a mechanism by which cellular conditions, such as nutrient levels, can positively and negatively regulate mTOR signaling to the cell growth machinery. The balance between the actions of the two regulators may be perturbed in human diseases, such as cancer and diabetes, and could be artificially manipulated for potentially therapeutic benefits.

The following experimental procedures were followed in the work described herein.

Materials

Reagents were obtained from the following sources: DSP and Protein G-Sepharose from Pierce; ATP-$\{\gamma\text{-}^{32}P\}$ from NEN; mTOR, S6K1, lamin, and Rho antibodies as well as HRP-labeled anti-mouse, anti-goat, and anti-rabbit secondary antibodies from Santa Cruz Biotechnology; Phospho-T389 S6K1 and Phospho-S473 PKB/Akt antibodies from Cell Signaling; HA monoclonal antibody from Covance; myc monoclonal antibody from Oncogene Research Products; myc rabbit polyclonal antibody from Upstate Biotechnology; DMEM, leucine, glucose, RPMI, and RPMI without leucine from Life Technologies; and rapamycin, FK506, valinomycin, antimycin A, and 2-deoxyglucose from Calbiochem. The rabbit polyclonal anti-GβL antibody, recognizing residues 298-312 of human GβL, was produced using the custom antibody service from Covance.

Purification and Identification of GβL mTOR immunoprecipitates prepared from 200 million HEK293T cells were prepared as above, resolved by SDS-PAGE, and proteins visualized by Coomassie blue staining. The band corresponding to GβL was excised and trypsinized as described (Erdjument-Bromage et al., 1994). A hundred percent of the generated peptides were subjected to a micro-clean-up procedure using 2 μL bed-volume of Poros 50 R2 (PerSeptive) reversed-phase beads packed in an Eppendorf gel-loading tip. Mass Spectrometry (Maldi-ReTOF was then carried out on two peptide pools (16 and 30% MeCN) recovered from the RP-microtip column using a Bruker REFLEX III instrument with delayed extraction. For mass fingerprinting, top major experimental masses (m/z) combined from both MALDI-ReTOF experiments were used to search a non-redundant human protein database (NR; ~66,605 entries; NCBI; Bethesda, Md.), using the PeptideSearch (M. Mann, University of Southern Denmark) algorithm. A molecular weight range twice the predicted weight was covered with a mass accuracy restriction better than 40 ppm, and maximum one missed cleavage site was allowed per peptide. Alternatively mass spectrometric-based sequencing (ESI-MS/MS) of selected peptides from partially fractioned pools was carried out using a PE-SCIEX API300 triple Quadrupole instrument, fitted with a continuous flow nano-electrospray source (JaFIS). All peptides masses in pools were obtained by DE-MALDI-reTOF MS (BRUKER Reflex III). Peptide Sequences were obtained by nono-electrospray tandem MS (JaFIS@ source with SCIEX ApI300 triple quadrupole).

Immunoprecipitations $10 \times 10^6$ HEK-293T cells growing in 10 cm dishes were rinsed once with PBS and lysed in 1 ml of ice-cold Buffer B (40 mM Hepes pH 7.5, 120 mM NaCl, 1 mM EDTA, 10 mM glycerphosphate, 50 mM NaF, 1.5 mM $Na_3 VO_4$ 0.3% CHAPS, and one tablet EDTA-free protease inhibitors (Roche) per 10 ml). After clearing the lysates by centrifugation at 10,000×g for 10 min, 30 μl of a 50% slurry of protein G-Sepharose and 4 μg of the immunoprecipitating antibody was added to the supernatant. After a 3-hour incubation at 4° C., immunoprecipitates were washed four times with Buffer B and once with Wash Buffer 1 (50 mM Hepes pH 7.5, 40 mM NaCl, and 2 mM ETDA). Samples were resolved by SDS-PAGE, proteins transferred to PVDF and used for immunoblotting as described (Burnett, P. E., et al. (1998), PNAS 95, 1432-1437). When Triton X-100 was used to eliminate raptor binding to a mTOR, immunoprecipitates were prepared as above except that Buffer A (Buffer B with 1% Triton X-100 instead of CHAPS) was used to lyse the cells.

Cloning of the GβL cDNA, DNA Manipulations and Mutagenesis

The human GβL clone was obtained from Incyte (clone ID 3C6), subcloned into myc- and HA-prk5 vectors by PCR, and transfected into HEK-293T cells using lipofectamine 2000 as described by the manufacturer (Invitrogen). The mTOR fragments indicated in FIGS. 1 and 19 were expressed from cDNA's subcloned into the myc-prk5 vectors. The GβL open reading frame in pBluescript II SK (+) was mutagenized using the QuickChange mutagenesis kit (Stratagene) as described by the manufacturer and subcloned into the SalI and NotI sites of myc- and HA-prk5. The GβL mutants used in this study are: m1 (D42A); m2 (S72D); m4 (A182D); m6 (T208D); m7 (F320S). The mutated sites are indicated in the alignment of the WD40 repeats (FIG. 17) and the structural model of GβL (FIG. 18). All other epitope tagged constructs have been described (Burnett, P. E., et al. (1998), PNAS 95, 1432-1437; Kim, D. H., et al. (2002), Cell 110, 163-75).

Plasmid and siRNA Transfections 3 million HEK293T cells in 6-cm dishes were transfected with plasmid constructs indicated in the Figure legends using the Lipofectamine 2000 transfection reagent (Life Technology). 24 hours after DNA addition, cells were rinsed once with PBS and lysed in 300 µl of ice cold Buffer B. Immune complexes were prepared from cleared supernatants using 3 µg polyclonal anti-myc or monoclonal anti-HA antibodies and 20 µl of a 50% slurry protein G-Sepharose. After a 3-hour incubation, immuneprecipitates were washed six times with Buffer B and twice with Wash Buffer 2. Bound proteins were eluted in 1× sample buffer, and mTOR or HA- or myc-tagged proteins were detected by immunoblotting as described (Burnett, P. E., et al. (1998), PNAS 95, 1432-1437). 21-nucleotide complementary RNAs with 2-nucleotide overhangs (Elbashir, S. M., et al. (2001), Nature 411, 494-8) were designed to target bases 188-210 if the GβL open reading frame. The sequences for the siRNAs for lamin, mTOR, and raptor, the transfection conditions and the procedures for determining cell size have been described (Kim, D. H., et al. (2002), Cell 110, 163-75).

Immunofluorescence

HeLa cells transfected with siRNA targeting lamin, GβL, mTOR, or raptor were harvested one day after transfection and seeded onto 1.5-cm diameter gelatin-coated glass coverslips. 48 hrs after seeding, the were fixed in a 3.7% paraformaldehyde for 20 min at room temperature, washed twice with PBS, and permeabilized with 0.1% Triton X-100 in PBS for 10 min. After washing twice with PBS and blocking with 1% BSA for 1 hr, the cells were incubated overnight with an anti-phospho S6 antibody (Cell Signaling Tech.). The cells were then washed twice with PBS, incubated with anti-rabbit cy3 (Jackson Immunolabs) and Hoechst for 30 min, washed with PBS, mounted in glycerol containing 0.1% p-phenylenediamine and visualized with fluorescence microscopy.

Sequence Alignments and Model Building

The WD40 repeat sequences of GβL were aligned with ClustalX v1.81 (Thompson, J. D., et al. (1997), Nucleic Acids Res. 25, 4786-82) using the Gonnet series weight matrix. Pairwise gap opening and gap extension penalties were set at 10.00 and 0.10 respectively. Multiple alignment gap opening and gap extension penalties were set at 10.00 and 0.20. The GβL model was built and optimized with Modeler (Sali, A., and Blundell, T. L. (1993), J. Mol. Biol. 234, 779-815) using the coordinates of the TUP1 β chain (pdb: 1ERJ accession: 1ERJ_B) as the template.

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain, using no more than routine experimentation, many equivalents to the specific embodiments of the invention described specifically herein. Such equivalents are intended to be encompassed in the scope of the claims.

Materials

Reagents were obtained from the following sources: DSP and Protein G-Sepharose from Pierce; ATP-{γ-$^{32}$P} from NEN; mTOR, S6K1, lamin, and Rho antibodies as well as HRP-labeled anti-mouse, anti-goat, and anti-rabbit secondary antibodies from Santa Cruz Biotechnology; Phospho-T389 S6K1 and Phospho-S473 PKB/Akt antibodies from Cell Signaling; HA monoclonal antibody from Covance; myc monoclonal antibody from Oncogene Research Products; myc rabbit polyclonal antibody from Upstate Biotechnology; DMEM, leucine, glucose, RPMI, and RPMI without leucine from Life Technologies; and rapamycin, FK506, valinomycin, antimycin A, and 2-deoxyglucose from Calbiochem. The rabbit polyclonal anti-GβL antibody, recognizing residues 298-312 of human GβL, was produced using the custom antibody service from Covance.

Example 6

Another Novel Binding Partner of mTOR, Rictor, Defines a Rapamycin-Insensitive and Raptor-Independent Pathway that Regulates the Cytoskeleton Growth is an energetically costly cellular process that is exquisitely regulated by environmental and cellular conditions. Increasing evidence indicates that mTOR is the central component of a pathway that regulates growth in mammals in response to nutrients, growth factors and stress. This protein is also the target of the complex formed by the macrolide rapamycin and its receptor FKBP 12. Like a reduction in mTOR expression, rapamycin causes a decrease in cell size and inhibits all known downstream effectors of mTOR (Gingras, et al., 2001, Prog Mol Subcell Biol, 27, 143-74; Kozma & Thomas, 2002, Bioessays, 24, 65-71; Schmelzle & Hall, 2000, Cell, 103, 253-62). When given to mice in utero the drug also phenocopies an embryonic lethal allele of mTOR (Hentges, et al., 2001, Proc Natl Acad Sci USA, 98, 13796-801). Thus, rapamycin seems to cause a loss of mTOR function and is often used to determine if mTOR participates in a cellular or molecular process of interest. Rapamycin is also an important drug with several current and potential clinical uses, including immunosuppression (Saunders, et al., 2001, Kidney Int, 59, 3-16), prevention of cardiac vessel restenosis (Morice, et al., 2002, N Engl J Med, 346, 1773-80; Sousa, et al., 2001, Circulation, 103, 192-195), anti-cancer therapy (Vogt, 2001, Trends Mol Med, 7, 482-4; Podsypanina, et al., 2001, Proc Natl Acad Sci USA, 98, 10320-5; Neshat, et al., 2001, Proc Natl Acad Sci USA, 98, 10314-9) and treatment of the genetic syndrome tuberous sclerosis complex (Gao, et al., 2002, Nat Cell Biol, 4, 699-704; Inoki, et al., 2002, Nat Cell Biol, 12, 12; Jaeschke, et al., 2002, J Cell Biol, 159, 217-24; Kwiatkowski, et al., 2002, Hum Mol Genet, 11, 525-34; Tee, et al., 2002, Proc Natl Acad Sci USA, 99, 13571-6; Kenerson, et al., 2002, Cancer Res, 62, 5645-50). mTOR does not act alone as it associates with at least two other proteins, raptor and GβL (Kim, et al., 2002, Cell, 110, 163-175; Kim, et al., 2002, Molecular Cell, 11, 895-904; Hara, et al., 2002, Cell, 110, 177-89). Both of these proteins regulate cell size (Kim, et al., 2002, Cell, 110, 163-175; Kim, et al., 2002, Molecular Cell, 11, 895-904), and are conserved in all eukaryotic model organisms (Kim, et al., 2002, Cell, 110, 163-175; Kim, et al., 2002, Molecular Cell, 11, 895-904; Hara, et al., 2002, Cell, 110, 177-89; Loewith, et al., 2002, Mol Cell, 10, 457-68; Wedaman, et al., 2003, Mol Biol Cell, 14, 1204-20; Roberg, et al., 1997, Genetics, 147, 1569-84). Raptor has multiple functions in the mTOR complex, serving as an adaptor protein for mTOR substrates (Hara, et al., 2002, Cell, 110, 177-89; Nojima, H. et al., 2003, J Biol Chem, 278, 15461-4; Choi, et al., 2003, J Biol Chem, 278, 19667-73; Schalm, et al., 2003, Curr Biol, 13, 797-806) as well as regulating mTOR activity in response to nutrients (Kim, et al., 2002, Cell, 110, 163-175). Here, Applicants identified a novel mTOR-binding protein called rictor for the reasons described below. The rictor-containing mTOR complex is distinct from the one containing raptor and does not regulate cell size or known mTOR effectors and is not a target of rapamycin. Instead, Applicants found that rictor and mTOR, but not raptor, regulate a distinct pathway that modulates the phosphorylation state of Protein Kinase C alpha (PKCα) and the organization of the actin cytoskeleton.

Figure 11:
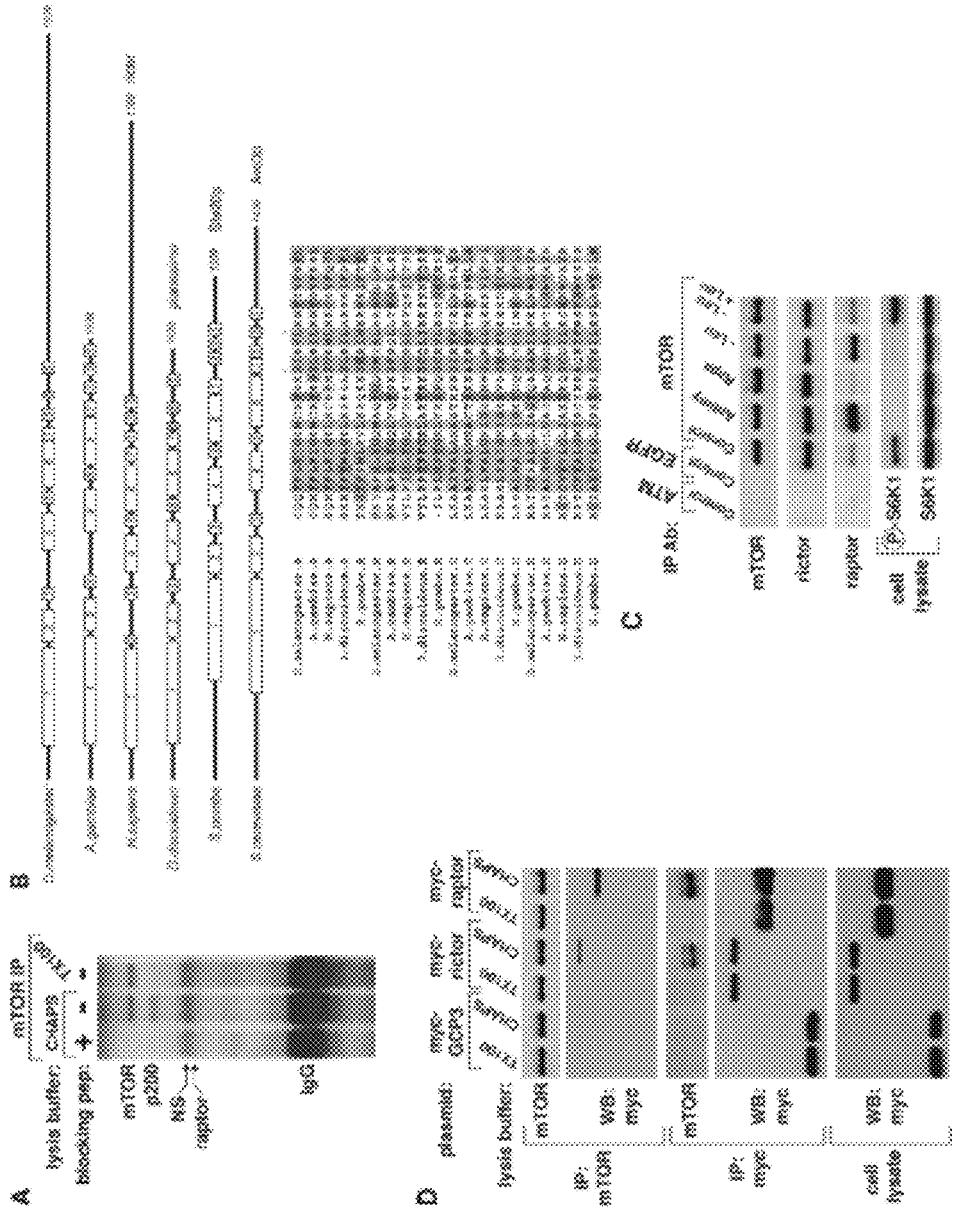

To identify novel components of the mTOR signaling complex, Applicants purified mTOR with methods that preserve the raptor-mTOR interaction (Kim, et al., 2002, Cell, 110, 163-175). In earlier work, Applicants have shown that the interaction between raptor and mTOR is unstable in buffers containing certain detergents, such as Triton X-100, but preserved in others such as CHAPS. Applicants had previously noticed that the mTOR complex immunopurified from HEK293T cells contains a low abundance 200 kDa protein, but only when purified from HeLa cells did the complex contain enough of this protein for its identification (FIG. 11A). Like the mTOR-raptor interaction, the mTOR-p200 interaction is sensitive to Triton X-100, but stable in CHAPS-containing buffers (FIG. 11A).

Peptide mass fingerprinting analysis using matrix-assisted laser desorption/ionization-time-of-flight (MALDI-TOF) mass spectrometry and mass spectrometric sequencing revealed that p200 is novel and not represented in the databases of full-length human proteins. Applicants named the 200 kDa protein rictor for rapamycin insensitive companion of mTOR. Starting from a truncated cDNA that encodes part of rictor (accession # KIAA1999), Applicants used EST mining and RT-PCR to assemble a full-length rictor open reading frame that predicts a protein of 1708 amino acids with a molecular weight of 192 kDa. Applicants could not identify any domains of known function in rictor and, compared to mTOR, raptor and GβL, the protein is not well conserved amongst eukaryotes. Rictor shares regions of homology with several poorly characterized proteins, including pianissimo from *D. discoidieum* (Chen, et al., 1997, Genes Dev, 11, 3218-31), Ste20p from *S. pombe* (Hilti, et al., 1999, Curr Genet, 35, 585-92, and Avo3p from *S. cerevisiae*). In addition, proteins of unknown function but of similar domain structure and conservation are encoded in the *A. gambiae* and *D. melanogaster* genomes, suggesting that most eukaryotes may have rictor-like proteins. These proteins share a region of about 200 amino acids in length (box 1 in FIG. 11B) of 44% similarity (8% identity) as well as several smaller conserved regions, including a repeated block of 20 amino acids (box 5 in FIG. 11B). Despite these regions of similarity both rictor and dRictor, its likely *Drosophila* homologue, have long c-terminal extensions without any apparent conservation and with no similarity to other proteins. Because of its poor conservation with pianissimo, Ste20p, and Avo3p, it is not surprising that rictor was not identified using approaches based on sequence similarity. Pianissimo is implicated in cAMP-induced cell migration (Chen, et al., 1997, Genes Dev, 11, 3218-31) and in *S. cerevisiae* Avo3p is part of a TOR2p-containing complex that regulates the actin cytoskeleton (Loewith, et al., 2002, Mol Cell, 10, 457-68). Moreover, earlier work in *S. pombe* shows that ste20p is needed for cell cycle arrest in response to nutrient deprivation (Hilti, et al., 1999, Curr Genet, 35, 585-92).

Using the antibody that recognizes human rictor, Applicants confirmed that rictor is part of the endogenous mTOR complex and does not co-immunoprecipitate with a control protein (FIG. 11C). Nutrient levels and mitochondrial function regulate the activity of S6K1 and 4E-BP1 (Kim, et al., 2002, Cell, 110, 163-175; Hara, et al., 1998, J Biol Chem, 273, 14484-94; Lynch, et al., 2000, J Cell Biochem, 77, 234-51; Dennis, et al. 2001, Science, 294, 1102-5; Xu, et al., 2001, Diabetes, 50, 353-60) as well as the stability of the raptor-mTOR interaction (Kim, et al., 2002, Cell, 110, 163-175), but these conditions do not affect the mTOR-rictor interaction. In particular, leucine levels and electron transport inhibition by antimycin A modulate the raptor- but not rictor-mTOR association (FIG. 11C). Similarly, under the appropriate cell lysis conditions, rapamycin treatment of cells eliminates the binding of mTOR to raptor (Kim, et al., 2002, Cell, 110, 163-175) without affecting the interaction of rictor with mTOR (FIG. 11C). Like raptor but not the control protein GCP3, overexpressed recombinant myc-rictor enters the endogenous mTOR complex and recombinant rictor can be used to immunoprecipitate endogenous mTOR (FIG. 11D). The interaction between recombinant rictor and mTOR, like that between the endogenous proteins, is stable in CHAPS-containing buffers but sensitive to Triton X-100 (FIG. 11D).

In mTOR complexes isolated from HEK293T cells raptor and mTOR are in a nearly stoichiometric ratio (0.8-0.9 raptor to 1.0 of mTOR) (Kim, et al., 2002, Cell, 110, 163-175). During the purification of rictor it became apparent that in HeLa cells this is not the case, and that complexes in these cells have less raptor but more rictor. When comparing mTOR complexes across mammalian cell types, Applicants always observed an inverse correlation between the amounts of raptor and rictor (FIG. 12A). For example, complexes in HeLa, HEK293T, and DU145 cells contain about the same amount of mTOR but in HeLa and DU145 cells the complexes have more rictor than raptor while the opposite is true in HEK293T cells (FIG. 12A). To determine if mTOR is in distinct complexes within cells, Applicants isolated the complex from HEK293T cells using antibodies recognizing mTOR, raptor or rictor and then determined the composition of the isolated complexes. As expected, mTOR isolated with the mTOR antibody associates with raptor, rictor and GβL in a detergent-sensitive manner (FIG. 12B). On the other hand, complexes isolated with the raptor antibody contain mTOR and GβL but not rictor while those isolated with the rictor antibody contain mTOR and GβL but not raptor (FIG. 12B). Thus, it appears that raptor and rictor independently associate with mTOR and GβL, defining two distinct mTOR complexes—one containing raptor and the other rictor. In accordance with this possibility, the expression of wild-type raptor, but not of a mutant that cannot bind mTOR (Kim, et al., 2002, Cell, 110, 163-175), strongly suppresses the interaction of co-expressed rictor with mTOR (FIG. 12C). These findings provide evidence that mammalian cells contain at least two distinct mTOR-containing complexes, reminiscent of recent work (Loewith, et al., 2002, Mol Cell, 10, 457-68; Wedaman, et al., 2003, Mol Biol Cell, 14, 1204-20), indicating that this is the case for TOR2p in budding yeast.

Figure 13:
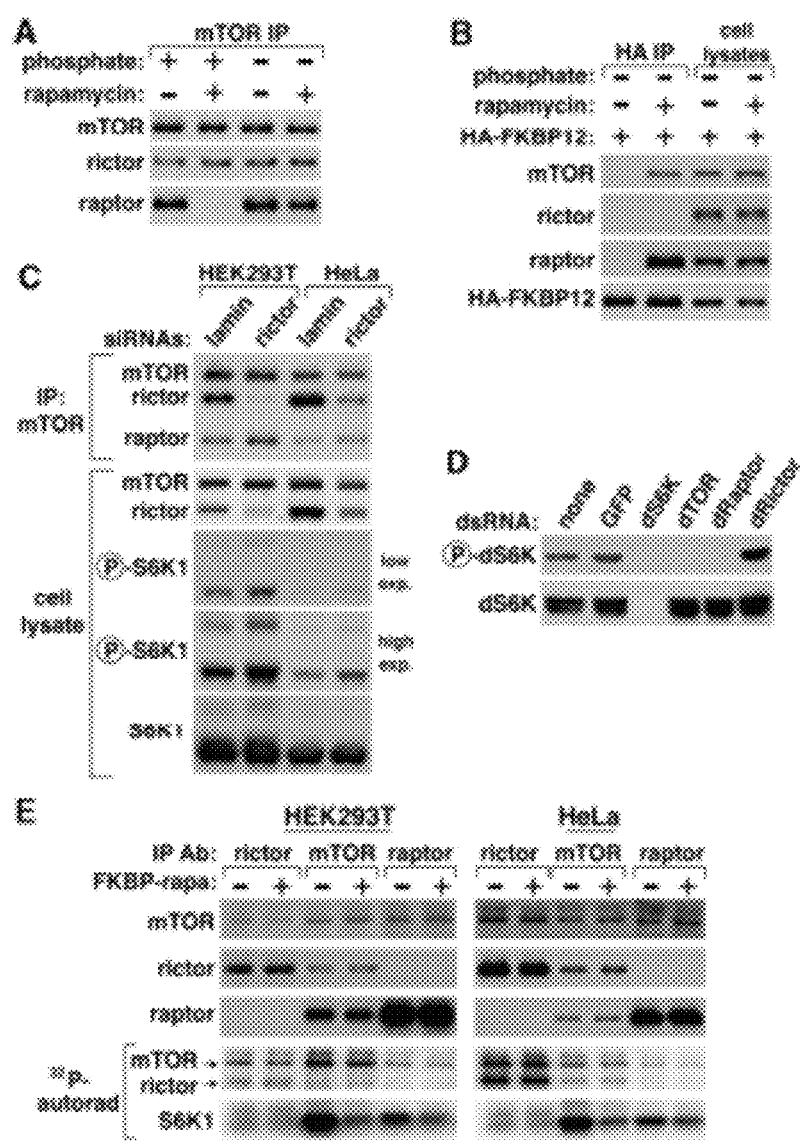

As rapamycin did not affect the interaction between rictor and mTOR (FIG. 11C), Applicants asked if the rictor-containing complex interacts with FKBP12-rapamycin and participates in rapamycin-sensitive processes. Our previous work shows that the binding of FKBP12-rapamycin to the raptor-containing complex destabilizes the raptor-mTOR interaction so that no raptor remains bound to immunopurified mTOR. As other groups have not observed this (Hara, et al., 2002, Cell, 110, 177-89; Loewith, et al., 2002, Mol Cell, 10, 457-68), Applicants suspected that a component of our buffer system might be critical for the destabilizing effect of rapamycin on the mTOR-raptor interaction. This turns out to be the case—Applicants find that for rapamycin to affect the interaction the cell lysis buffer must contain a molecule with a phosphate group (sodium pyrophosphate and beta-glycerophosphate in our buffer) (FIG. 13A). Using a phosphate-free buffer, Applicants were able to show that, in the presence of rapamycin, HA-FKBP12 expressed in HEK293T cells binds to the raptor- but not the rictor-containing mTOR complexes (FIG. 13B). This finding suggests that rictor is unlikely to participate in mTOR functions discovered through the use of rapamycin.

To confirm this notion, Applicants asked whether rictor plays a role in regulating the ribosomal S6 Kinase 1 (S6K1), a critical controller of cell size and an mTOR substrate (Burnett, et al., 1998, PNAS, 95, 1432-1437; Isotani, et al., 1999, J Biol Chem, 274, 34493-8) whose phosphorylation state is rapamycin-sensitive (Kuo, et al., 1992, Nature, 358, 70-73; Chung, et al., 1992, Cell, 69, 1227-1236; Price, et al., 1992, Science, 257, 973-7). Unlike reductions in raptor or mTOR expression (Kim, et al., 2002, Cell, 110, 163-175), siRNA-mediated knock-down of rictor levels do not decrease the phosphorylation of S6K1 in either HEK293T or HeLa cells. In contrast, Applicants reproducibly observe a slight increase in phospho-S6K1 that correlates with a small increase in the amount of raptor in the mTOR complexes isolated from cells with reduced rictor expression (FIG. 13C). Similarly, in Drosophila S2 cells dsRNA-induced RNAi against dS6K, dTOR or dRaptor eliminates the phosphorylation of dS6K while a dsRNA targeting dRictor causes an increase in dS6K phosphorylation (FIG. 13D). As might be expected, the activation of S6K caused by reductions in rictor levels leads to a small increase in mean cell size in both human and Drosophila cells (data not shown). Thus, it appears that rictor is neither a positive regulator of cell size nor of S6K phosphorylation and that intracellularly the composition of the mTOR complex is dynamic so that decreases in rictor levels lead to increases in the amount of the raptor-containing mTOR complex.

Figure 16:
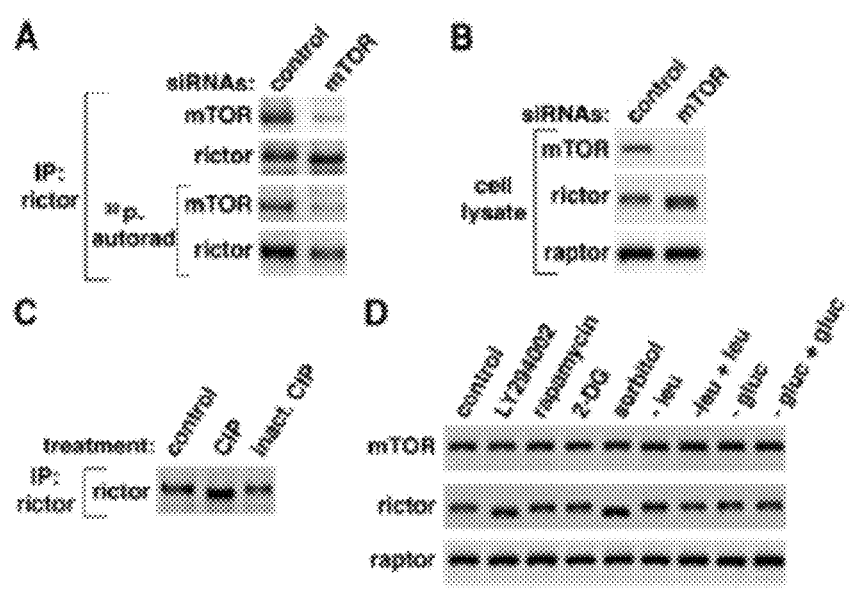

Consistent with these findings, the rictor-containing mTOR complex purified from either HEK293T or HeLa cells does not phosphorylate S6K1 in vitro (FIG. 13E). In contrast, mTOR complexes that contain raptor—isolated with antibodies recognizing either mTOR or raptor—phosphorylate S6K1 in a rapamycin sensitive fashion. A potential explanation for the inability of the rictor-containing complex to phosphorylate S6K1 might be that when bound to rictor mTOR is inactive. This is unlikely to be true because mTOR still autophosphorylates in rictor-containing complexes from HeLa or HEK293T cells (see arrows in FIG. 13E). In addition, the rictor complex phosphorylates the non-physiological substrate myelin basic protein (MBP) more effectively than the raptor complex (data not shown). Moreover, in kinase assays a protein of the same apparent molecular weight as rictor clearly becomes phosphorylated (see arrows in FIG. 13E), suggesting that rictor itself may be a substrate for the mTOR kinase activity when it is bound to mTOR. This appears to be the case because in cells metabolically labeled with radioactive phosphate a reduction in mTOR expression decreases the amount of radioactivity in rictor without affecting rictor expression (FIG. 16A). In addition, in cells with reduced mTOR expression rictor appears as a doublet in SDS-PAGE analyses, suggesting that dephosphorylated rictor migrates more quickly than the phosphorylated protein (FIG. 16B), a result Applicants confirmed using in vitro phosphatase treatment of immunoprecipitated rictor (FIG. 16C). Applicants used the phosphorylation-induced shift in rictor migration as a convenient way to search for conditions that affect rictor phosphorylation within cells. As expected for an mTOR-dependent phosphorylation, treatment of cells with LY294002, a PI 3-kinase inhibitor that also directly inhibits mTOR kinase activity (Brunn, et al., 1996, EMBO Journal, 15, 5256-5267), increased rictor mobility while rapamycin had no effect. Of the many different stress conditions, Applicants tested, only a sorbitol-induced osmotic stress also increased rictor mobility (FIG. 16D).

Only recently are Applicants beginning to understand the biochemical composition and regulation of the raptor-containing mTOR complex that is the target of rapamycin. Even before its characterization, many molecular (e.g., S6K1 phosphorylation) and cellular (e.g., cell size control) functions were ascribed to it because of their sensitivity to rapamycin. As the rictor-containing mTOR complex does not appear to participate in rapamycin-sensitive processes, there were no leads for identifying effectors downstream of rictor and insight into a function for rictor came from a fortuitous observation. In immunoblots prepared from cells with reduced rictor expression, Applicants noticed a decrease in the intensity of a faint background band recognized by the phospo-T389 S6K1 antibody. Applicants reasoned that the antibody must be cross-reacting with a protein containing a similar phosphorylation site. Through motif searching Applicants identified several candidate Protein Kinase C (PKC) isoforms with phosphorylation sites that are similar to T389 of S6K1. By testing phosphospecific antibodies that recognize these sites, Applicants discovered that a reduction in rictor expression leads to a specific decrease in the phosphorylation of S657 of PKCα. In HeLa cells the S657 phosphospecific antibody is specific for PKCα as an siRNA-mediated reduction in PKCα reduced the intensity of the band recognized by the antibody on a western blot (FIG. 14A). Using lentiviral-mediated expression of siRNAs (Stewart, et al., 2003, RNA, 9, 493-501), Applicants generated a set of HeLa cell lines with substantially reduced levels of rictor, raptor or mTOR (FIG. 14B). As expected, reductions in raptor or mTOR expression or rapamycin treatment greatly decreased the phosphorylation of S6K1 (FIG. 14B). On the other hand, a reduction in rictor expression slightly increased S6K1 phosphorylation while decreasing PKCα phosphorylation. Consistent with rictor and mTOR functioning together, a reduction in mTOR expression also decreased PKCα phosphorylation. The positive role of rictor-mTOR in mediating PKCα phosphorylation appears to be evolutionarily conserved as RNAi-mediated decreases in dRictor and dTOR, but not dRaptor, reduced, in western blots, the phosphorylation of a band with the predicted molecular weight of Drosophila PKCα (FIG. 14C). Phosphorylation of mammalian PKCα on the rictor- and mTOR-dependent site is absolutely necessary for its kinase activity (Hansra, et al., 1999, Biochem J, 342 (Pt 2), 337-44; Bornancin & Parker, 1996, Curr Biol, 6, 1114-23), suggesting that the mTOR-rictor complex has a critical role in regulating the activity of this kinase. The mTOR- and rictor-dependent phosphorylation of PKCα represents the first marker of activity for the rictor-containing mTOR complex. In this regard it is similar to the identification, more than a decade ago, of the rapamycin-sensitive phosphorylation of S6K1 (Kuo, et al., 1992, Nature, 358, 70-73; Chung, et al., 1992, Cell, 69, 1227-1236; Price, et al., 1992, Science, 257, 973-7), that Applicants now recognize as the first biochemical marker for the activity of the raptor-containing mTOR complex.

In mammalian cells, PKCα is ubiquitously expressed and has been implicated in a large number of varied cellular processes, including apoptosis, growth, cell cycle control and the regulation of cell shape and mobility (Bornancin & Parker, 1996, Curr Biol, 6, 1114-23). The HeLa cell lines with constitutively reduced levels of rictor do not have any apparent defects in cell proliferation but Applicants noticed through visual inspection that these cells were flatter and had a more square-like shape than controls. Because PKCα controls the actin cytoskeleton in some cell types (Hai, et al., 2002, Exp Cell Res, 280, 64-74) and in yeast the TOR proteins have a rapamycin-insensitive function in regulating actin organization (Loewith, et al., 2002, Mol Cell, 10, 457-68; Schmidt, et al., 1996, Proc Natl Acad Sci USA, 93, 13780-5), Applicants reasoned that an altered actin cytoskeleton might account for the perturbed morphology of the rictor knockdown cells. To examine this possibility Applicants used fluorophore-tagged phalloidin to stain for actin in cells with constitutively reduced levels of rictor, mTOR or raptor (FIG. 15A, B). In control cells, actin localizes to the cell cortex as well as diffusely and weakly throughout the cell cytoplasm (FIG. 15A). Cells with reduced raptor expression are smaller than controls but otherwise have a similar pattern of actin localization that features prominent cortical staining (FIG. 15A). In contrast, cells with reduced levels of rictor show a dramatically altered pattern of actin localization. In these cells, thick disorganized actin fibers are present throughout much of the cytoplasm and cortical actin is far less prominent. Many cells have cytoplasmic bundles of thick actin fibers without clear connections to the remainder of the actin cytoskeleton (arrow in FIG. 15A, rictor actin panel). Consistent with rictor and mTOR functioning together, in cells with reduced mTOR expression, the pattern of the actin staining is similar to that in rictor knockdown cells. Although more difficult to appreciate because of the greatly reduced size of mTOR knockdown cells, these cells also have cytoplasmic bundles of thick actin fibers (arrow in FIG. 15A, mTOR actin panel). The localization of paxillin, an adaptor protein present at the junction between the actin cytoskeleton and the plasma membrane (Turner, 2000, Nat Cell Biol, 2, E231-6), also reveals the altered organization of the actin cytoskeleton in the rictor and mTOR knockdown cells. These cells have many cytoplasmic paxillin patches that colocalize to the ends of thick actin fibers while in the control and the raptor knockdown cells the paxillin patches are present mainly at the cell periphery within cellular extensions (FIG. 15A, B). As Applicants have identified PKCα as downstream of rictor-mTOR, Applicants asked if PKCα also regulates the actin cytoskeleton in HeLa cells (FIG. 15C). The morphology of the actin cytoskeleton in cells with siRNA-mediated reductions in PKCα is reminiscent but not a complete mimic of that in the rictor knockdown cells. Both show thick cytoplasmic actin fibers and less cortical actin staining than controls, but in the PKCα knockdown cells the thick actin fibers appear more numerous, and better organized and connected to the remainder of the cytoskeleton. Thus, our findings indicate that rictor and mTOR regulate the organization of the actin cytoskeleton and suggest that PKCα is an important mediator of this function. Evidence from other species supports our finding that rictor regulates PKCα and the actin cytoskeleton. In *Dictyostelium*, pianissimo, the rictor homologue, has a positive role in mediating cAMP-induced cell aggregation (Chen, et al., 1997, Genes Dev, 11, 3218-31), a process in which PKC-like kinases are thought to be involved (Phillips, et al., 1997, Biochim Biophys Acta, 1349, 72-80). The likely rictor homologue in budding yeast, Avo3p, forms part of a complex containing TOR2p that regulates—in a rapamycin-insensitive fashion—the actin cytoskeleton. As the raptor-mTOR complex controls cell size through at least two effectors—S6K1 and 4E-BP1 (Fingar, et al., 2002, Genes Dev, 16, 1472-87)—it is probable that the rictor-mTOR complex will have more than one effector involved in controlling the organization of the cytoskeleton.

Applicants have discovered a novel complex in mammalian cells that contains mTOR but not its previously identified partner protein raptor. Instead, rictor, a new protein of unknown function, defines this complex, and the proportion of mTOR within rictor- and raptor-containing complexes varies across mammalian cell types. Currently, Applicants can only speculate as to what the rictor branch of the mTOR pathway senses as in our preliminary data Applicants find no evidence that the signals that regulate the raptor part of the mTOR pathway, such as nutrients and growth factors, regulate PKCα phosphorylation or the mTOR-rictor association. Unlike the raptor complex, the one containing rictor does not appear to be bound nor inhibited by FKBP12-rapamycin and is thus unlikely to participate in most cellular functions ascribed to mTOR based on their sensitivity to rapamycin treatment. However, small molecules that directly inhibit the kinase activities of mTOR, such as the well-known PI 3-kinase inhibitor, LY294002, appear to suppress the kinase activity of mTOR in the rictor complex. Thus, it is possible that the rictor complex mediates functions assigned to PI 3-Kinase because of their sensitivity to LY294002 and insensitivity to rapamycin. Now that two distinct mTOR complexes are known, with different downstream targets, it may be possible to isolate small molecules that selectively inhibit the rictor branch of the pathway which, in turn, are likely to have different pharmacological effects than rapamycin and direct mTOR inhibitors. Applicants have identified the phosphorylation of PKCα and the organization of the actin cytoskeleton as molecular events downstream of the rictor-mTOR complex. This finding is a critical step towards dissecting the signaling pathways controlled by the two distinct mTOR complexes and hints at the previously unrecognized complexity of the TOR network in mammalian systems.

Methods and Materials

Reagents were obtained from the following sources: protein G-sepharose from Pierce; ATP-[γ-$^{32}$P] from NEN; mTOR, S6K1, and PKCα antibodies as well as HRP-labeled anti-mouse, anti-goat, and anti-rabbit secondary antibodies from Santa Cruz Biotechnology; phospho-T389 S6K1 and phospho-PKCα/β$_2$ antibodies from Cell Signaling; HA monoclonal antibody from Covance; myc monoclonal antibody from Oncogene Research Products; *Drosophila* S6K antibody from Mary Stewart, North Dakota State University; Alexa Fluor 488-conjugated secondary anti-mouse antibody and Texas Red-X-phalloidin from Molecular Probes; paxillin monoclonal antibody from BD Transduction Laboratories; DMEM, leucine, glucose, RPMI, and RPMI without leucine from Life Technologies; rapamycin, LY294002, and antimycin A from Calbiochem. The GBL antibody was described previously (Kim et al., 2002, Cell, 110:163-175), and the rictor and raptor antibodies were developed with the antibody service from Covance using the following peptides: (rictor: RGRSLKNLRVRGRND, amino acid sequence 6-20) and (raptor: mesemlqspllglgeedead, amino acid sequence 1-20).

Purification and Identification of Rictor mTOR immunoprecipitates prepared from 60 million HeLa cells were resolved by SDS-PAGE, and proteins visualized by Coomassie blue or silver staining. The ~200 kDa band corresponding to rictor was digested with trypsin, the mixtures fractionated on a Poros 50 R2 RP micro-tip, and resulting peptide pools analyzed by matrix-assisted laser-desorption/ionization reflectron time-of-flight (MALDI-reTOF) MS using a BRUKER UltraFlex TOF/TOF instrument (Bruker Daltonics; Bremen, Germany), as described (Erdjument-Bromage, et al., 1998, J Chromatogr A, 826, 167-81; Sebastiaan Winkler, et al., 2002, Methods, 26, 260-9). Selected experimental masses (m/z) were taken to search the human segment of a non-redundant protein database ('NR'; ~108,000 entries; National Center for Biotechnology Information; Bethesda, Md.), utilizing the PeptideSearch (Matthias Mann, Southern Denmark University, Odense, Denmark) algorithm, with a mass accuracy restriction better than 40 ppm, and maximum one missed cleavage site allowed per peptide. Mass spectrometric sequencing of selected peptides was done by MALDI-TOF/TOF (MS/MS) analysis on the same prepared samples, using the UltraFlex instrument in 'LIFT' mode. Fragment ion spectra were taken to search NR using the MASCOT MS/MS Ion Search program (Matrix Science Ltd.; London, UK). Any identification thus obtained was verified by comparing the computer-generated fragment ion series of the predicted tryptic peptide with the experimental MS/MS data.

Cloning of the Full-Length Human Rictor cDNA and its Sequence Analysis

Human and mouse cDNA and EST sequences obtained from public databases were used to electronically assemble a putative full-length cDNA. The human KIAA1999 cDNA was the largest fragment available but is missing ~1.3 kb of 5' coding sequence. To prepare the full-length rictor cDNA three DNA fragments were combined: a human EST (BG623200), a human cDNA (KIAA1999) and a PCR product spanning the gap between the EST and cDNA that was made from $1^{st}$ strand cDNA derived from HeLa cell total RNA. The PCR product was prepared using a forward primer corresponding to a sequence 5' of the BamH1 site at position 950 of the rictor ORF and a reverse primer corresponding to a sequence 3' of the PacI site at position 1616 and was added to the 3' end of the BG623200 EST. The SalI/PacI and PacI/XmaI segments of the extended BG623200 and KIAA1999, respectively, were subcloned into the prk5 expression vector in a three-way ligation. Prior to use, a corrupted section between the SpeI sites at 2682 and 3196 of the KIAA1999 cDNA was replaced with a wild-type fragment obtained by RT-PCR. In order to make these SpeI sites unique for the repair, the third SpeI site at 9135 of KIA1999 was removed by excising the non-coding fragment between SwaI sites at 6934 and 9367. All rictor fragments generated by PCR were confirmed by DNA sequencing.

Rictor sequences from several species were analyzed using the MEME Motif Discovery Tool (Bailey & Elkan, 1994, Proc Int Conf Intell Syst Mol Biol, 2, 28-36) to identify regions of sequence conservation and internal repeats. A motif length range of 20-50 amino acids was imposed on the algorithms. One internal repeat was found among all of the analyzed sequences. The repeats (except for S. cerevisiae) were aligned to each other using Clustalx v.1.81 (Thompson, et al., 1997, Nucleic Acids Res, 25, 4876-82).

Immunoprecipitations, Kinase Assays, and Metabolic Labeling $3 \times 10^6$ HeLa or HEK293T cells growing in 10-cm dishes were rinsed once with cold PBS and lysed on ice for 20 min in 1 ml of ice-cold Lysis Buffer (40 mM Hepes pH 7.5, 120 mM NaCl, 1 mM EDTA, 10 mM pyrophosphate, 10 mM glycerophosphate, 50 mM NaF, and EDTA-free protease inhibitors (Roche)) containing either 0.3% CHAPS or 1% Triton X-100. After centrifugation at 13,000×g for 10 min, 4 µg of the indicated antibodies were added to the cleared supernatant and incubated with rotation for 90-min. 20 µl of a 50% slurry of protein G-sepharose was then added and the incubation continued for 1 h. Captured immunoprecipitates were washed four times with Lysis Buffer and once with Wash Buffer (50 mM Hepes pH 7.5, 40 mM NaCl, and 2 mM EDTA). Samples were resolved by SDS-PAGE and proteins transferred to PVDF and visualized by immunoblotting as described (Kim et al., 2002, Cell, 110: 163-175). In vitro mTOR kinase assays were also as described (Kim et al., 2002, Cell, 110:163-175).

Two million HeLa cells in 6 cm dishes and transfected with the lentiviral plasmid encoding siRNAs targeting luciferase or mTOR were metabolically labeled by the addition of 0.5 mCi of [$^{32}$P]-orthophosphate (NEN) for 2 hr. Cells were rinsed twice with cold PBS and lysed in 300 ul of ice-cold CHAPS Lysis Buffer. After centrifugation, the cleared supernatants were collected, rictor immunoprecipitates prepared as above using with the rictor antibody, immunoprecipitates washed four times in Lysis Buffer, and proteins resolved by SDS-PAGE and radioactivity incorporation visualized by autoradiography.

Plasmid and siRNA Transfections

Effectene (Qiagen) was used to transfect 1.2 million HEK293T cells in 6-cm dishes with up to 1 µg of the expression plasmids indicated in the figure legends. 48 hours after DNA addition, the cells were rinsed once with PBS and lysed in 800 µl of ice-cold Lysis Buffer containing either CHAPS or Triton X-100 and analyzed by immunoprecipitation and immunoblotting as above. Sequences and transfection conditions for synthetic siRNAs targeting lamin, mTOR, and raptor have been described (Kim et al., 2002, Cell, 110:163-175) and are available at http://web. followed immediately by wi.mit.edu/sabatini/pub/siRNA_sequences.html. The sequences of the sense and anti-sense strands of the siRNA targeting rictor are ACUUGUGAAGAAUCGUAUCdTdT (SEQ ID NO: 7) and dTdTUGAACACUUCUUAGCAUAG (SEQ ID NO: 8), respectively. Those for PKCα are UCCUUGUCCAAGGAGGCUGdTdT (SEQ ID NO: 9) and dTdTAGGAACAGGUUCCUCCGAC (SEQ ID NO: 10).

Lentiviral shRNA Cloning, Production, and Infection

Desalted oligonucleotides (IDT) were cloned into LKO.1 (Stewart, et al., 2003, RNA, 9, 493-501) with the AgeI/EcoRI sites at the 3' end of the human U6 promoter. The sequences of the oligonucleotides are as follows:

(1) mTOR 609 sense (SEQ ID NO: 11):

CCGGTTCAGCGTCCCTACCTTCTTCTctcgagAGAAGAAGGTAGGGACGC
TGATTTTTG.

(2) mTOR 609 antisense (SEQ ID NO: 12):

AATTCAAAAATCAGCGTCCCTACCTTCTTCTctcgagAGAAGAAGGTAGG
GACGCTGAA.

(3) Raptor 4145 sense (SEQ ID NO: 13):

CCGGagggccctgctactcgcttttctcgagaaaagcgagtagcagggcc
ctTTTTTG.

(4) Raptor 4145 antisense (SEQ ID NO: 14):

AATTCAAAAAagggccctgctactcgcttttctcgagaaaagcgagtagc
agggccct.

(5) Rictor 3274 sense (SEQ ID NO: 15):

CCGGTACTTGTGAAGAATCGTATCTTctcgagAAGATACGATTCTTCACA
AGTTTTTTG.

(6) Rictor 3274 antisense (SEQ ID NO: 16):

AATTCAAAAAACTTGTGAAGAATCGTATCTTctcgagAAGATACGATTCT

TCACAAGTA.

The numbers described for the above oligonucleotides indicate the nucleotide positions in the transcripts (with position one set at the start codon) at which the 21 bp stem of the shRNA begins.

Plasmids were propagated in and purified from Stb12 bacterial cells (Invitrogen) and co-transfected together with the Delta VPR CMV VSVG plasmids into actively growing HEK293T using Fugene (Roche) as described (Stewart, et al., 2003, RNA, 9, 493-501). Virus-containing supernatants were collected at 36 and 60 hours after transfection, and concentrated by ultracentrifugation for 1.5 hrs at 23,000 RPM in an SW28 rotor at 4° C. Pellets were resuspended overnight at 4° C. in $\frac{1}{600}^{th}$ of the original volume. Cells were infected twice in the presence of 6 µg/ml protamine sulfate, selected for puromycin resistance and analyzed on the $5^{th}$ day after infection.

Generation and Application of dsRNA for RNAi in *Drosophila* S2 Cells

Primers were designed within the coding sequence of each respective gene to amplify a 700-800 bp cDNA fragment. The following primers were used:
(1) EGFP forward (SEQ ID NO: 17): ATGGTGAGCAAGGGCGAGGAGCTGT;
(2) EGFP reverse (SEQ ID NO: 18): TTACTTGTACAGCTCGTCCATGCCG;
(3) dTOR (CG5092) forward (SEQ ID NO: 19): CAGGAGTTATTTTAAATGTGCTTCG;
(4) dTOR reverse (SEQ ID NO: 20): CCAAAATTCTTTGATCAGCTTAAAA;
(5) dRaptor (CG4320) forward (SEQ ID NO: 21): TGTCTGACAACACCCATTAACATAG;
(6) dRaptor reverse (SEQ ID NO: 22): GTACTTGTATTCCTTGACCAGATCC;
(7) dRictor (CG8002) forward (SEQ ID NO: 23): GCTTATTCCTAGACAGCATTATCCA;
(8) dRictor reverse (SEQ ID NO: 24): TTTTGAGTACTTCGATGCCTTTTAC;
(9) dS6K (CG10539) forward (SEQ ID NO: 25): CCTTCATAGTGGAGCTAGTTTATGC; and
(10) dS6K reverse (SEQ ID NO: 26): CTTAGCGTTGTATCATCAGGTGAAT.

Each primer included a GAA and T7 promoter sequence (GAATTAATACGAC TCACTATAGGGAGA, SEQ ID NO: 27) at its 5' end. Primers were used in a one-step RT PCR reaction (Qiagen) to amplify a cDNA fragment using total *Drosophila* S2 cell RNA as template. The total RT-PCR reaction was purified using a PCR purification column (Qiagen) in a final volume of 40 µl. 8 µl of the RT-PCR product was then used as a template in a 20 µl in vitro transcription reaction using the Megascript kit (Ambion) to generate the corresponding dsRNA fragments. The GFP template was amplified from an EGFP expression plasmid (Stratagene). *Drosophila* S2 cells actively growing in Schneider medium (Life Technologies) were washed and resuspended in *Drosophila* SFM (Life Technologies) to a final density of $1 \times 10^6$ cells in 1 ml volume. 30 µg of dsRNA was added to the 1 ml of cells in SFM and incubated for 45 min at 25° C. 2 ml of Schneider medium with 10% serum was then added back to the cells. After 24 hours, the cells were starved again and an additional 30 µg of dsRNA was added. After 4 days cells were harvested, washed once with cold PBS, lysed in the 1% Triton X-100 Lysis Buffer and analyzed by immunoblotting as above. Antibodies developed against mammalian phospho-S6K1, phospho-PKCα and PKCα were used to detect the *Drosophila* homologues of these proteins/modifications.

Immunofluorescence

HeLa cells transduced with the siRNA-expressing lentiviruses or transfected with synthetic siRNAs were cultured overnight on fibronectin-coated glass coverslips. Cells were fixed for 15 min with 3.7% formaldehyde in phosphate buffered saline (PBS), permeablized for 10 min in 0.5% NP40 in PBS containing 1 mM $CaCl_2$ and $MgCl_2$ (PBS+), and washed twice in PBS+. Nonspecific binding sites were blocked for 30 min by incubating in PBS+ containing 10% fetal bovine serum followed by 1 hr incubation in the same blocking buffer containing a 1:1000 dilution of the paxillin antibody. After washing in PBS+, blocking buffer containing 1:800 of the Alexa Fluor 488-conjugated secondary anti-mouse antibody, 1:800 of Texas Red-X-phalloidin and 1:1000 of Hoechst dye was added to the coverslips for 1 hr. The coverslips were then washed twice with PBS+, mounted in glycerol containing 0.1% p-phenylenediamine on glass slides, and visualized with fluorescence microscopy.

INCORPORATION BY REFERENCE

All publications and patents mentioned herein are hereby incorporated by reference in their entirety as if each individual publication or patent was specifically and individually indicated to be incorporated by reference.

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. An isolated polypeptide comprising an amino acid sequence at least 97% identical to SEQ ID NO: 3, wherein the amino acid sequence at least 97% identical to SEQ ID NO: 3 is not identical to SEQ ID NO: 3 and can form a complex with the polypeptide represented by SEQ ID NO: 52.

2. The isolated polypeptide of claim 1, wherein the amino acid sequence at least 97% identical to SEQ ID NO: 3 is at least 98% identical to SEQ ID NO: 3.

3. An isolated polypeptide comprising SEQ ID NO: 3.

4. An isolated, purified or recombinant complex comprising an mTOR-associated protein (mTOR-AP) polypeptide, wherein the mTOR-AP polypeptide comprises an amino acid sequence at least 99% identical to SEQ ID NO: 3, and wherein the amino acid sequence at least 99% identical to SEQ ID NO: 3 is not identical to SEQ ID NO: 3 and can form a complex with the polypeptide represented by SEQ ID NO: 52.

5. An isolated, purified or recombinant complex comprising an mTOR-associated protein (mTOR-AP) polypeptide, wherein the mTOR-AP polypeptide comprises SEQ ID NO: 3.

6. The complex of claim 4, further comprising a G protein β subunit Like (GβL) polypeptide at least 95% identical to SEQ ID NO: 6, wherein the polypeptide at least 95% identical to SEQ ID NO: 6 can form a complex with the polypeptide represented by SEQ ID NO: 52.

7. The isolated polypeptide of claim 1, wherein the amino acid sequence at least 97% identical to SEQ ID NO: 3 is at least 99% identical to SEQ ID NO: 3.

8. The isolated polypeptide of claim 3, wherein the isolated polypeptide consists of SEQ ID NO: 3.

9. The isolated, purified, or recombinant complex of claim 4, further comprising the mTOR polypeptide of SEQ ID NO: 52.

10. The isolated, purified, or recombinant complex of claim 5, wherein the mTOR-AP polypeptide consists of SEQ ID NO: 3.

11. The isolated, purified, or recombinant complex of claim 4, further comprising the G protein 13 subunit Like (GβL) polypeptide of SEQ ID NO: 6.

12. The isolated polypeptide of claim 1, wherein the polypeptide is a recombinant protein containing a heterologous domain.

13. The isolated polypeptide of claim 3, wherein the polypeptide is a recombinant protein containing a heterologous domain.

14. The isolated, purified, or recombinant complex of claim 5, further comprising a G protein 13 subunit Like (GβL) polypeptide at least 95% identical to SEQ ID NO: 6, wherein the polypeptide at least 95% identical to SEQ ID NO: 6 can form a complex with the polypeptide represented by SEQ ID NO: 52.

15. The isolated, purified, or recombinant complex of claim 5, further comprising the G protein 13 subunit Like (GβL) polypeptide of SEQ ID NO: 6.

16. An isolated polypeptide that comprises a fragment of SEQ ID NO: 3, wherein the fragment of SEQ ID NO: 3 can form a complex with the polypeptide represented by SEQ ID NO: 52.

17. The isolated polypeptide of claim 16, wherein the polypeptide is a recombinant protein containing a heterologous domain.

* * * * *